United States Patent
Koumbaris et al.

(10) Patent No.: US 12,421,551 B2
(45) Date of Patent: *Sep. 23, 2025

(54) MULTIPLEXED PARALLEL ANALYSIS OF TARGETED GENOMIC REGIONS FOR NON-INVASIVE PRENATAL TESTING

(71) Applicant: MEDICOVER PUBLIC CO LTD, Nicosia (CY)

(72) Inventors: George Koumbaris, Lythrodontas (CY); Elena Kypri, Nicosia (CY); Kyriakos Tsangaras, Limassol (CY); Achilleas Achilleos, Limassol (CY); Petros Mina, Nicosia (CY); Elisavet A. Papageorgiou, Nicosia (CY); Philippos C. Patsalis, Nicosia (CY)

(73) Assignee: MEDICOVER PUBLIC CO LTD, Nicosia (CY)

( * ) Notice: Subject to any disclaimer, the term of this patent is extended or adjusted under 35 U.S.C. 154(b) by 1264 days.

This patent is subject to a terminal disclaimer.

(21) Appl. No.: 17/147,946

(22) Filed: Jan. 13, 2021

(65) Prior Publication Data

US 2021/0130900 A1 May 6, 2021

Related U.S. Application Data

(63) Continuation of application No. 15/160,981, filed on May 20, 2016, now Pat. No. 11,111,538.

(60) Provisional application No. 62/263,320, filed on Dec. 4, 2015, provisional application No. 62/165,593, filed on May 22, 2015.

(51) Int. Cl.
*C12Q 1/6883* (2018.01)
*C12Q 1/6827* (2018.01)
*G16B 30/00* (2019.01)
*G16B 30/10* (2019.01)

(52) U.S. Cl.
CPC ......... *C12Q 1/6883* (2013.01); *C12Q 1/6827* (2013.01); *G16B 30/00* (2019.02); *C12Q 2600/156* (2013.01); *G16B 30/10* (2019.02)

(58) Field of Classification Search
CPC .............. C12Q 1/6883; C12Q 1/6827; C12Q 2600/156; C12Q 2535/122; C12Q 2537/143; C12Q 2537/16; G16B 30/00; G16B 30/10

See application file for complete search history.

(56) References Cited

U.S. PATENT DOCUMENTS

| | | | |
|---|---|---|---|
| 6,258,540 B1 | 7/2001 | Lo et al. | |
| 7,888,017 B2 | 2/2011 | Quake et al. | |
| 8,008,018 B2 | 8/2011 | Quake et al. | |
| 8,195,415 B2 | 6/2012 | Fan et al. | |
| 8,296,076 B2 | 10/2012 | Fan et al. | |
| 8,620,593 B2 | 12/2013 | Lo et al. | |
| 8,682,594 B2 | 3/2014 | Fan et al. | |
| 8,825,412 B2 | 9/2014 | Rabinowitz et al. | |
| 9,249,462 B2 | 2/2016 | Patsalis et al. | |
| 2001/0053519 A1 | 12/2001 | Fodor et al. | |
| 2007/0275402 A1 | 11/2007 | Lo et al. | |
| 2010/0105049 A1 | 4/2010 | Ehrich et al. | |
| 2011/0201507 A1 | 8/2011 | Rava et al. | |
| 2012/0034603 A1 | 2/2012 | Oliphant et al. | |
| 2012/0208710 A1 | 8/2012 | Fan et al. | |
| 2012/0258892 A1 | 10/2012 | Wang | |
| 2012/0270739 A1 | 10/2012 | Rava et al. | |
| 2012/0282613 A1 | 11/2012 | Patsalis et al. | |
| 2013/0237431 A1 | 9/2013 | Lo et al. | |
| 2013/0303382 A1 | 11/2013 | Pollner et al. | |
| 2014/0195164 A1* | 7/2014 | Lo .......................... | G16B 20/10 |
| | | | 702/19 |

FOREIGN PATENT DOCUMENTS

| | | |
|---|---|---|
| JP | 2008-502332 A | 1/2008 |
| JP | 2008-521389 A | 6/2008 |
| JP | 2009-232767 A | 10/2009 |
| WO | 1991/07660 A1 | 11/1990 |
| WO | 2003/020974 A2 | 3/2003 |
| WO | 2005/028674 A2 | 3/2005 |
| WO | 2005/035725 A2 | 4/2005 |
| WO | 2005/123942 A2 | 12/2005 |
| WO | 2006/056480 A2 | 6/2006 |

(Continued)

OTHER PUBLICATIONS

Treangen et al. (Nature Reviews Genet. 2012, 13:36-46) (Year: 2012).*
Gnirke et al. (Nat. Biotech., 2009, 27(2):182-189) (Year: 2009).*
Agilent (2009) "The Agilent Technologies SureSelect Platform for Target Enrichment" https://www.agilent.com/cs/library/posters/public/SureSelect_Platform_for_Target_Enrichment.pdf; accessed on Jan. 11, 2019.
Aria Diagnostics, Inc. [<http://www.ariadx.com>] [cited May 12, 2013].
Avent et al., "Post-genomics studies and their application to non-invasive prenatal diagnosis," Semin Fetal Neonatal Med, 13(2):91-98 (2008).

(Continued)

*Primary Examiner* — Jeremy C Flinders
(74) *Attorney, Agent, or Firm* — MEDLER FERRO WOODHOUSE & MILLS PLLC

(57) ABSTRACT

The invention provides methods for non-invasive prenatal testing that allow for detecting risk of chromosomal and subchromosomal abnormalities, including but not limited to aneuploidies, microdeletions and microduplications, insertions, translocations, inversions and small-size mutations including point mutations and mutational signatures. The methods of the invention utilize a pool of TArget Capture Sequences (TACS) to enrich for sequences of interest in a mixed sample containing both maternal and fetal DNA, followed by massive parallel sequencing and statistical analysis of the enriched population to thereby detect the risk of a genetic abnormality in the fetal DNA. Kits for carrying out the methods of the invention are also provided.

10 Claims, 41 Drawing Sheets

Specification includes a Sequence Listing.

(56) References Cited

FOREIGN PATENT DOCUMENTS

| WO | 2007/007337 A1 | 1/2007 |
|---|---|---|
| WO | 2007/044780 A1 | 4/2007 |
| WO | 2007/132167 A2 | 11/2007 |
| WO | 2009/013492 A1 | 1/2009 |
| WO | 2011/041485 A1 | 9/2010 |
| WO | 2011/051283 A1 | 5/2011 |
| WO | 2011/092592 A1 | 8/2011 |

OTHER PUBLICATIONS

Babraham Institute. FastQC. 2015 [cited Apr. 7, 2015]; Available from: <http://www.bioinformatics.babraham.ac.uk/projects/fastqc/>.
Bianchi et al., "Genome-Wide Fetal Aneuploidy Detection by Maternal Plasma DNA Sequencing," Obstet Gynecol. 119(5) 890-901 (2012).
Bianchi et al., "Noninvasive prenatal diagnosis of fetal Rhesus D: ready for Prime(r) Time," Obstet Gynecol 106(4): 841-844 (2005).
Broad Institute. Picard. 2015 [cited Apr. 7, 2015]; Available from: <http://broadinstitute.github.io/picard/>.
Broad Institute. The Genome Analysis Toolkit. 2015 [cited Apr. 7, 2015]; Available from: https://www.broadinstitute.org/gatk/ <http://www.broadinstitute.org/gatk/>.
Chan et al., "Size distributions of maternal and fetal DNA in maternal plasma," Clin Chem 50(1): 88-92 (2004).
Chen et al., "Noninvasive Prenatal Diagnosis of Fetal Trisomy 18 and Trisomy 13 by Maternal Plasma DNA Sequencing," PLoS One 6(7): e21791 (2011).
Chim et al., "Detection of the placental epigenetic signature of the maspin gene in maternal plasma," PNAS USA 102(41):14753-14758 (2005).
Chim et al., "Systematic Search for Placental DNA-Methylation Markers on Chromosome 21: Toward a Maternal Plasma-Based Epigenetic Test for Fetal Trisomy 21," Clinical Chemistry 54(3):500-511 (2008).
Chiu et al., "Maternal Plasma DNA Analysis with Massively Parallel Sequencing by Ligation for Noninvasive Prenatal Diagnosis of Trisomy 21," Clinical Chemistry 56(3):459-463 (2010).
Chiu et al., "Noninvasive prenatal diagnosis of fetal chromosomal aneuploidy by massively parallel genomic Sequencing of DNA in maternal plasma," PNAS USA 105(51): 20458-20463 (2008).
Chiu et al., "Hypermethylation of RASSF1A in Human and Rhesus Placentas," The American Journal of Pathology 170(3):941-950 (2007).
Chu et al., "A microarray-based approach for the identification of epigenetic biomarkers for the noninvasive Diagnosis of fetal disease," Prenat. Diagn 29:1020-1030 (2009).
Ehrich et al., "Noninvasive detection of fetal trisomy 21 by sequencing of DNA in maternal blood: a study in a „linical setting," Am J Obstet Gynecol., 204(3): 205 e1-11 (2011).
Fan et al., "Noninvasive diagnosis of fetal aneuploidy by shotgun sequencing DNA from maternal blood," PNAS USA 105(42):16266-16271 (2008).
Fazzari et al., "Epigenomics: Beyond CpG Islands," Nature Reviews Genetics, vol. 5:446-455 (2004).
Flori, et al., "Circulating cell-free fetal DNA in maternal serum appears to originate from cyto- and syncytio-trophoblastic cells Case Report," Human Reproduction 19(3):723-724 (2004).
Go et al., "Non-invasive aneuploidy detection using free fetal DNA and RNA in maternal plasma: recent progress and future possibilities," Human Reproduction Update 17(3):372-382 (2011).
Grunau et al., "Bisulfite genomic sequencing: systematic investigation of critical experimental parameters," Nucleic Acids Research 29(13):e65, 1-7 (2001).
Honda et al., "Fetal gender determination in early pregnancy through qualitative and quantitative analysis of fetal DNA in maternal serum," Hum. Genet 110:75-79 (2002).

Hooks et al., "Non-invasive risk assessment of fetal sex chromosome aneuploidy through directed analysis and incorporation of fetal fraction," Prenat Diagn 34(5):496-499 (2014).
Hulten et al., "Rapid and simple prenatal diagnosis of common chromosome disorders: advantages and Disadvantages of the molecular methods FISH and QF-PCR," Reproduction 126:279-297 (2003).
Koehler et al., "Thermodynamic properties of DNA sequences: characteristic values for the human genome," Bioinformatics 21(16):3333-3339 (2005).
Li et al., "Fast and accurate short read alignment with Burrows-Wheeler transform," Bioinformatics 25(14):1754-1760 (2009).
Li et al., "The Sequence Alignment/Map format and SAMtools," Bioinformatics 25(16): 2078-2079 (2009).
Liao et al., "Noninvasive prenatal diagnosis of fetal trisomy 21 by allelic ratio analysis using targeted massively parallel sequencing of maternal plasma DNA," PLoS One 7(5): e38154 (2012).
Lo et al., "Plasma placental RNA allelic ratio permits noninvasive prenatal chromosomal aneuploidy detection," Nature Medicine 13(2):218-223 (2007).
Lo et al., "Prenatal diagnosis of fetal RhD status by molecular analysis of maternal plasma," N Engl J Med 39(24):1734-1738 (1998).
Lo et al., "Presence of fetal DNA in maternal plasma and serum," Lancet 350(9076):485-487 (1997).
Lo et al., "Quantitative analysis of fetal DNA in maternal plasma and serum: implications for noninvasive prenatal diagnosis," Am J Hum Genet 62(4):768-775 (1998).
Lun et al., "Microfluidics digital PCR reveals a higher than expected fraction of fetal DNA in maternal plasma," Clin Chem 54(10):1664-1672 (2008).
Maricic et al., "Multiplexed DNA sequence capture of mitochondrial genomes using PCR products," PLoS One 5(11):e14004 (2010).
Martin, "Cutadapt removes adapter sequences from high-throughput sequencing reads," EMBnet.journal 17(1):10-12 (2011).
Masuzaki et al., "Detection of cell free placental DNA in maternal plasma: direct evidence from three cases of confined placental mosaicism," J Med. Genet. 41:289-292 (2004).
Meyer et al., "Illumina sequencing library preparation for highly multiplexed target capture and sequencing," Cold Spring Harb Protoc 2010(6):pdb-rot5448 (2010).
Ng et al., "mRNA of placental origin is readily detectable in maternal plasma," Proc Natl Acad Sci USA 100(8):4748-4753 (2003).
Nicolaides et al., "Validation of targeted sequencing of single-nucleotide polymorphisms for non-invasive prenatal detection of aneuploidy of chromosomes 13, 18, 21, X, and Y.," Prenat Diagn., 33(6):575-579 (2013).
Old et al., "Candidate epigenetic biomarkers for non-invasive prenatal diagnosis of Down syndrome," Reprod Biomed Online 15(2):227-235 (2007).
Palomaki et al., "DNA sequencing of maternal plasma reliably identifies trisomy 18 and trisomy 13 as well as Down syndrome: an international collaborative study," Genet Med 14(3):296-305 (2012).
Palomaki et al., "DNA sequencing of maternal plasma to detect Down syndrome: an international clinical validation study," Genet Med, 13(11): 913-920 (2011).
Papageorghiou et al., "Clinical evaluation of The IONA test: a non-invasive prenatal screening test for Wrisomy 21, 18 and 13," Ultrasound Obstet Gynecol. 47(2):188-193 (2016).
Papageorgiou et al., "Author's response regarding MeDIP-qPCR approach for non-invasive prenatal Diagnosis of Down syndrome: accuracy and reproducibility," Prenat Diagn 33(4):404-405 (2013).
Papageorgiou et al., "Fetal specific DNA methylation ratio permits non-invasive prenatal diagnosis of trisomy 21," Nature Medicine 17:510-513 (2011).
Papageorgiou et al., "Sites of differential DNA methylation between placenta and peripheral blood: molecular markers for noninvasive prenatal diagnosis of aneuploidies," Am J Pathol. 174(5):1609-1618 (2009).
Papageorgiou et al., "Non-invasive prenatal diagnosis of aneuploidies: new technologies and clinical applications," Genome Medicine 4(46):1-12 (2012).

(56) References Cited

OTHER PUBLICATIONS

Patsalis et al., "A new non-invasive prenatal diagnosis of Down syndrome through epigenetic markers and real-time qPCR," Expert Opin. Biol. Ther. 12(Suppl. 1):S155-S161 (2012).
Patsalis, et al., "Non-Invasive Prenatal Diagnosis (NIPD) of Down Syndrome using real time qPCR," European Cytogeneticists Association Newsletter 30:5-10 (2012).
Poon et al., "Differential DNA Methylation between Fetus and Mother as a Strategy for Detecting Fetal DNA in Maternal Plasma," Clinical Chemistry 48(1):35-41 (2002).
Puszyk, University of Warwick. Department of Biological Sciences. Sep. 2008.
Python Software Foundation. python. 2015 [cited Apr. 7, 2015]; Available from: https://www.python.org/ <http://www. oython. org/>.
Rakyan et al., "An integrated resource for genome-wide identification and analysis of human tissue-specific differentially methylated regions (IDMRs)," Genome Research 18:1518-1529 (2008).
Reddy et al., "Effects of sequence variation on differential allelic transcription factor occupancy and gene expression," Genome Research 22(5):860-869 (2012).
Samango et al., "SNP-based non-invasive prenatal testing detects sex chromosome aneuploidies with high accuracy," Prenat. Diagn. 33(7): 643-649 (2013).
Samorodnitsky et al., "Comparison of Custom Capture for Targeted Next-Generation DNA Sequencing," J. Mol. Diag. 17(1):64-75 (2015).
Sehnert et al., "Optimal detection of fetal chromosomal abnormalities by massively parallel DNA sequencing of cell-free fetal DNA from maternal blood," Clin Chem 57(7):1042-1049 (2011).
Sequenom, Inc. [<http://www.sequenom.com>] [cited May 12, 2013].
Sparks et al., "Noninvasive prenatal detection and selective analysis of cell-free DNA obtained from maternal blood: evaluation for trisomy 21 and trisomy 18," American Journal of Obstetrics & Gynecology, 206(319):1-9 (2012).
Sparks et al., "Selective analysis of cell-free DNA in maternal blood for evaluation of fetal trisomy," Prenat Diagn 32(1):3-9 (2012).
Stokowlski et al., "Clinical performance of non-invasive prenatal testing (NIPT) using targeted cell-free DNA analysis in maternal plasma with microarrays or next generation sequencing (NGS) is consistent across multiple controlled clinical studies," Prenatal Diagnosis 35:1243-1246 (2015).
Sulonen et al., "Comparison of solution-based exome capture methods for next generation sequencing," Genome Biology 12(9):1-8 (2011).
Tewhey et al., "Enrichment of sequencing targets from the human genome by solution hybridization," Genome Biol. 10(10):R116 (2009).
The R Foundation. The R Project for Statistical Computing. 2015 [cited Apr. 7, 2015]; Available from: <http://www.r-project.org/>.

Tong et al., "Noninvasive Prenatal Detection of Trisomy 21 by an Epigenetic-Genetic Chromosome-Dosage Approach," Clinical Chemistry 56(1):90-98 (2010).
Tsaliki et al., "MeDIP real-time qPCR of maternal peripheral blood reliably identifies trisomy 21," Prenat Diagn 32(10):996-1001 (2012).
Tsangaras et al., "Hybridization Capture Using Short PCR Products Enriches Small Genomes by Capturing ::1anking Sequences (CapFlank)," PLoS ONE, 9(10): e109101 (2014).
Tsui et al., "A Microarray Approach for Systematic Identification of Placental-Derived RNA Markers in Maternal Plasma," Methods in Molecular Biology 444:275-289 (2008).
Tsui et al., "Detection of Tisomy 21 by Quantitative Mass Spectrometric Analysis of Single-Nucleotide Polymorphisms," Clinical Chemistry 51(12):2358-2362 (2005).
Tsui et al., "Non-invasive prenatal detection of fetal trisomy 18 by RNA-SNP allelic ratio analysis using maternal plasma SERPINB2 mRNA: a feasibility study," Prenatal Diagnosis 29:1031-1037 (2009).
Tynan et al., "Application of risk score analysis to low-coverage whole genome sequencing data for the noninvasive detection of trisomy 21, trisomy 18, and trisomy 13," Prenat Diagn. 36(1):56-62 (2015).
UCSC Genome Bioinformatics. UCSC Genome Browser Acknowledgments. 2015 [cited Apr. 7, 2015]; Available from rittp://genome.ucsc.edu/goldenPath/credits.html#human_credits <http://genome.ucsc.edu/goldenPath/credits.html>.
Verinata health, Inc. (<http://www.verinata.com>) [cited May 12, 2013].
Wald et al., "Integrated Screening for Down's Syndrome Based on Tests Performed During the First and Second Trimesters," The New England Journal of Medicine 341(7):461-467 (1999).
Weber et al., "Chromosome-wide and promoter-specific analyses identify sites of differential DNA methylation in normal and transformed human cells," Nature Genetics 37(8):853-862 (2005).
Weisz et al., "An update on antenatal screening for Down's syndrome and specific implications for assisted reproduction pregnancies," Human Reproduction Update 12(5):513-518 (2006).
Yoon et al., "Sensitive and accurate detection of copy number variants using read depth of coverage," Genome Research 19(9):1586-1592 (2009).
Zimmermann et al., "Noninvasive prenatal aneuploidy testing of chromosomes 13, 18, 21, X, and Y, using targeted sequencing of polymorphic loci," Prenat Diagn, 32(13): 1233-1241 (2012).
International Preliminary Report on Patentability and Written Opinion for Application No. PCT/I82016/000833, 17 pages, dated May 29, 2017.
International Preliminary Report on Patentability and Written Opinion for Application No. PCT/182011/000217, 8 pages, dated Jul. 31, 2012.
International Search Report and Written Opinion for Application No. PCT/IB2011/000217, 13 pages, dated Aug. 23, 2011.

\* cited by examiner

| chromosome | start | stop |
| --- | --- | --- |
| chr13 | 91049752 | 91050001 |
| chr13 | 92177139 | 92177388 |
| chr13 | 93071049 | 93071298 |
| chr13 | 94326973 | 94327222 |
| chr13 | 94415507 | 94415756 |
| chr13 | 95600034 | 95600283 |
| chr13 | 112910529 | 112910778 |
| chr13 | 53328405 | 53328654 |
| chr13 | 20533985 | 20534234 |
| chr13 | 20535728 | 20535977 |
| chr13 | 20544227 | 20544476 |
| chr13 | 20567359 | 20567607 |
| chr13 | 20577159 | 20577407 |
| chr13 | 20598772 | 20599021 |
| chr13 | 20600556 | 20600804 |
| chr13 | 20610779 | 20611027 |
| chr13 | 20621336 | 20621585 |
| chr13 | 20624392 | 20624641 |
| chr13 | 20625461 | 20625710 |
| chr13 | 20632609 | 20632857 |
| chr13 | 20635196 | 20635444 |
| chr13 | 21127405 | 21127653 |
| chr13 | 21163998 | 21164247 |
| chr13 | 21170950 | 21171199 |
| chr13 | 21172515 | 21172764 |
| chr13 | 21173774 | 21174022 |
| chr13 | 21182580 | 21182828 |
| chr13 | 21203385 | 21203634 |
| chr13 | 21217173 | 21217422 |
| chr13 | 21228403 | 21228652 |
| chr13 | 21237418 | 21237666 |
| chr13 | 21239719 | 21239968 |

| chromosome | start | stop |
| --- | --- | --- |
| chr13 | 21245232 | 21245481 |
| chr13 | 21251423 | 21251672 |
| chr13 | 21276601 | 21276850 |
| chr13 | 21296989 | 21297237 |
| chr13 | 21321012 | 21321261 |
| chr13 | 21330138 | 21330386 |
| chr13 | 21348854 | 21349102 |
| chr13 | 21351692 | 21351941 |
| chr13 | 21356527 | 21356775 |
| chr13 | 21361621 | 21361869 |
| chr13 | 21396343 | 21396591 |
| chr13 | 21399744 | 21399992 |
| chr13 | 21417352 | 21417601 |
| chr13 | 21422981 | 21423229 |
| chr13 | 21607075 | 21607324 |
| chr13 | 21631007 | 21631256 |
| chr13 | 22114658 | 22114907 |
| chr13 | 22130956 | 22131205 |
| chr13 | 22189915 | 22190164 |
| chr13 | 22270443 | 22270692 |
| chr13 | 22396225 | 22396474 |
| chr13 | 22609278 | 22609527 |
| chr13 | 22691882 | 22692131 |
| chr13 | 22765144 | 22765393 |
| chr13 | 27175379 | 27175628 |
| chr13 | 27405837 | 27406086 |
| chr13 | 27646720 | 27646969 |
| chr13 | 27674747 | 27674996 |
| chr13 | 27969360 | 27969609 |
| chr13 | 27978231 | 27978480 |
| chr13 | 28003481 | 28003730 |
| chr13 | 28073180 | 28073429 |

| chromosome | start | stop |
| --- | --- | --- |
| chr13 | 28077809 | 28078058 |
| chr13 | 28212786 | 28213035 |
| chr13 | 28302961 | 28303210 |
| chr13 | 28325874 | 28326123 |
| chr13 | 28395893 | 28396142 |
| chr13 | 28549591 | 28549840 |
| chr13 | 28592602 | 28592851 |
| chr13 | 28608293 | 28608542 |
| chr13 | 28617043 | 28617292 |
| chr13 | 28622471 | 28622720 |
| chr13 | 28623594 | 28623843 |
| chr13 | 28941450 | 28941699 |
| chr13 | 28958898 | 28959147 |
| chr13 | 28960375 | 28960624 |
| chr13 | 29003985 | 29004234 |
| chr13 | 29052686 | 29052935 |
| chr13 | 52293092 | 52293341 |
| chr13 | 52302656 | 52302905 |
| chr13 | 53286404 | 53286653 |
| chr13 | 53306303 | 53306552 |
| chr13 | 53497224 | 53497473 |
| chr13 | 53548644 | 53548893 |
| chr13 | 53652715 | 53652964 |
| chr13 | 53861872 | 53862121 |
| chr13 | 53897429 | 53897678 |
| chr13 | 53938205 | 53938454 |
| chr13 | 54626806 | 54627055 |
| chr13 | 54740174 | 54740423 |
| chr13 | 54753834 | 54754083 |
| chr13 | 54768238 | 54768487 |
| chr13 | 54773333 | 54773582 |
| chr13 | 54910969 | 54911218 |

Figure 2A

| chromosome | start | stop |
|---|---|---|
| chr13 | 54917347 | 54917596 |
| chr13 | 54926251 | 54926500 |
| chr13 | 55009732 | 55009981 |
| chr13 | 59785342 | 59785591 |
| chr13 | 60086302 | 60086551 |
| chr13 | 60668020 | 60668269 |
| chr13 | 60707747 | 60707996 |
| chr13 | 60975949 | 60976198 |
| chr13 | 61177164 | 61177413 |
| chr13 | 61495655 | 61495904 |
| chr13 | 67720914 | 67721163 |
| chr13 | 67799557 | 67799806 |
| chr13 | 70101783 | 70102032 |
| chr13 | 71512697 | 71512946 |
| chr13 | 71821654 | 71821903 |
| chr13 | 72405844 | 72406093 |
| chr13 | 74087455 | 74087704 |
| chr13 | 74192477 | 74192726 |
| chr13 | 74260893 | 74261142 |
| chr13 | 78218064 | 78218313 |
| chr13 | 88033439 | 88033688 |
| chr13 | 90954378 | 90954627 |
| chr13 | 91290109 | 91290358 |
| chr13 | 91874767 | 91875016 |
| chr13 | 92125914 | 92126163 |
| chr13 | 92308079 | 92308328 |
| chr13 | 92971372 | 92971621 |
| chr13 | 94063232 | 94063481 |
| chr13 | 94453836 | 94454085 |
| chr13 | 94713643 | 94713892 |
| chr13 | 95766126 | 95766375 |
| chr13 | 95814599 | 95814848 |

| chromosome | start | stop |
|---|---|---|
| chr13 | 111956688 | 111956937 |
| chr13 | 112517966 | 112518215 |
| chr13 | 112531519 | 112531768 |
| chr13 | 112986709 | 112986958 |
| chr13 | 113000054 | 113000303 |
| chr13 | 21391429 | 21391678 |
| chr13 | 21394616 | 21394865 |
| chr13 | 21404268 | 21404516 |
| chr13 | 21618233 | 21618482 |
| chr13 | 21619521 | 21619769 |
| chr13 | 21629602 | 21629851 |
| chr13 | 21654127 | 21654376 |
| chr13 | 22215795 | 22216044 |
| chr13 | 22227261 | 22227510 |
| chr13 | 22243011 | 22243260 |
| chr13 | 22255153 | 22255402 |
| chr13 | 22639387 | 22639636 |
| chr13 | 27183101 | 27183350 |
| chr13 | 27387690 | 27387939 |
| chr13 | 30466189 | 30466438 |
| chr13 | 30977198 | 30977447 |
| chr13 | 31061235 | 31061484 |
| chr13 | 31205037 | 31205286 |
| chr13 | 32625308 | 32625557 |
| chr13 | 34428102 | 34428351 |
| chr13 | 36054899 | 36055148 |
| chr13 | 36105686 | 36105935 |
| chr13 | 40676702 | 40676951 |
| chr13 | 40745383 | 40745632 |
| chr13 | 49281723 | 49281972 |
| chr13 | 53624527 | 53624776 |
| chr13 | 60069277 | 60069526 |

| chromosome | start | stop |
|---|---|---|
| chr13 | 60654975 | 60655224 |
| chr13 | 61151386 | 61151635 |
| chr13 | 62064603 | 62064852 |
| chr13 | 71479359 | 71479608 |
| chr13 | 39233534 | 39233783 |
| chr13 | 39281667 | 39281916 |
| chr13 | 39343524 | 39343773 |
| chr13 | 39444897 | 39445146 |
| chr13 | 39469458 | 39469707 |
| chr13 | 39486237 | 39486486 |
| chr13 | 39541262 | 39541511 |
| chr13 | 39597307 | 39597556 |
| chr13 | 39662550 | 39662799 |
| chr13 | 39681445 | 39681694 |
| chr13 | 39707053 | 39707302 |
| chr13 | 39791099 | 39791348 |
| chr13 | 39882804 | 39883053 |
| chr13 | 39887397 | 39887646 |
| chr13 | 40023278 | 40023527 |
| chr13 | 40038277 | 40038526 |
| chr13 | 40071926 | 40072175 |
| chr13 | 40138914 | 40139163 |
| chr13 | 40171414 | 40171663 |
| chr13 | 40405751 | 40406000 |
| chr13 | 40483291 | 40483540 |
| chr13 | 40562330 | 40562579 |
| chr13 | 40590631 | 40590880 |
| chr13 | 40633944 | 40634193 |
| chr13 | 40644042 | 40644291 |
| chr13 | 40661582 | 40661831 |
| chr13 | 40667939 | 40668188 |
| chr13 | 40684306 | 40684555 |

Figure 2B

| chromosome | start | stop |
|---|---|---|
| chr13 | 40747946 | 40748195 |
| chr13 | 40767281 | 40767530 |
| chr13 | 41165017 | 41165266 |
| chr13 | 41176869 | 41177118 |
| chr13 | 41573543 | 41573792 |
| chr13 | 41581284 | 41581533 |
| chr13 | 41588844 | 41589093 |
| chr13 | 41628316 | 41628565 |
| chr13 | 41633944 | 41634193 |
| chr13 | 41827812 | 41828061 |
| chr13 | 42280338 | 42280587 |
| chr13 | 42349979 | 42350228 |
| chr13 | 42589616 | 42589865 |
| chr13 | 42773088 | 42773337 |
| chr13 | 42811933 | 42812182 |
| chr13 | 44211957 | 44212206 |
| chr13 | 44239246 | 44239495 |
| chr13 | 44247433 | 44247682 |
| chr13 | 44359516 | 44359765 |
| chr13 | 44388992 | 44389241 |
| chr13 | 44493443 | 44493692 |
| chr13 | 44557886 | 44558135 |
| chr13 | 44959162 | 44959411 |
| chr13 | 45043950 | 45044199 |
| chr13 | 45115235 | 45115484 |
| chr13 | 45147386 | 45147635 |
| chr13 | 47067063 | 47067312 |
| chr13 | 47120595 | 47120844 |
| chr13 | 47154937 | 47155186 |
| chr13 | 47258834 | 47259083 |
| chr13 | 47261849 | 47262098 |
| chr13 | 47286641 | 47286890 |

| chromosome | start | stop |
|---|---|---|
| chr13 | 47314093 | 47314342 |
| chr13 | 47623498 | 47623747 |
| chr13 | 48562058 | 48562307 |
| chr13 | 48698166 | 48698415 |
| chr13 | 48762184 | 48762433 |
| chr13 | 48806515 | 48806764 |
| chr13 | 48811339 | 48811588 |
| chr13 | 49119202 | 49119451 |
| chr13 | 49479756 | 49480005 |
| chr13 | 49505070 | 49505319 |
| chr13 | 49530727 | 49530976 |
| chr13 | 50387096 | 50387317 |
| chr13 | 50960526 | 50960775 |
| chr13 | 51783208 | 51783457 |
| chr13 | 51816719 | 51816968 |
| chr13 | 51825241 | 51825490 |
| chr13 | 52025153 | 52025402 |
| chr13 | 52249504 | 52249753 |
| chr13 | 29111011 | 29111260 |
| chr13 | 29192994 | 29193243 |
| chr13 | 29233772 | 29234021 |
| chr13 | 29310139 | 29310388 |
| chr13 | 29563140 | 29563389 |
| chr13 | 29580073 | 29580322 |
| chr13 | 29929175 | 29929424 |
| chr13 | 29934475 | 29934724 |
| chr13 | 29939640 | 29939889 |
| chr13 | 29957853 | 29958102 |
| chr13 | 29995732 | 29995981 |
| chr13 | 30003375 | 30003624 |
| chr13 | 30014954 | 30015203 |
| chr13 | 30114022 | 30114271 |

| chromosome | start | stop |
|---|---|---|
| chr13 | 30145894 | 30146143 |
| chr13 | 30187253 | 30187502 |
| chr13 | 30421518 | 30421767 |
| chr13 | 30531947 | 30532196 |
| chr13 | 30778718 | 30778967 |
| chr13 | 30905760 | 30906009 |
| chr13 | 31011560 | 31011809 |
| chr13 | 31089936 | 31090185 |
| chr13 | 31227324 | 31227573 |
| chr13 | 31430437 | 31430686 |
| chr13 | 31575060 | 31575309 |
| chr13 | 31641685 | 31641934 |
| chr13 | 31718167 | 31718416 |
| chr13 | 31723797 | 31724044 |
| chr13 | 32249897 | 32250146 |
| chr13 | 32296888 | 32297137 |
| chr13 | 32311823 | 32312072 |
| chr13 | 32316395 | 32316644 |
| chr13 | 32321163 | 32321412 |
| chr13 | 32348262 | 32348511 |
| chr13 | 32565108 | 32565357 |
| chr13 | 32578964 | 32579213 |
| chr13 | 32584041 | 32584290 |
| chr13 | 32596887 | 32597136 |
| chr13 | 32651705 | 32651954 |
| chr13 | 32760468 | 32760717 |
| chr13 | 32829312 | 32829561 |
| chr13 | 32852622 | 32852871 |
| chr13 | 32872003 | 32872252 |
| chr13 | 33535420 | 33535669 |
| chr13 | 33634729 | 33634978 |
| chr13 | 33660366 | 33660615 |

Figure 2C

| chromosome | start | stop |
|---|---|---|
| chr13 | 33742309 | 33742558 |
| chr13 | 33760763 | 33761012 |
| chr13 | 33787480 | 33787729 |
| chr13 | 33803219 | 33803468 |
| chr13 | 33925858 | 33926107 |
| chr13 | 34286418 | 34286667 |
| chr13 | 34301780 | 34302029 |
| chr13 | 34380783 | 34381032 |
| chr13 | 35504924 | 35505173 |
| chr13 | 35532835 | 35533084 |
| chr13 | 35538772 | 35539021 |
| chr13 | 36233165 | 36233414 |
| chr13 | 36343466 | 36343715 |
| chr13 | 36348003 | 36348252 |
| chr13 | 36380590 | 36380839 |
| chr13 | 36386774 | 36387023 |
| chr13 | 36410707 | 36410956 |
| chr13 | 36427833 | 36428082 |
| chr13 | 36445018 | 36445267 |
| chr13 | 36451093 | 36451342 |
| chr13 | 36568336 | 36568585 |
| chr13 | 36576882 | 36577131 |
| chr13 | 36663599 | 36663848 |
| chr13 | 37595672 | 37595921 |
| chr13 | 38283224 | 38283473 |
| chr13 | 38320894 | 38321143 |
| chr13 | 38361974 | 38362223 |
| chr13 | 38380696 | 38380945 |
| chr13 | 38789453 | 38789702 |
| chr13 | 39009512 | 39009761 |
| chr13 | 39096011 | 39096260 |
| chr13 | 39202882 | 39203131 |

| chromosome | start | stop |
|---|---|---|
| chr13 | 39264689 | 39264941 |
| chr13 | 39265199 | 39265451 |
| chr13 | 39265501 | 39265748 |
| chr13 | 39266515 | 39266762 |
| chr13 | 39266915 | 39267157 |
| chr13 | 39322100 | 39322347 |
| chr13 | 39338010 | 39338257 |

| chromosome | start | stop |
|---|---|---|

Figure 2D

| chromosome | start | stop |
|---|---|---|
| chrX | 44004660 | 44004909 |
| chrX | 44005572 | 44005821 |
| chrX | 80622102 | 80622351 |
| chrX | 81576088 | 81576337 |
| chrX | 83458870 | 83459119 |
| chrX | 83461989 | 83462238 |
| chrX | 83972195 | 83972444 |
| chrX | 83973091 | 83973340 |
| chrX | 84308155 | 84308404 |
| chrX | 84412933 | 84413182 |
| chrX | 84530826 | 84531075 |
| chrX | 84531356 | 84531605 |
| chrX | 84561384 | 84561633 |
| chrX | 85583338 | 85583587 |
| chrX | 85584098 | 85584347 |
| chrX | 85643367 | 85643616 |
| chrX | 85643847 | 85644096 |
| chrX | 85644765 | 85645014 |
| chrX | 85682212 | 85682461 |
| chrX | 85715710 | 85715959 |
| chrX | 85764768 | 85765017 |
| chrX | 85988749 | 85988998 |
| chrX | 85989214 | 85989463 |
| chrX | 85997574 | 85997823 |
| chrX | 87225841 | 87226090 |
| chrX | 91517109 | 91517358 |
| chrX | 91517578 | 91517827 |
| chrX | 94601042 | 94601291 |
| chrX | 95282210 | 95282459 |
| chrX | 95700693 | 95700942 |
| chrX | 96016317 | 96016566 |
| chrX | 96474722 | 96474971 |

| chromosome | start | stop |
|---|---|---|
| chrX | 96475190 | 96475439 |
| chrX | 96522258 | 96522507 |
| chrX | 96685785 | 96686034 |
| chrX | 98226881 | 98227130 |
| chrX | 98227467 | 98227716 |
| chrX | 98314697 | 98314946 |
| chrX | 98331718 | 98331967 |
| chrX | 102986351 | 102986600 |
| chrX | 122117885 | 122118134 |
| chrX | 116461543 | 116461792 |
| chrX | 116746667 | 116746916 |
| chrX | 117121287 | 117121536 |
| chrX | 117494627 | 117494876 |
| chrX | 118400460 | 118400709 |
| chrX | 119760145 | 119760394 |
| chrX | 120436725 | 120436974 |
| chrX | 120437307 | 120437556 |
| chrX | 121854317 | 121854566 |
| chrX | 121855104 | 121855353 |
| chrX | 122863038 | 122863287 |
| chrX | 123203756 | 123204005 |
| chrX | 123989030 | 123989279 |
| chrX | 124394967 | 124395216 |
| chrX | 125455385 | 125455634 |
| chrX | 125500101 | 125500350 |
| chrX | 125500582 | 125500831 |
| chrX | 127973758 | 127974007 |
| chrX | 128274367 | 128274616 |
| chrX | 128274689 | 128274938 |
| chrX | 128275238 | 128275487 |
| chrX | 128694864 | 128695113 |
| chrX | 131201343 | 131201592 |

| chromosome | start | stop |
|---|---|---|
| chrX | 132160888 | 132161137 |
| chrX | 133560531 | 133560780 |
| chrX | 133847304 | 133847553 |
| chrX | 133886077 | 133886326 |
| chrX | 133886778 | 133887027 |
| chrX | 135279738 | 135279987 |
| chrX | 135581031 | 135581280 |
| chrX | 136941543 | 136941792 |
| chrX | 138913313 | 138913562 |
| chrX | 138913920 | 138914169 |
| chrX | 139857034 | 139857283 |
| chrX | 139857318 | 139857567 |
| chrX | 141400062 | 141400311 |
| chrX | 141408144 | 141408393 |
| chrX | 141408548 | 141408797 |
| chrX | 142517923 | 142518172 |
| chrX | 143466384 | 143466633 |
| chrX | 147766073 | 147766322 |
| chrX | 147869477 | 147869726 |
| chrX | 147880766 | 147881015 |
| chrX | 147881811 | 147882060 |
| chrX | 151796091 | 151796340 |
| chrX | 104102171 | 104102420 |
| chrX | 104124449 | 104124698 |
| chrX | 104234605 | 104234854 |
| chrX | 104235195 | 104235444 |
| chrX | 104291380 | 104291629 |
| chrX | 104291786 | 104292035 |
| chrX | 104647680 | 104647929 |
| chrX | 104648691 | 104648940 |
| chrX | 106886942 | 106887191 |
| chrX | 3343487 | 3343736 |

Figure 2E

| chromosome | start | stop |
| --- | --- | --- |
| chrX | 4013011 | 4013260 |
| chrX | 5008870 | 5009119 |
| chrX | 5687782 | 5688031 |
| chrX | 5717003 | 5717252 |
| chrX | 5808998 | 5809247 |
| chrX | 5814187 | 5814436 |
| chrX | 5836574 | 5836823 |
| chrX | 5849776 | 5850025 |
| chrX | 6895474 | 6895723 |
| chrX | 6965226 | 6965475 |
| chrX | 6965573 | 6965822 |
| chrX | 7152743 | 7152992 |
| chrX | 9529739 | 9529988 |
| chrX | 9605323 | 9605572 |
| chrX | 9615158 | 9615407 |
| chrX | 9766329 | 9766578 |
| chrX | 9793372 | 9793621 |
| chrX | 9849298 | 9849547 |
| chrX | 9850182 | 9850431 |
| chrX | 10002581 | 10002830 |
| chrX | 10301512 | 10301761 |
| chrX | 10354762 | 10355011 |
| chrX | 10375361 | 10375610 |
| chrX | 10384260 | 10384509 |
| chrX | 10398645 | 10398894 |
| chrX | 10572719 | 10572968 |
| chrX | 10579800 | 10580049 |
| chrX | 10580482 | 10580731 |
| chrX | 10627502 | 10627751 |
| chrX | 10645064 | 10645313 |
| chrX | 10669664 | 10669913 |
| chrX | 10709674 | 10709923 |

| chromosome | start | stop |
| --- | --- | --- |
| chrX | 10710087 | 10710336 |
| chrX | 11139863 | 11140112 |
| chrX | 11658912 | 11659161 |
| chrX | 11681358 | 11681607 |
| chrX | 11686196 | 11686445 |
| chrX | 11686913 | 11687162 |
| chrX | 11687182 | 11687431 |
| chrX | 11917847 | 11918096 |
| chrX | 12016474 | 12016723 |
| chrX | 12158815 | 12159064 |
| chrX | 12485152 | 12485401 |
| chrX | 12608017 | 12608266 |
| chrX | 12724960 | 12725209 |
| chrX | 12841791 | 12842040 |
| chrX | 12904558 | 12904807 |
| chrX | 12937788 | 12938037 |
| chrX | 12938100 | 12938349 |
| chrX | 12992266 | 12992515 |
| chrX | 12995926 | 12996175 |
| chrX | 12997273 | 12997522 |
| chrX | 13293562 | 13293811 |
| chrX | 13338207 | 13338456 |
| chrX | 13340422 | 13340671 |
| chrX | 13351532 | 13351781 |
| chrX | 13624857 | 13625106 |
| chrX | 15525635 | 15525884 |
| chrX | 15543469 | 15543718 |
| chrX | 15543853 | 15544102 |
| chrX | 15844810 | 15845059 |
| chrX | 16860721 | 16860970 |
| chrX | 16861729 | 16861978 |
| chrX | 18307677 | 18307926 |

| chromosome | start | stop |
| --- | --- | --- |
| chrX | 18600682 | 18600931 |
| chrX | 19376384 | 19376633 |
| chrX | 20026004 | 20026253 |
| chrX | 20627108 | 20627357 |
| chrX | 21537202 | 21537451 |
| chrX | 21629967 | 21630216 |
| chrX | 21887062 | 21887311 |
| chrX | 22202443 | 22202692 |
| chrX | 23018625 | 23018874 |
| chrX | 23019006 | 23019255 |
| chrX | 24521525 | 24521774 |
| chrX | 24522047 | 24522296 |
| chrX | 25401534 | 25401783 |
| chrX | 25403300 | 25403549 |
| chrX | 28689766 | 28690015 |
| chrX | 28693600 | 28693849 |
| chrX | 28717026 | 28717275 |
| chrX | 28720131 | 28720380 |
| chrX | 28808128 | 28808377 |
| chrX | 28824813 | 28825062 |
| chrX | 28825844 | 28826093 |
| chrX | 29487025 | 29487274 |
| chrX | 30847194 | 30847443 |
| chrX | 32660941 | 32661190 |
| chrX | 32949975 | 32950224 |
| chrX | 35971182 | 35971431 |
| chrX | 35971544 | 35971793 |
| chrX | 43599991 | 43600240 |
| chrX | 43600262 | 43600511 |
| chrX | 43807492 | 43807741 |
| chrX | 63137429 | 63137678 |
| chrX | 63137928 | 63138177 |

Figure 2F

| chromosome | start | stop |
|---|---|---|
| chrX | 74269728 | 74269977 |
| chrX | 74270926 | 74271175 |
| chrX | 74282022 | 74282271 |
| chrX | 74329664 | 74329913 |
| chrX | 74344769 | 74345018 |
| chrX | 74741441 | 74741690 |
| chrX | 76192017 | 76192266 |
| chrX | 76194203 | 76194452 |
| chrX | 76221949 | 76222198 |
| chrX | 76226569 | 76226818 |
| chrX | 76234682 | 76234931 |
| chrX | 76308591 | 76308840 |
| chrX | 76647025 | 76647274 |
| chrX | 76711476 | 76711725 |
| chrX | 76759387 | 76759636 |
| chrX | 76778190 | 76778439 |
| chrX | 76778847 | 76779096 |
| chrX | 76875971 | 76876220 |
| chrX | 76923678 | 76923927 |
| chrX | 76937441 | 76937690 |
| chrX | 76938848 | 76939097 |
| chrX | 76939481 | 76939730 |
| chrX | 76949897 | 76950146 |
| chrX | 76951314 | 76951563 |
| chrX | 77040328 | 77040577 |
| chrX | 77168344 | 77168593 |
| chrX | 77634270 | 77634519 |
| chrX | 78176076 | 78176325 |
| chrX | 78176555 | 78176804 |
| chrX | 78178901 | 78179150 |
| chrX | 78208245 | 78208494 |
| chrX | 78290291 | 78290540 |

| chromosome | start | stop |
|---|---|---|
| chrX | 78401753 | 78402002 |
| chrX | 78403248 | 78403497 |
| chrX | 78405536 | 78405785 |
| chrX | 78411791 | 78412040 |
| chrX | 78427326 | 78427575 |
| chrX | 78430991 | 78431240 |
| chrX | 78431372 | 78431621 |
| chrX | 78437851 | 78438100 |
| chrX | 78526539 | 78526788 |
| chrX | 78531686 | 78531935 |
| chrX | 78996675 | 78996924 |
| chrX | 107682036 | 107682285 |
| chrX | 107683930 | 107684179 |
| chrX | 110366745 | 110366994 |
| chrX | 110367927 | 110368176 |
| chrX | 110368330 | 110368579 |
| chrX | 110443307 | 110443556 |
| chrX | 110466084 | 110466333 |
| chrX | 110537791 | 110538040 |
| chrX | 110538060 | 110538309 |
| chrX | 110538444 | 110538693 |
| chrX | 110575740 | 110575989 |
| chrX | 110576099 | 110576348 |
| chrX | 110950649 | 110950898 |
| chrX | 110971144 | 110971393 |
| chrX | 121597454 | 121597703 |
| chrX | 135558463 | 135558712 |
| chrX | 135570815 | 135571064 |
| chrX | 135760826 | 135761075 |
| chrX | 135831981 | 135832230 |
| chrX | 136044394 | 136044643 |
| chrX | 136318161 | 136318410 |

| chromosome | start | stop |
|---|---|---|
| chrX | 136320360 | 136320609 |
| chrX | 139380500 | 139380749 |
| chrX | 139381074 | 139381323 |
| chrX | 144897923 | 144898172 |
| chrX | 144908837 | 144909086 |
| chrX | 144958353 | 144958602 |
| chrX | 144959377 | 144959626 |
| chrX | 145799354 | 145799603 |
| chrX | 145922717 | 145922966 |
| chrX | 146994477 | 146994726 |
| chrX | 146995311 | 146995560 |
| chrX | 147540977 | 147541226 |
| chrX | 149764787 | 149765036 |
| chrX | 150808513 | 150808762 |
| chrX | 150809248 | 150809497 |
| chrX | 150942801 | 150943050 |
| chrX | 79712826 | 79713075 |
| chrX | 80374192 | 80374441 |
| chrX | 80491243 | 80491492 |
| chrX | 80514786 | 80515035 |
| chrX | 80553311 | 80553560 |
| chrX | 104028154 | 104028403 |
| chrX | 104039199 | 104039448 |
| chrX | 104101675 | 104101924 |

Figure 2G

| chromosome | start | stop |
|---|---|---|
| chr21 | 17021878 | 17022127 |
| chr21 | 17046718 | 17046967 |
| chr21 | 17088576 | 17088825 |
| chr21 | 17134784 | 17135033 |
| chr21 | 17161709 | 17161958 |
| chr21 | 17183683 | 17183932 |
| chr21 | 17301983 | 17302232 |
| chr21 | 17302814 | 17303063 |
| chr21 | 17336649 | 17336898 |
| chr21 | 17346228 | 17346477 |
| chr21 | 17348050 | 17348299 |
| chr21 | 17351309 | 17351558 |
| chr21 | 17362239 | 17362488 |
| chr21 | 17367713 | 17367962 |
| chr21 | 17506670 | 17506919 |
| chr21 | 17548792 | 17549041 |
| chr21 | 17591325 | 17591574 |
| chr21 | 17695933 | 17696182 |
| chr21 | 19087043 | 19087292 |
| chr21 | 19178365 | 19178614 |
| chr21 | 22579319 | 22579568 |
| chr21 | 22605212 | 22605461 |
| chr21 | 22964667 | 22964916 |
| chr21 | 22984832 | 22985081 |
| chr21 | 22985386 | 22985635 |
| chr21 | 36076596 | 36076845 |
| chr21 | 36169368 | 36169617 |
| chr21 | 36789088 | 36789337 |
| chr21 | 37939587 | 37939836 |
| chr21 | 37959766 | 37960015 |
| chr21 | 37983316 | 37983565 |
| chr21 | 38559539 | 38559788 |

| chromosome | start | stop |
|---|---|---|
| chr21 | 38751525 | 38751774 |
| chr21 | 39173262 | 39173511 |
| chr21 | 39285267 | 39285516 |
| chr21 | 39330340 | 39330589 |
| chr21 | 39442392 | 39442641 |
| chr21 | 39499219 | 39499468 |
| chr21 | 39541298 | 39541547 |
| chr21 | 39563720 | 39563969 |
| chr21 | 39584873 | 39585122 |
| chr21 | 46530377 | 46530731 |
| chr21 | 46534043 | 46534292 |
| chr21 | 46535763 | 46536012 |
| chr21 | 46537454 | 46537703 |
| chr21 | 46542089 | 46542338 |
| chr21 | 46556856 | 46557105 |
| chr21 | 46564465 | 46564714 |
| chr21 | 46567255 | 46567504 |
| chr21 | 46572969 | 46573218 |
| chr21 | 46605329 | 46605578 |
| chr21 | 32134809 | 32135058 |
| chr21 | 32148136 | 32148385 |
| chr21 | 32165994 | 32166243 |
| chr21 | 32174173 | 32174422 |
| chr21 | 32179882 | 32180131 |
| chr21 | 32181384 | 32181633 |
| chr21 | 32184463 | 32184712 |
| chr21 | 32201994 | 32202243 |
| chr21 | 32208609 | 32208858 |
| chr21 | 32319600 | 32319849 |
| chr21 | 35034581 | 35034830 |
| chr21 | 35060177 | 35060426 |
| chr21 | 35070605 | 35070854 |

| chromosome | start | stop |
|---|---|---|
| chr21 | 35093305 | 35093554 |
| chr21 | 35094930 | 35095179 |
| chr21 | 35099418 | 35099667 |
| chr21 | 35138457 | 35138706 |
| chr21 | 35152877 | 35153126 |
| chr21 | 35157173 | 35157422 |
| chr21 | 35161795 | 35162044 |
| chr21 | 35296082 | 35296331 |
| chr21 | 35450331 | 35450580 |
| chr21 | 35473022 | 35473271 |
| chr21 | 35473971 | 35474220 |
| chr21 | 35498164 | 35498413 |
| chr21 | 35540943 | 35541192 |
| chr21 | 35702965 | 35703214 |
| chr21 | 28574819 | 28575068 |
| chr21 | 28586377 | 28586626 |
| chr21 | 28597009 | 28597258 |
| chr21 | 28616121 | 28616370 |
| chr21 | 28631408 | 28631657 |
| chr21 | 28891355 | 28891604 |
| chr21 | 28892223 | 28892472 |
| chr21 | 28919446 | 28919695 |
| chr21 | 29012106 | 29012355 |
| chr21 | 29021007 | 29021256 |
| chr21 | 29753618 | 29753867 |
| chr21 | 29796479 | 29796728 |
| chr21 | 29812165 | 29812414 |
| chr21 | 29813966 | 29814215 |
| chr21 | 29814951 | 29815200 |
| chr21 | 29820028 | 29820277 |
| chr21 | 29825992 | 29826241 |
| chr21 | 29827616 | 29827865 |

Figure 2H

| chromosome | start | stop |
|---|---|---|
| chr21 | 29841662 | 29841911 |
| chr21 | 29884231 | 29884480 |
| chr21 | 29898255 | 29898504 |
| chr21 | 30368230 | 30368479 |
| chr21 | 30413906 | 30414155 |
| chr21 | 30415555 | 30415804 |
| chr21 | 30428953 | 30429202 |
| chr21 | 30477650 | 30477899 |
| chr21 | 30528161 | 30528410 |
| chr21 | 30550132 | 30550381 |
| chr21 | 30580738 | 30580987 |
| chr21 | 30600446 | 30600695 |
| chr21 | 30628668 | 30628917 |
| chr21 | 30660609 | 30660858 |
| chr21 | 30680391 | 30680640 |
| chr21 | 30720214 | 30720463 |
| chr21 | 30782462 | 30782711 |
| chr21 | 30810199 | 30810448 |
| chr21 | 30849402 | 30849651 |
| chr21 | 30868525 | 30868774 |
| chr21 | 30988776 | 30989025 |
| chr21 | 31012406 | 31012655 |
| chr21 | 31032720 | 31032969 |
| chr21 | 31085356 | 31085605 |
| chr21 | 31494755 | 31495004 |
| chr21 | 31560667 | 31560916 |
| chr21 | 31605973 | 31606222 |
| chr21 | 31621826 | 31622075 |
| chr21 | 31653822 | 31654071 |
| chr21 | 31670830 | 31671079 |
| chr21 | 31691347 | 31691596 |
| chr21 | 31708936 | 31709185 |

| chromosome | start | stop |
|---|---|---|
| chr21 | 31733443 | 31733692 |
| chr21 | 31768996 | 31769245 |
| chr21 | 31886189 | 31886438 |
| chr21 | 31886808 | 31887057 |
| chr21 | 32119833 | 32120082 |
| chr21 | 32125263 | 32125512 |
| chr21 | 25795207 | 25795456 |
| chr21 | 25802273 | 25802522 |
| chr21 | 26355452 | 26355702 |
| chr21 | 26365770 | 26366019 |
| chr21 | 26373440 | 26373689 |
| chr21 | 26374774 | 26375023 |
| chr21 | 26390279 | 26390528 |
| chr21 | 26390951 | 26391200 |
| chr21 | 26402802 | 26403051 |
| chr21 | 26496769 | 26497018 |
| chr21 | 26515400 | 26515649 |
| chr21 | 26571662 | 26571911 |
| chr21 | 26589786 | 26590035 |
| chr21 | 26604824 | 26605073 |
| chr21 | 26933670 | 26933919 |
| chr21 | 26950703 | 26950952 |
| chr21 | 27045134 | 27045383 |
| chr21 | 27398390 | 27398639 |
| chr21 | 27441346 | 27441595 |
| chr21 | 27465490 | 27465739 |
| chr21 | 27485182 | 27485431 |
| chr21 | 27486006 | 27486255 |
| chr21 | 27502429 | 27502678 |
| chr21 | 27520192 | 27520441 |
| chr21 | 27539803 | 27540052 |
| chr21 | 27623130 | 27623379 |

| chromosome | start | stop |
|---|---|---|
| chr21 | 27623692 | 27623941 |
| chr21 | 27763679 | 27763928 |
| chr21 | 27894000 | 27894249 |
| chr21 | 27926498 | 27926747 |
| chr21 | 28077177 | 28077426 |
| chr21 | 28122462 | 28122711 |
| chr21 | 28161337 | 28161586 |
| chr21 | 28180925 | 28181174 |
| chr21 | 28275754 | 28276003 |
| chr21 | 28291449 | 28291698 |
| chr21 | 28294820 | 28295069 |
| chr21 | 28295351 | 28295600 |
| chr21 | 28295857 | 28296106 |
| chr21 | 28311866 | 28312115 |
| chr21 | 28334784 | 28335033 |
| chr21 | 28354814 | 28355063 |
| chr21 | 28415341 | 28415590 |
| chr21 | 28433186 | 28433435 |
| chr21 | 28450226 | 28450475 |
| chr21 | 28474083 | 28474332 |
| chr21 | 28491062 | 28491311 |
| chr21 | 28509439 | 28509688 |
| chr21 | 28534176 | 28534425 |
| chr21 | 40042441 | 40042690 |
| chr21 | 40427338 | 40427587 |
| chr21 | 40509976 | 40510225 |
| chr21 | 40531291 | 40531540 |
| chr21 | 40578323 | 40578572 |
| chr21 | 40601158 | 40601407 |
| chr21 | 40630577 | 40630826 |
| chr21 | 41280723 | 41280972 |
| chr21 | 41607273 | 41607522 |

Figure 2I

| chromosome | start | stop |
|---|---|---|
| chr21 | 41629820 | 41630069 |
| chr21 | 41703462 | 41703711 |
| chr21 | 41729089 | 41729338 |
| chr21 | 41761636 | 41761885 |
| chr21 | 41839021 | 41839270 |
| chr21 | 41908902 | 41909151 |
| chr21 | 41933321 | 41933570 |
| chr21 | 41981868 | 41982117 |
| chr21 | 42029142 | 42029391 |
| chr21 | 42030642 | 42030891 |
| chr21 | 42080190 | 42080439 |
| chr21 | 42251219 | 42251468 |
| chr21 | 42559559 | 42559808 |
| chr21 | 42601828 | 42602077 |
| chr21 | 42851340 | 42851589 |
| chr21 | 42872713 | 42872962 |
| chr21 | 43032728 | 43032977 |
| chr21 | 43406661 | 43406910 |
| chr21 | 46521300 | 46521549 |
| chr21 | 16323548 | 16323797 |
| chr21 | 16330249 | 16330498 |
| chr21 | 16332622 | 16332871 |
| chr21 | 16333315 | 16333564 |
| chr21 | 16335355 | 16335604 |
| chr21 | 16344361 | 16344610 |
| chr21 | 16349606 | 16349855 |
| chr21 | 16358650 | 16358899 |
| chr21 | 15713251 | 15713500 |
| chr21 | 15714357 | 15714606 |
| chr21 | 15725977 | 15726226 |
| chr21 | 15731366 | 15731615 |
| chr21 | 15816232 | 15816481 |

| chromosome | start | stop |
|---|---|---|
| chr21 | 15843963 | 15844212 |
| chr21 | 15858450 | 15858699 |
| chr21 | 15859015 | 15859264 |
| chr21 | 16002625 | 16002874 |
| chr21 | 16030414 | 16030663 |
| chr21 | 16063119 | 16063368 |
| chr21 | 16068358 | 16068607 |
| chr21 | 16071495 | 16071744 |
| chr21 | 16081282 | 16081531 |
| chr21 | 16115078 | 16115327 |
| chr21 | 16122085 | 16122334 |
| chr21 | 16130688 | 16130937 |
| chr21 | 16133865 | 16134114 |
| chr21 | 16139969 | 16140218 |
| chr21 | 16141592 | 16141841 |
| chr21 | 16160517 | 16160766 |
| chr21 | 16165861 | 16166110 |
| chr21 | 16189746 | 16189995 |
| chr21 | 16190806 | 16191055 |
| chr21 | 16192618 | 16192867 |
| chr21 | 16195809 | 16196058 |
| chr21 | 16198337 | 16198586 |
| chr21 | 16203731 | 16203980 |
| chr21 | 16207035 | 16207284 |
| chr21 | 16209341 | 16209590 |
| chr21 | 16211270 | 16211519 |
| chr21 | 16219907 | 16220156 |
| chr21 | 16230785 | 16231034 |
| chr21 | 16236026 | 16236275 |
| chr21 | 16241139 | 16241388 |
| chr21 | 16242812 | 16243061 |
| chr21 | 16246944 | 16247193 |

| chromosome | start | stop |
|---|---|---|
| chr21 | 16265484 | 16265733 |
| chr21 | 16273734 | 16273983 |
| chr21 | 16275865 | 16276114 |
| chr21 | 16290234 | 16290483 |
| chr21 | 16295877 | 16296126 |
| chr21 | 16296687 | 16296936 |
| chr21 | 16298842 | 16299091 |
| chr21 | 16316213 | 16316462 |
| chr21 | 16319836 | 16320085 |

Figure 2J

| chromosome | start | stop |
|---|---|---|
| chr18 | 64634331 | 64634580 |
| chr18 | 64645925 | 64646174 |
| chr18 | 64975938 | 64976187 |
| chr18 | 64996573 | 64996822 |
| chr18 | 65066425 | 65066674 |
| chr18 | 65073729 | 65073978 |
| chr18 | 65074170 | 65074419 |
| chr18 | 66343957 | 66344206 |
| chr18 | 66344406 | 66344655 |
| chr18 | 66585247 | 66585496 |
| chr18 | 66596489 | 66596738 |
| chr18 | 66601231 | 66601480 |
| chr18 | 69966208 | 69966457 |
| chr18 | 70088939 | 70089188 |
| chr18 | 70093364 | 70093613 |
| chr18 | 70107935 | 70108184 |
| chr18 | 70198868 | 70199117 |
| chr18 | 70200128 | 70200377 |
| chr18 | 70200907 | 70201156 |
| chr18 | 70674976 | 70675225 |
| chr18 | 70682967 | 70683216 |
| chr18 | 73541191 | 73541440 |
| chr18 | 73548315 | 73548564 |
| chr18 | 73605288 | 73605537 |
| chr18 | 73704485 | 73704734 |
| chr18 | 73752546 | 73752795 |
| chr18 | 73764755 | 73765004 |
| chr18 | 73768420 | 73768669 |
| chr18 | 73775027 | 73775276 |
| chr18 | 73788751 | 73789000 |
| chr18 | 73851108 | 73851357 |
| chr18 | 73854713 | 73854962 |

| chromosome | start | stop |
|---|---|---|
| chr18 | 73871422 | 73871671 |
| chr18 | 73876103 | 73876352 |
| chr18 | 73879805 | 73880054 |
| chr18 | 73884248 | 73884497 |
| chr18 | 73931865 | 73932114 |
| chr18 | 73938014 | 73938263 |
| chr18 | 73943212 | 73943461 |
| chr18 | 73947628 | 73947877 |
| chr18 | 73964168 | 73964417 |
| chr18 | 73966321 | 73966570 |
| chr18 | 73974071 | 73974320 |
| chr18 | 73985549 | 73985798 |
| chr18 | 73987174 | 73987423 |
| chr18 | 48466086 | 48466335 |
| chr18 | 48928528 | 48928777 |
| chr18 | 48929078 | 48929327 |
| chr18 | 48951524 | 48951773 |
| chr18 | 48951856 | 48952105 |
| chr18 | 48959882 | 48960131 |
| chr18 | 48960304 | 48960553 |
| chr18 | 49004516 | 49004765 |
| chr18 | 49006425 | 49006674 |
| chr18 | 49017695 | 49017944 |
| chr18 | 49148010 | 49148259 |
| chr18 | 49149627 | 49149876 |
| chr18 | 49149933 | 49150182 |
| chr18 | 49150459 | 49150708 |
| chr18 | 50239403 | 50239652 |
| chr18 | 50242789 | 50243038 |
| chr18 | 50243069 | 50243318 |
| chr18 | 50243367 | 50243616 |
| chr18 | 50247229 | 50247478 |

| chromosome | start | stop |
|---|---|---|
| chr18 | 50308727 | 50308976 |
| chr18 | 50309031 | 50309280 |
| chr18 | 50338747 | 50338996 |
| chr18 | 50423284 | 50423533 |
| chr18 | 50424422 | 50424671 |
| chr18 | 50424789 | 50425038 |
| chr18 | 50448837 | 50449086 |
| chr18 | 50449492 | 50449741 |
| chr18 | 50514079 | 50514328 |
| chr18 | 50519889 | 50520138 |
| chr18 | 56064244 | 56064493 |
| chr18 | 56148666 | 56148915 |
| chr18 | 56149037 | 56149286 |
| chr18 | 56244171 | 56244420 |
| chr18 | 56245242 | 56245491 |
| chr18 | 56247063 | 56247312 |
| chr18 | 56527049 | 56527298 |
| chr18 | 56528011 | 56528260 |
| chr18 | 56532190 | 56532439 |
| chr18 | 56532882 | 56533131 |
| chr18 | 56534208 | 56534457 |
| chr18 | 56601487 | 56601736 |
| chr18 | 56633131 | 56633380 |
| chr18 | 56635259 | 56635508 |
| chr18 | 56719296 | 56719545 |
| chr18 | 58037828 | 58038077 |
| chr18 | 58038328 | 58038577 |
| chr18 | 58039111 | 58039360 |
| chr18 | 58040290 | 58040539 |
| chr18 | 59424085 | 59424334 |
| chr18 | 59424765 | 59425014 |
| chr18 | 59441324 | 59441573 |

Figure 2K

| chromosome | start | stop |
|---|---|---|
| chr18 | 59499718 | 59499967 |
| chr18 | 59500226 | 59500475 |
| chr18 | 59507920 | 59508169 |
| chr18 | 59543044 | 59543293 |
| chr18 | 59556453 | 59556702 |
| chr18 | 59614976 | 59615225 |
| chr18 | 59625553 | 59625802 |
| chr18 | 59631090 | 59631339 |
| chr18 | 59631779 | 59632028 |
| chr18 | 59632388 | 59632637 |
| chr18 | 59695718 | 59695967 |
| chr18 | 59696087 | 59696336 |
| chr18 | 59696563 | 59696812 |
| chr18 | 59712419 | 59712668 |
| chr18 | 59756979 | 59757228 |
| chr18 | 59770789 | 59771038 |
| chr18 | 59805993 | 59806242 |
| chr18 | 59813876 | 59814125 |
| chr18 | 59855411 | 59855660 |
| chr18 | 59909054 | 59909303 |
| chr18 | 59909336 | 59909585 |
| chr18 | 59910140 | 59910389 |
| chr18 | 59910602 | 59910851 |
| chr18 | 59973803 | 59974052 |
| chr18 | 59996728 | 59996977 |
| chr18 | 60010541 | 60010790 |
| chr18 | 60011381 | 60011630 |
| chr18 | 60240694 | 60240943 |
| chr18 | 60378353 | 60378602 |
| chr18 | 60384593 | 60384842 |
| chr18 | 60384979 | 60385228 |
| chr18 | 60389544 | 60389793 |

| chromosome | start | stop |
|---|---|---|
| chr18 | 60401084 | 60401333 |
| chr18 | 60412199 | 60412448 |
| chr18 | 60420053 | 60420302 |
| chr18 | 60434561 | 60434810 |
| chr18 | 60449047 | 60449296 |
| chr18 | 60452471 | 60452720 |
| chr18 | 60456757 | 60457006 |
| chr18 | 60467147 | 60467396 |
| chr18 | 60469757 | 60470006 |
| chr18 | 60514168 | 60514417 |
| chr18 | 60537888 | 60538137 |
| chr18 | 60544380 | 60544629 |
| chr18 | 60544742 | 60544991 |
| chr18 | 60545407 | 60545656 |
| chr18 | 60611934 | 60612183 |
| chr18 | 60617081 | 60617330 |
| chr18 | 60617641 | 60617890 |
| chr18 | 60630438 | 60630687 |
| chr18 | 60630849 | 60631098 |
| chr18 | 60639840 | 60640089 |
| chr18 | 60640300 | 60640549 |
| chr18 | 60776944 | 60777193 |
| chr18 | 60813738 | 60813987 |
| chr18 | 60814585 | 60814834 |
| chr18 | 60938666 | 60938915 |
| chr18 | 60939202 | 60939451 |
| chr18 | 60950541 | 60950790 |
| chr18 | 60953225 | 60953474 |
| chr18 | 60958474 | 60958723 |
| chr18 | 60960879 | 60961128 |
| chr18 | 60965583 | 60965832 |
| chr18 | 60970051 | 60970300 |

| chromosome | start | stop |
|---|---|---|
| chr18 | 60974839 | 60975088 |
| chr18 | 60984378 | 60984627 |
| chr18 | 61055997 | 61056246 |
| chr18 | 61088669 | 61088918 |
| chr18 | 61090462 | 61090711 |
| chr18 | 61100325 | 61100574 |
| chr18 | 61154459 | 61154708 |
| chr18 | 61162901 | 61163150 |
| chr18 | 61170629 | 61170878 |
| chr18 | 61197492 | 61197741 |
| chr18 | 61213452 | 61213701 |
| chr18 | 61213900 | 61214149 |
| chr18 | 61216749 | 61216998 |
| chr18 | 61232928 | 61233177 |
| chr18 | 61236079 | 61236328 |
| chr18 | 61253277 | 61253526 |
| chr18 | 61259478 | 61259727 |
| chr18 | 61264533 | 61264782 |
| chr18 | 61289440 | 61289689 |
| chr18 | 61368889 | 61369138 |
| chr18 | 61370663 | 61370912 |
| chr18 | 63685629 | 63685878 |
| chr18 | 63711583 | 63711832 |
| chr18 | 63721183 | 63721432 |
| chr18 | 64379625 | 64379874 |
| chr18 | 64398368 | 64398617 |
| chr18 | 64410092 | 64410341 |
| chr18 | 64412606 | 64412855 |
| chr18 | 64417267 | 64417516 |
| chr18 | 64421562 | 64421811 |
| chr18 | 64426871 | 64427120 |
| chr18 | 64436287 | 64436536 |

Figure 2L

| chromosome | start | stop |
| --- | --- | --- |
| chr18 | 64593727 | 64593976 |
| chr18 | 24962594 | 24962843 |
| chr18 | 24964748 | 24964997 |
| chr18 | 25003553 | 25003802 |
| chr18 | 25033345 | 25033594 |
| chr18 | 25037434 | 25037683 |
| chr18 | 25052992 | 25053241 |
| chr18 | 25080042 | 25080291 |
| chr18 | 25124915 | 25125164 |
| chr18 | 25128057 | 25128306 |
| chr18 | 25140257 | 25140506 |
| chr18 | 25140722 | 25140971 |
| chr18 | 25147759 | 25148008 |
| chr18 | 25157828 | 25158077 |
| chr18 | 25160244 | 25160493 |
| chr18 | 25166354 | 25166603 |
| chr18 | 25172986 | 25173235 |
| chr18 | 25174972 | 25175221 |
| chr18 | 25175640 | 25175889 |
| chr18 | 25182855 | 25183104 |
| chr18 | 25198531 | 25198780 |
| chr18 | 25201886 | 25202135 |
| chr18 | 25209395 | 25209644 |
| chr18 | 25213880 | 25214129 |
| chr18 | 25216888 | 25217137 |
| chr18 | 25228617 | 25228866 |
| chr18 | 25231535 | 25231784 |
| chr18 | 25245662 | 25245911 |
| chr18 | 25246300 | 25246549 |
| chr18 | 25254843 | 25255092 |
| chr18 | 25265476 | 25265725 |
| chr18 | 25278532 | 25278781 |

| chromosome | start | stop |
| --- | --- | --- |
| chr18 | 25279010 | 25279259 |
| chr18 | 25283817 | 25284066 |
| chr18 | 25292042 | 25292291 |
| chr18 | 25295429 | 25295678 |
| chr18 | 25330345 | 25330594 |
| chr18 | 25332963 | 25333212 |
| chr18 | 25333284 | 25333533 |
| chr18 | 25345252 | 25345501 |
| chr18 | 25384702 | 25384951 |
| chr18 | 25510767 | 25511016 |
| chr18 | 25519108 | 25519357 |
| chr18 | 25531724 | 25531973 |
| chr18 | 25543168 | 25543417 |
| chr18 | 25547425 | 25547674 |
| chr18 | 25557343 | 25557592 |
| chr18 | 25564483 | 25564732 |
| chr18 | 25583087 | 25583336 |
| chr18 | 25585083 | 25585332 |
| chr18 | 25589902 | 25590151 |
| chr18 | 25601966 | 25602215 |
| chr18 | 25611986 | 25612235 |
| chr18 | 25617498 | 25617747 |
| chr18 | 25629105 | 25629354 |
| chr18 | 25631180 | 25631429 |
| chr18 | 25643639 | 25643888 |
| chr18 | 25645371 | 25645620 |
| chr18 | 25665025 | 25665274 |
| chr18 | 25666614 | 25666863 |
| chr18 | 25667057 | 25667306 |
| chr18 | 25670741 | 25670990 |
| chr18 | 25673208 | 25673457 |
| chr18 | 25681018 | 25681267 |

| chromosome | start | stop |
| --- | --- | --- |
| chr18 | 25682079 | 25682328 |
| chr18 | 25689906 | 25690155 |
| chr18 | 25700540 | 25700789 |
| chr18 | 25703648 | 25703897 |
| chr18 | 25707188 | 25707437 |
| chr18 | 25716100 | 25716349 |
| chr18 | 25722951 | 25723200 |
| chr18 | 25725055 | 25725304 |
| chr18 | 25748105 | 25748354 |
| chr18 | 26214441 | 26214690 |
| chr18 | 26236788 | 26237037 |
| chr18 | 26261336 | 26261585 |
| chr18 | 26265937 | 26266186 |
| chr18 | 26285286 | 26285535 |
| chr18 | 26289006 | 26289255 |
| chr18 | 26308405 | 26308654 |
| chr18 | 26308962 | 26309211 |
| chr18 | 26312054 | 26312303 |
| chr18 | 26316149 | 26316398 |
| chr18 | 47100905 | 47101154 |
| chr18 | 47130278 | 47130527 |
| chr18 | 47366936 | 47367185 |
| chr18 | 47371131 | 47371380 |
| chr18 | 47689868 | 47690117 |
| chr18 | 47690267 | 47690516 |
| chr18 | 47703689 | 47703938 |
| chr18 | 47708139 | 47708388 |
| chr18 | 47717445 | 47717694 |
| chr18 | 47738531 | 47738780 |
| chr18 | 47777438 | 47777687 |
| chr18 | 47794212 | 47794461 |
| chr18 | 47799400 | 47799649 |

Figure 2M

| chromosome | start | stop |
|---|---|---|
| chr18 | 47802662 | 47802911 |
| chr18 | 39874986 | 39875235 |
| chr18 | 39891490 | 39891739 |
| chr18 | 42204240 | 42204489 |
| chr18 | 42313146 | 42313395 |
| chr18 | 42313939 | 42314188 |
| chr18 | 42314302 | 42314551 |
| chr18 | 42349923 | 42350172 |
| chr18 | 42407165 | 42407414 |
| chr18 | 42418033 | 42418282 |
| chr18 | 42449702 | 42449951 |
| chr18 | 42450400 | 42450649 |
| chr18 | 42461427 | 42461676 |
| chr18 | 42462834 | 42463083 |
| chr18 | 42468595 | 42468844 |
| chr18 | 42468938 | 42469187 |
| chr18 | 42644003 | 42644252 |
| chr18 | 42644494 | 42644743 |
| chr18 | 42645387 | 42645636 |
| chr18 | 42741059 | 42741308 |
| chr18 | 42745733 | 42745982 |
| chr18 | 42746460 | 42746709 |
| chr18 | 42746911 | 42747160 |
| chr18 | 42747473 | 42747722 |
| chr18 | 43796659 | 43796908 |
| chr18 | 43820471 | 43820720 |
| chr18 | 43841913 | 43842162 |
| chr18 | 43842202 | 43842451 |
| chr18 | 43842647 | 43842896 |
| chr18 | 43845701 | 43845950 |
| chr18 | 43846353 | 43846602 |
| chr18 | 43917652 | 43917901 |

| chromosome | start | stop |
|---|---|---|
| chr18 | 43918519 | 43918768 |
| chr18 | 43918998 | 43919247 |
| chr18 | 43919544 | 43919793 |
| chr18 | 44086123 | 44086372 |
| chr18 | 44094299 | 44094548 |
| chr18 | 44167214 | 44167463 |
| chr18 | 44167791 | 44168040 |
| chr18 | 44168296 | 44168545 |
| chr18 | 44173512 | 44173761 |
| chr18 | 44174626 | 44174875 |
| chr18 | 44857765 | 44858014 |
| chr18 | 45110525 | 45110774 |
| chr18 | 45197621 | 45197870 |
| chr18 | 45197871 | 45198120 |
| chr18 | 45198760 | 45199009 |
| chr18 | 45234886 | 45235135 |
| chr18 | 45235523 | 45235772 |
| chr18 | 45238370 | 45238619 |
| chr18 | 45335896 | 45336145 |
| chr18 | 45336353 | 45336602 |
| chr18 | 45357461 | 45357710 |
| chr18 | 45357745 | 45357994 |
| chr18 | 45358502 | 45358751 |
| chr18 | 45362379 | 45362628 |
| chr18 | 45397588 | 45397837 |
| chr18 | 45864183 | 45864432 |
| chr18 | 46464382 | 46464631 |
| chr18 | 46473428 | 46473677 |
| chr18 | 46474545 | 46474794 |
| chr18 | 46481797 | 46482046 |
| chr18 | 46483016 | 46483265 |
| chr18 | 46589014 | 46589263 |

| chromosome | start | stop |
|---|---|---|
| chr18 | 46599847 | 46600096 |
| chr18 | 46601866 | 46602115 |
| chr18 | 46983278 | 46983527 |
| chr18 | 47013103 | 47013352 |
| chr18 | 47016802 | 47017051 |
| chr18 | 286722 | 286971 |
| chr18 | 298393 | 298642 |
| chr18 | 338127 | 338376 |
| chr18 | 340427 | 340676 |
| chr18 | 387135 | 387384 |
| chr18 | 391175 | 391424 |
| chr18 | 434440 | 434689 |
| chr18 | 457527 | 457776 |
| chr18 | 460384 | 460633 |
| chr18 | 469281 | 469530 |
| chr18 | 572716 | 572965 |
| chr18 | 598352 | 598601 |
| chr18 | 615413 | 615662 |
| chr18 | 618280 | 618529 |
| chr18 | 901111 | 901360 |
| chr18 | 939383 | 939632 |
| chr18 | 26321283 | 26321532 |
| chr18 | 26337865 | 26338114 |
| chr18 | 26345717 | 26345966 |
| chr18 | 26365387 | 26365636 |
| chr18 | 26367518 | 26367767 |
| chr18 | 26392500 | 26392749 |
| chr18 | 26406499 | 26406748 |
| chr18 | 26711590 | 26711839 |
| chr18 | 26729342 | 26729591 |
| chr18 | 26733981 | 26734230 |
| chr18 | 26739336 | 26739585 |

Figure 2N

| chromosome | start | stop |
|---|---|---|
| chr18 | 26750685 | 26750934 |
| chr18 | 26752487 | 26752736 |
| chr18 | 26757573 | 26757822 |
| chr18 | 27244230 | 27244479 |
| chr18 | 35076347 | 35076596 |
| chr18 | 35147912 | 35148161 |
| chr18 | 35282655 | 35282904 |
| chr18 | 35292141 | 35292390 |
| chr18 | 35304247 | 35304496 |
| chr18 | 35311302 | 35311551 |
| chr18 | 36463709 | 36463958 |
| chr18 | 36473033 | 36473282 |
| chr18 | 36475403 | 36475652 |
| chr18 | 36479145 | 36479394 |
| chr18 | 36482038 | 36482287 |
| chr18 | 36483959 | 36484208 |
| chr18 | 36485761 | 36486010 |
| chr18 | 36487627 | 36487876 |
| chr18 | 36489135 | 36489384 |
| chr18 | 36631244 | 36631493 |
| chr18 | 36654006 | 36654255 |
| chr18 | 36658050 | 36658299 |
| chr18 | 36569619 | 36569868 |
| chr18 | 1017928 | 1018177 |
| chr18 | 241538 | 241787 |
| chr18 | 242831 | 243080 |

Figure 2O

| chromosome | start | stop |
| --- | --- | --- |
| chr13 | 19520254 | 19520499 |
| chr13 | 19523790 | 19524042 |
| chr13 | 20531155 | 20531403 |
| chr13 | 20542998 | 20543246 |
| chr13 | 21182580 | 21182828 |
| chr13 | 22255353 | 22255601 |
| chr13 | 26795002 | 26795250 |
| chr13 | 26795380 | 26795628 |
| chr13 | 26809864 | 26810112 |
| chr13 | 26810422 | 26810669 |
| chr13 | 26810951 | 26811198 |
| chr13 | 26811424 | 26811674 |
| chr13 | 26820545 | 26820794 |
| chr13 | 26824800 | 26825048 |
| chr13 | 26825155 | 26825405 |
| chr13 | 26827150 | 26827400 |
| chr13 | 26827690 | 26827939 |
| chr13 | 26829149 | 26829396 |
| chr13 | 26829663 | 26829911 |
| chr13 | 26830241 | 26830491 |
| chr13 | 26830739 | 26830987 |
| chr13 | 26834633 | 26834880 |
| chr13 | 26836514 | 26836761 |
| chr13 | 26843066 | 26843315 |
| chr13 | 26851259 | 26851507 |
| chr13 | 26864367 | 26864615 |
| chr13 | 26888243 | 26888485 |
| chr13 | 26888660 | 26888907 |
| chr13 | 26898691 | 26898936 |
| chr13 | 26925436 | 26925684 |
| chr13 | 26926976 | 26927224 |
| chr13 | 26938928 | 26939175 |

| chromosome | start | stop |
| --- | --- | --- |
| chr13 | 26939424 | 26939672 |
| chr13 | 26939942 | 26940196 |
| chr13 | 26952790 | 26953038 |
| chr13 | 26956549 | 26956797 |
| chr13 | 26957204 | 26957453 |
| chr13 | 26957736 | 26957984 |
| chr13 | 26971501 | 26971749 |
| chr13 | 26974853 | 26975100 |
| chr13 | 26976810 | 26977059 |
| chr13 | 27117460 | 27117707 |
| chr13 | 27216274 | 27216526 |
| chr13 | 29111011 | 29111260 |
| chr13 | 29233772 | 29234021 |
| chr13 | 29310139 | 29310388 |
| chr13 | 29563140 | 29563389 |
| chr13 | 31499212 | 31499458 |
| chr13 | 31499519 | 31499772 |
| chr13 | 31609109 | 31609361 |
| chr13 | 31653571 | 31653822 |
| chr13 | 32149129 | 32149380 |
| chr13 | 32169142 | 32169392 |
| chr13 | 32173373 | 32173622 |
| chr13 | 32271292 | 32271539 |
| chr13 | 32316109 | 32316362 |
| chr13 | 32316651 | 32316898 |
| chr13 | 32339360 | 32339608 |
| chr13 | 32359633 | 32359883 |
| chr13 | 32433382 | 32433629 |
| chr13 | 32434990 | 32435237 |
| chr13 | 32600409 | 32600659 |
| chr13 | 32653613 | 32653857 |
| chr13 | 32758635 | 32758877 |

| chromosome | start | stop |
| --- | --- | --- |
| chr13 | 32759010 | 32759261 |
| chr13 | 32784101 | 32784351 |
| chr13 | 32784570 | 32784820 |
| chr13 | 32786822 | 32787069 |
| chr13 | 32787129 | 32787381 |
| chr13 | 32811213 | 32811463 |
| chr13 | 32931779 | 32932029 |
| chr13 | 33016510 | 33016761 |
| chr13 | 33016929 | 33017182 |
| chr13 | 33017432 | 33017681 |
| chr13 | 36342494 | 36342743 |
| chr13 | 36343935 | 36344179 |
| chr13 | 36344330 | 36344577 |
| chr13 | 36345572 | 36345822 |
| chr13 | 36346001 | 36346253 |
| chr13 | 36349204 | 36349453 |
| chr13 | 36354263 | 36354513 |
| chr13 | 36358322 | 36358572 |
| chr13 | 36361603 | 36361850 |
| chr13 | 36362050 | 36362297 |
| chr13 | 36362531 | 36362778 |
| chr13 | 36363439 | 36363689 |
| chr13 | 36366103 | 36366353 |
| chr13 | 36387184 | 36387431 |
| chr13 | 39584383 | 39584630 |
| chr13 | 39585052 | 39585299 |
| chr13 | 39585675 | 39585922 |
| chr13 | 40090054 | 40090298 |
| chr13 | 40093695 | 40093942 |
| chr13 | 40098460 | 40098707 |
| chr13 | 40098913 | 40099157 |
| chr13 | 40101053 | 40101303 |

Figure 2P

| chromosome | start | stop |
|---|---|---|
| chr13 | 40101582 | 40101832 |
| chr13 | 40384942 | 40385189 |
| chr13 | 40391440 | 40391687 |
| chr13 | 40392221 | 40392468 |
| chr13 | 40398309 | 40398557 |
| chr13 | 40398589 | 40398840 |
| chr13 | 40406460 | 40406711 |
| chr13 | 40420794 | 40421037 |
| chr13 | 40613790 | 40614037 |
| chr13 | 42846940 | 42847187 |
| chr13 | 42876485 | 42876732 |
| chr13 | 42896653 | 42896897 |
| chr13 | 43149529 | 43149781 |
| chr13 | 43164772 | 43165022 |
| chr13 | 43177841 | 43178091 |
| chr13 | 52163649 | 52163899 |
| chr13 | 52541402 | 52541652 |
| chr13 | 52549279 | 52549529 |
| chr13 | 53323273 | 53323520 |
| chr13 | 53350485 | 53350727 |
| chr13 | 53505942 | 53506191 |
| chr13 | 53555869 | 53556121 |
| chr13 | 53606740 | 53606987 |
| chr13 | 53610142 | 53610389 |
| chr13 | 53619813 | 53620063 |
| chr13 | 53622959 | 53623209 |
| chr13 | 59239399 | 59239649 |
| chr13 | 62064603 | 62064852 |
| chr13 | 68236363 | 68236610 |
| chr13 | 68238595 | 68238842 |
| chr13 | 68241140 | 68241393 |
| chr13 | 68310701 | 68310948 |

| chromosome | start | stop |
|---|---|---|
| chr13 | 68311152 | 68311402 |
| chr13 | 68316131 | 68316378 |
| chr13 | 68428699 | 68428952 |
| chr13 | 68429013 | 68429258 |
| chr13 | 68570544 | 68570791 |
| chr13 | 71269531 | 71269778 |
| chr13 | 71454173 | 71454420 |
| chr13 | 71456180 | 71456429 |
| chr13 | 71463069 | 71463321 |
| chr13 | 71464644 | 71464887 |
| chr13 | 71465060 | 71465307 |
| chr13 | 71466315 | 71466560 |
| chr13 | 71466724 | 71466967 |
| chr13 | 71479089 | 71479339 |
| chr13 | 71479359 | 71479608 |
| chr13 | 71619104 | 71619349 |
| chr13 | 71750165 | 71750409 |
| chr13 | 71750461 | 71750708 |
| chr13 | 71762243 | 71762493 |
| chr13 | 71762640 | 71762893 |
| chr13 | 71781780 | 71782031 |
| chr13 | 71783224 | 71783469 |
| chr13 | 71784572 | 71784822 |
| chr13 | 73226435 | 73226679 |
| chr13 | 73233924 | 73234168 |
| chr13 | 73251601 | 73251851 |
| chr13 | 73261064 | 73261309 |
| chr13 | 73284370 | 73284617 |
| chr13 | 73296842 | 73297089 |
| chr13 | 73305479 | 73305731 |
| chr13 | 73305843 | 73306093 |
| chr13 | 73309111 | 73309357 |

| chromosome | start | stop |
|---|---|---|
| chr13 | 73320095 | 73320339 |
| chr13 | 77198180 | 77198433 |
| chr13 | 77422635 | 77422880 |
| chr13 | 77449372 | 77449622 |
| chr13 | 77454212 | 77454458 |
| chr13 | 77454985 | 77455228 |
| chr13 | 77455721 | 77455971 |
| chr13 | 77456394 | 77456643 |
| chr13 | 77476090 | 77476339 |
| chr13 | 77477580 | 77477833 |
| chr13 | 77513439 | 77513692 |
| chr13 | 77591495 | 77591742 |
| chr13 | 77595913 | 77596160 |
| chr13 | 77598010 | 77598257 |
| chr13 | 77630724 | 77630968 |
| chr13 | 77633431 | 77633680 |
| chr13 | 77636364 | 77636611 |
| chr13 | 77639621 | 77639873 |
| chr13 | 77642789 | 77643041 |
| chr13 | 77652265 | 77652509 |
| chr13 | 77652705 | 77652952 |
| chr13 | 77675169 | 77675423 |
| chr13 | 77699605 | 77699849 |
| chr13 | 77713099 | 77713352 |
| chr13 | 77714235 | 77714481 |
| chr13 | 77742675 | 77742920 |
| chr13 | 77759281 | 77759528 |
| chr13 | 78540689 | 78540943 |
| chr13 | 89222075 | 89222318 |
| chr13 | 94063232 | 94063481 |

Figure 2Q

| chromosome | start | stop |
|---|---|---|
| chr18 | 11701840 | 11702094 |
| chr18 | 11742882 | 11743124 |
| chr18 | 11743713 | 11743964 |
| chr18 | 11743974 | 11744216 |
| chr18 | 11745797 | 11746044 |
| chr18 | 11766505 | 11766752 |
| chr18 | 11784594 | 11784841 |
| chr18 | 11784857 | 11785107 |
| chr18 | 11789414 | 11789659 |
| chr18 | 11791405 | 11791649 |
| chr18 | 11831898 | 11832147 |
| chr18 | 11840071 | 11840318 |
| chr18 | 11853018 | 11853271 |
| chr18 | 12786330 | 12786572 |
| chr18 | 12793790 | 12794034 |
| chr18 | 12813342 | 12813590 |
| chr18 | 12813796 | 12814046 |
| chr18 | 12836508 | 12836756 |
| chr18 | 12837826 | 12838071 |
| chr18 | 12839370 | 12839619 |
| chr18 | 12839810 | 12840054 |
| chr18 | 12840789 | 12841033 |
| chr18 | 12955546 | 12955788 |
| chr18 | 12968393 | 12968643 |
| chr18 | 12984202 | 12984449 |
| chr18 | 12984953 | 12985198 |
| chr18 | 12986018 | 12986263 |
| chr18 | 13007427 | 13007681 |
| chr18 | 13007815 | 13008064 |
| chr18 | 13019314 | 13019562 |
| chr18 | 13029804 | 13030046 |
| chr18 | 13036834 | 13037081 |

| chromosome | start | stop |
|---|---|---|
| chr18 | 13040411 | 13040657 |
| chr18 | 13049051 | 13049304 |
| chr18 | 13053013 | 13053260 |
| chr18 | 13057128 | 13057370 |
| chr18 | 13725324 | 13725566 |
| chr18 | 13731669 | 13731919 |
| chr18 | 13930816 | 13931068 |
| chr18 | 13936510 | 13936761 |
| chr18 | 13939030 | 13939277 |
| chr18 | 13941500 | 13941742 |
| chr18 | 18709626 | 18709868 |
| chr18 | 19345013 | 19345263 |
| chr18 | 22314388 | 22314639 |
| chr18 | 22317204 | 22317445 |
| chr18 | 22318584 | 22318826 |
| chr18 | 22474179 | 22474425 |
| chr18 | 22503094 | 22503336 |
| chr18 | 22514422 | 22514675 |
| chr18 | 22527670 | 22527920 |
| chr18 | 22713619 | 22713863 |
| chr18 | 22715692 | 22715939 |
| chr18 | 22746015 | 22746258 |
| chr18 | 22751334 | 22751581 |
| chr18 | 26362055 | 26362304 |
| chr18 | 27204825 | 27205070 |
| chr18 | 27683185 | 27683429 |
| chr18 | 28529366 | 28529610 |
| chr18 | 28538550 | 28538803 |
| chr18 | 28550611 | 28550855 |
| chr18 | 28551683 | 28551928 |
| chr18 | 28584849 | 28585102 |
| chr18 | 29704799 | 29705048 |

| chromosome | start | stop |
|---|---|---|
| chr18 | 29705097 | 29705347 |
| chr18 | 29707000 | 29707248 |
| chr18 | 29711514 | 29711758 |
| chr18 | 29772771 | 29773020 |
| chr18 | 29773038 | 29773291 |
| chr18 | 29790110 | 29790357 |
| chr18 | 29794196 | 29794446 |
| chr18 | 29814455 | 29814703 |
| chr18 | 29816677 | 29816924 |
| chr18 | 29824628 | 29824872 |
| chr18 | 29941738 | 29941986 |
| chr18 | 29942404 | 29942657 |
| chr18 | 29947043 | 29947286 |
| chr18 | 29963606 | 29963859 |
| chr18 | 29967321 | 29967565 |
| chr18 | 29988241 | 29988491 |
| chr18 | 29989060 | 29989304 |
| chr18 | 33702205 | 33702458 |
| chr18 | 33703293 | 33703541 |
| chr18 | 33703805 | 33704052 |
| chr18 | 33710269 | 33710511 |
| chr18 | 33881399 | 33881647 |
| chr18 | 33884883 | 33885133 |
| chr18 | 33965911 | 33966161 |
| chr18 | 33967910 | 33968160 |
| chr18 | 35703018 | 35703269 |
| chr18 | 35705739 | 35705986 |
| chr18 | 36487627 | 36487876 |
| chr18 | 52428207 | 52428460 |
| chr18 | 52472800 | 52473050 |
| chr18 | 52702246 | 52702490 |
| chr18 | 52703207 | 52703449 |

Figure 2R

| chromosome | start | stop |
|---|---|---|
| chr18 | 52719979 | 52720226 |
| chr18 | 53843255 | 53843507 |
| chr18 | 53843510 | 53843764 |
| chr18 | 53843879 | 53844121 |
| chr18 | 53870090 | 53870332 |
| chr18 | 53873286 | 53873528 |
| chr18 | 53913040 | 53913287 |
| chr18 | 54141132 | 54141379 |
| chr18 | 54154870 | 54155117 |
| chr18 | 54183137 | 54183381 |
| chr18 | 54271758 | 54272011 |
| chr18 | 54352988 | 54353238 |
| chr18 | 60378353 | 60378602 |
| chr18 | 61164144 | 61164393 |

| chromosome | start | stop |
|---|---|---|

| chromosome | start | stop |
|---|---|---|

Figure 2S

| chromosome | start | stop |
|---|---|---|
| chr21 | 15774354 | 15774598 |
| chr21 | 15774701 | 15774951 |
| chr21 | 15941894 | 15942144 |
| chr21 | 15942369 | 15942621 |
| chr21 | 16330536 | 16330783 |
| chr21 | 16331481 | 16331728 |
| chr21 | 16332238 | 16332485 |
| chr21 | 16333694 | 16333941 |
| chr21 | 16335023 | 16335271 |
| chr21 | 16336651 | 16336901 |
| chr21 | 16337562 | 16337816 |
| chr21 | 16338381 | 16338633 |
| chr21 | 16338902 | 16339154 |
| chr21 | 16339772 | 16340019 |
| chr21 | 16340409 | 16340656 |
| chr21 | 16344080 | 16344330 |
| chr21 | 16349101 | 16349354 |
| chr21 | 16362700 | 16362954 |
| chr21 | 16375294 | 16375539 |
| chr21 | 16376059 | 16376308 |
| chr21 | 16376695 | 16376942 |
| chr21 | 16519760 | 16520004 |
| chr21 | 16529308 | 16529552 |
| chr21 | 16529940 | 16530189 |
| chr21 | 16531755 | 16532002 |
| chr21 | 16533111 | 16533355 |
| chr21 | 16537385 | 16537631 |
| chr21 | 16545527 | 16545774 |
| chr21 | 16788480 | 16788722 |
| chr21 | 16792457 | 16792708 |
| chr21 | 17149630 | 17149877 |
| chr21 | 45114956 | 45115203 |

| chromosome | start | stop |
|---|---|---|
| chr21 | 17160410 | 17160656 |
| chr21 | 17160972 | 17161216 |
| chr21 | 19300496 | 19300748 |
| chr21 | 19396568 | 19396818 |
| chr21 | 25701930 | 25702183 |
| chr21 | 25702313 | 25702560 |
| chr21 | 27985131 | 27985378 |
| chr21 | 27989556 | 27989803 |
| chr21 | 28000089 | 28000336 |
| chr21 | 28007209 | 28007456 |
| chr21 | 28007550 | 28007793 |
| chr21 | 28008308 | 28008555 |
| chr21 | 28054591 | 28054835 |
| chr21 | 28292245 | 28292493 |
| chr21 | 28294400 | 28294644 |
| chr21 | 28308980 | 28309224 |
| chr21 | 28311566 | 28311813 |
| chr21 | 28316801 | 28317045 |
| chr21 | 29796060 | 29796309 |
| chr21 | 30112410 | 30112660 |
| chr21 | 30112772 | 30113024 |
| chr21 | 30113106 | 30113350 |
| chr21 | 30114870 | 30115119 |
| chr21 | 30301073 | 30301322 |
| chr21 | 30301466 | 30301713 |
| chr21 | 30317970 | 30318220 |
| chr21 | 30358601 | 30358851 |
| chr21 | 30397555 | 30397801 |
| chr21 | 30419470 | 30419720 |
| chr21 | 30527461 | 30527714 |
| chr21 | 30528513 | 30528763 |
| chr21 | 30554566 | 30554808 |

| chromosome | start | stop |
|---|---|---|
| chr21 | 30568450 | 30568700 |
| chr21 | 30901196 | 30901442 |
| chr21 | 30950156 | 30950403 |
| chr21 | 30950626 | 30950878 |
| chr21 | 30952977 | 30953227 |
| chr21 | 30953281 | 30953523 |
| chr21 | 30953836 | 30954083 |
| chr21 | 30966825 | 30967077 |
| chr21 | 30968330 | 30968574 |
| chr21 | 30969659 | 30969903 |
| chr21 | 31015490 | 31015733 |
| chr21 | 31022236 | 31022488 |
| chr21 | 31091818 | 31092065 |
| chr21 | 31109787 | 31110039 |
| chr21 | 31110149 | 31110396 |
| chr21 | 31113996 | 31114249 |
| chr21 | 31120815 | 31121064 |
| chr21 | 31144588 | 31144835 |
| chr21 | 35154438 | 35154687 |
| chr21 | 40549354 | 40549598 |
| chr21 | 40759240 | 40759493 |
| chr21 | 40839325 | 40839569 |
| chr21 | 40846844 | 40847093 |
| chr21 | 41160090 | 41160343 |
| chr21 | 41171755 | 41171999 |
| chr21 | 41298214 | 41298467 |
| chr21 | 41592339 | 41592583 |
| chr21 | 41596188 | 41596432 |
| chr21 | 41741900 | 41742144 |
| chr21 | 43219112 | 43219356 |
| chr21 | 46468654 | 46468898 |
| chr21 | 46495701 | 46495954 |

Figure 2T

| chromosome | start | stop |
|---|---|---|
| chr2 | 50176039 | 50176288 |
| chr2 | 63596895 | 63597144 |
| chr2 | 103538910 | 103539159 |

| chromosome | start | stop |
|---|---|---|

| chromosome | start | stop |
|---|---|---|

Figure 2V

| chromosome | start | stop |
|---|---|---|
| chr4 | 21947614 | 21947863 |
| chr4 | 62556697 | 62556946 |
| chr4 | 72418734 | 72418983 |
| chr4 | 122570216 | 122570465 |
| chr4 | 130264593 | 130264842 |

Figure 2X

| chromosome | start | stop |
|---|---|---|
| chr5 | 59283789 | 59284038 |
| chr5 | 88597843 | 88598092 |
| chr5 | 163891445 | 163891694 |
| chr5 | 163896919 | 163897168 |

| chromosome | start | stop |
|---|---|---|

| chromosome | start | stop |
|---|---|---|

Figure 2Y

| chromosome | start | stop |
|---|---|---|
| chr6 | 8529895 | 8530144 |
| chr6 | 96221217 | 96221466 |
| chr6 | 112441026 | 112441275 |
| chr6 | 118481182 | 118481431 |
| chr6 | 129800139 | 129800388 |

Figure 2Z

| chromosome | start | stop |
|---|---|---|
| chr7 | 22725339 | 22725588 |
| chr7 | 42250786 | 42251035 |

| chromosome | start | stop |
|---|---|---|

| chromosome | start | stop |
|---|---|---|

Figure 2AA

| chromosome | start | stop |
|---|---|---|
| chr9 | 2600491 | 2600740 |
| chr9 | 14299731 | 14299980 |
| chr9 | 72782230 | 72782479 |
| chr9 | 82880926 | 82881175 |

| chromosome | start | stop |
|---|---|---|

| chromosome | start | stop |
|---|---|---|

Figure 2AB

MULTIPLEXED PARALLEL ANALYSIS OF TARGETED GENOMIC REGIONS FOR NON-INVASIVE PRENATAL TESTING

CROSS-REFERENCE TO RELATED APPLICATIONS

The present application is a continuation of U.S. application Ser. No. 15/160,981, filed May 20, 2016, which claims the benefit of priority of U.S. Provisional Application No. 62/263,320 (filed Dec. 4, 2015) and U.S. Provisional Application No. 62/165,593 (filed May 22, 2015), which are incorporated herein by reference in their entireties.

STATEMENT REGARDING SEQUENCE LISTING

The instant application contains a Sequence Listing which has been submitted electronically in ASCII format and is hereby incorporated by reference in its entirety. Said ASCII copy, created Jul. 25, 2016, is named "CIQ-0009_ST25.txt" and is 1,920 bytes in size.

BACKGROUND OF THE INVENTION

The discovery of free fetal DNA (ffDNA) in maternal circulation (Lo, Y. M. et al. (1997) *Lancet* 350:485-487) was a landmark towards the development of non-invasive prenatal testing for fetal aneuploidies and has opened up new possibilities in the clinical setting. ffDNA has been successfully used for the determination of fetal sex and fetal Rhesus D status in maternal plasma (see e.g., Bianchi, D. et al. (2005) *Obstet. Gynecol.* 106:841-844; Lo, Y. M. et al. (1998) *N. Engl. J. Med.* 339:1734-1738; U.S. Pat. No. 6,258,540; PCT Publication WO 91/07660). These methods have become routine tests in a number of diagnostic laboratories worldwide. However, direct analysis of the limited amount of ffDNA in the presence of an excess of maternal DNA is a great challenge for Non-Invasive Prenatal Testing (NIPT) assessment of fetal aneuploidies.

The percentage of ffDNA in the maternal circulation was originally estimated to be about 3-6% of the total DNA (Lo, Y. M. et al. (1998) *Am. J. Hum. Genet.* 62:768-775) However, recent studies suggest that fetal DNA can reach the amount of 10-20% of total DNA in the maternal circulation (Lun, F. M. et al. (2008) *Clin. Chem.* 54:1664-1672). In aneuploidies, one of the chromosomes is present with additional or fewer copies. For example in trisomy 21 cases, chromosome 21 is present in three copies instead of two. Therefore, the ability to distinguish normal cases from trisomy 21 cases depends on the ability to detect the extra copy of chromosome 21. However, the high levels of maternal DNA in the maternal circulation compared to the limited amount of fetal DNA further complicate quantification.

Over the last decade a large number of different methods have been applied towards the discrimination of ffDNA from circulating maternal DNA or towards ffDNA enrichment (Chan, K. C. et al. (2004) *Clin. Chem.* 50:88-92; Papageorgiou, E. A. et al. (2009) *Am. J. Pathol.* 174:1609-1618). These include DNA-based approaches, such as sequencing approaches (Chiu, R. W. et al. (2008) *Proc. Natl. Acad. Sci. USA* 105:20458-20463; Fan, H. C. et al. (2008) *Proc. Natl. Acad. Sci. USA* 105:16266-16271) or epigenetic based approaches which focus on the investigation of the methylation status of fetal DNA either using sodium bisulfite DNA treatment (Chim, S. S. et al. (205) *Proc. Natl. Acad. Sci. USA* 102:14753-14758; PCT Publication WO 2003/020974; PCT Publication WO 2005/028674), methylation-sensitive restriction enzymes (Old, R. W. et al. (2007) *Reprod. Biomed. Online* 15:227-235; PCT Publication WO 2005/035725) or antibodies specific to the 5-methylcytosine residues of CpG dinucleotides across the genome (Papageorgiou, E. A. et al. (2009)*Am. J. Pathol.* 174:1609-1618, Papageorgiou, E. A. et al. (2011) *Nature Medicine* 17:510-513; Tsaliki, E. et al. (2012) *Prenat. Diagn.* 32:996-1001; PCT Publication WO 2011/092592). Alternative approaches have targeted fetal-specific mRNA (Ng, E. K. et al. (2003) *Proc. Natl. Acad. Sci. USA* 100:4748-4753) or have focused on the investigation of fetal-specific proteins (Avent, N. D. et al. (2008) *Semin. Fetal Neonatal Med.* 13:91-98).

The implementation of next generation sequencing (NGS) technologies in the development of NIPT of aneuploidies has revolutionized the field. In 2008, two independent groups demonstrated that NIPT of trisomy 21 could be achieved using next generation massively parallel shotgun sequencing (MPSS) (Chiu, R. W. et al. (2008) *Proc. Natl. Acad. Sci. USA* 105:20458-20463; Fan, H. C. et al. (2008) *Proc. Natl. Acad. Sci. USA* 105:16266-162710). The new era of NIPT for aneuploidies has opened new possibilities for the implementation of these technologies into clinical practice. Biotechnology companies that are partly or wholly dedicated to the development of NIPT tests have initiated large scale clinical studies towards their implementation (Palomaki, G. E. et al. (2011) *Genet. Med.* 13:913-920; Ehrich, M. et al. (2011) *Am. J. Obstet. Gynecol.* 204:205e1-11; Chen, E. Z. et al. (2011) *PLoS One* 6:e21791; Sehnert, A. J. et al. (2011) *Clin. Chem.* 57:1042-1049; Palomaki, G. E. et al. (2012); *Genet. Med.* 14:296-305; Bianchi, D. W. et al. (2012) *Obstet. Gynecol.* 119:890-901; Zimmerman, B. et al. (2012) *Prenat. Diag.* 32:1233-1241; Nicolaides, K. H. et al. (2013) *Prenat. Diagn.* 33:575-579; Sparks, A. B. et al. (2012) *Prenat. Diagn.* 32:3-9). Currently four companies in the United States (SEQUENOM Inc., Verinata Health, Inc., Natera and Ariosa) are offering NIPT testing using next generation sequencing approaches.

Initial NIPT approaches used massively parallel shotgun sequencing (MPSS) NGS methodologies (see e.g., U.S. Pat. Nos. 7,888,017; 8,008,018; 8,195,415; 8,296,076; 8,682,594; US Patent Publication 20110201507; US Patent Publication 20120270739). Thus, these approaches are whole genome-based, in which the entire maternal sample containing both maternal DNA and free fetal DNA is subjected to amplification, sequencing and analysis.

More recently, targeted-based NGS approaches for NIPT, in which only specific sequences of interest are sequenced, have been developed. For example, a SNP-based NGS approach involving targeted amplification and analysis of SNPs on chromosomes 13, 18, 21, X and Y in a single reaction has been described (Zimmerman, B. et al. (2012) *Prenat. Diag.* 32:1233-1241; Nicolaides, K. H. et al. (2013) *Prenat. Diagn.* 33:575-579; PCT Publication WO 2011/041485; U.S. Pat. No. 8,825,412). Furthermore, an NGS-based approach has been developed in which only specific regions of interest are sequenced wherein three probes per targeted locus are hybridized to the complementary template. Once the three probes are hybridized they are ligated and form one continuous longer probe that is then amplified and sequenced (Sparks, A. B. et al. (2012) *Prenat. Diagn.* 32:3-9; US Patent Publication 20120034603). The samples are analyzed using a highly multiplexed assay termed Digital ANalysis of Selected Regions (DANSR). Such targeted approaches require significantly less sequencing than the MPSS approaches, since sequencing is only performed on specific loci on the chromosome of interest rather than across the whole genome.

Additional methodologies for NGS-based approaches to NIPT are still needed, in particular approaches that can target specific sequences of interest, thereby greatly reducing the amount of sequencing needed as compared to whole genome-based approaches.

SUMMARY OF THE INVENTION

The invention provides methods for non-invasive prenatal testing that allow for detecting risk of chromosomal abnormalities and utilizes a targeted approach to enrich for sequences of interest prior to massive parallel sequencing and a statistical analysis approach that allows for highly accurate counting and assessment of the chromosomal constituents of maternal plasma across regions of interest. Thus, the methods of the invention reduce the amount of sequencing needed for massive parallel sequencing, allow for high throughput application, with reduced cost and a very high degree of accuracy. The methods of the invention utilize a pool of TArget Capture Sequences (TACS) to enrich for sequences of interest in a mixed sample containing both maternal and fetal DNA. In particular, the pool of TACS is designed such that the sequences within the pool have features that optimize the efficiency, specificity and accuracy of the chromosomal abnormality assessment. More specifically, the size of the TACS, the number of TACS, their placement on the chromosome(s) of interest and their GC content all have been optimized. Hybridization of the TACS to a sequencing library prepared from a mixed sample of maternal and fetal DNA (e.g., a maternal plasma sample containing ffDNA), followed by isolation of the sequences within the library that bind to the TACS allows for enrichment of only those chromosomal regions of interest, prior to massive parallel sequencing and analysis.

Accordingly, in one aspect, the invention provides a method of testing for risk of a chromosomal abnormality in a chromosome of interest in fetal DNA in a mixed sample of maternal and fetal DNA, the method comprising:
  (a) preparing a sequencing library from the mixed sample;
  (b) hybridizing the sequencing library to a pool of TArget Capture Sequences (TACS), wherein the pool of TACS comprises sequences that bind to one or more chromosomes of interest and wherein:
    (i) each sequence within the pool is between 100-260 base pairs in length and/or 100-300 bp in length, and/or 100-350 bp in length, each sequence having a 5' end and a 3' end;
    (ii) each sequence within the pool binds to the chromosome(s) of interest at least 150 base pairs away, on both the 5' end and the 3' end, from regions harboring Copy Number Variations, Segmental duplications or repetitive DNA elements; and
    (iii) the GC content of the TACS is between 19%-50%, and/or 19-60%, and/or 19%-70% and/or 19%-80%;
  (c) isolating members of the sequencing library that bind to the TACS to obtain an enriched library;
  (d) amplifying and sequencing the enriched library; and
  (e) performing statistical analysis on the sequencing output of the enriched library sequences to thereby determine a risk of the chromosomal and/or other genetic abnormality in the fetal DNA.

In one embodiment, the chromosomal abnormality is an aneuploidy, such as a trisomy. The chromosome of interest can be any chromosome, although preferred chromosomes include chromosomes 13, 18, 21, X and Y. A preferred aneuploidy for detection is trisomy 21 (T21). In addition to numerical abnormalities such as aneuploidies, the invention allows for detection of other types of chromosomal abnormalities, such as structural abnormalities, including but not limited to copy number changes including, but not limited to, microdeletions and microduplications, insertions, translocations, inversions and small-size mutations including point mutations and mutational signatures In one embodiment, the pool of TACS is fixed to a solid support. For example, the TACS can be biotinylated and bound to streptavidin-coated magnetic beads. In another embodiment, the pool of TACS may be free-moving in solution.

In one embodiment, the TACS are designed to bind to a chromosome of interest and one or more reference sequences to detect risk of a chromosomal abnormality on the chromosome of interest. Alternatively, the pool of TACS can be designed to bind to multiple chromosomes of interest such that risk of multiple chromosomal abnormalities can be detected, as well as, for example, fetal gender, all within a single analysis of the sample. For example, in one embodiment, the pool of TACS comprises of different sequences that bind to chromosomes 13, 18, 21 and X, or to chromosomes 13, 18, 21, X and Y.

In various embodiments, the GC content of the TACS is, between 19% and 80%, between 19% and 70%, between 19% and 60%, between 19% and 50%, between 19% and 49%, between 19% and 48%, between 19% and 47%, between 19% and 46%, between 19% and 45%, between 19% and 44%, between 19% and 43%, between 19% and 42%, between 19% and 41% or between 19% and 40%.

In various embodiments, each sequence within the pool of TACS is between 100-350 base pairs, 150-260 base pairs, 100-200 base pairs or 200-260 base pairs in length. In one embodiment, each sequence within the pool of TACS is 250 base pairs in length.

In various embodiments, the pool of TACS can comprise 800 or more, 1500 or more distinct sequences, 2000 or more distinct sequences, 2500 or more distinct sequences, or 3000 or more distinct sequences. In one embodiment, the pool of TACS comprises 1600 distinct sequences.

In one embodiment, sequencing of the enriched library provides a read-depth for the loci found on the chromosome of interest and read-depths for reference loci and the statistical analysis is performed by applying an algorithm that tests sequentially the read-depth of the loci found on the chromosome of interest against the read-depth of the reference loci, whereby detected differences can indicate the presence of genetic variants. The algorithm steps can include, but are not limited to: (a) removal of inadequately sequenced loci; (b) GC-content bias alleviation; and (c) ploidy status classification. In one embodiment, GC-content bias is alleviated by grouping together loci of matching GC-content.

In another embodiment, sequencing of the enriched library provides the size of fragments of cell-free genetic material captured by TACS and the statistical analysis comprises use of an algorithm that compares and contrasts the distribution of fragment-sizes from test-loci and reference-loci, whereby differences in the distribution indicate the presence of genetic variants. The algorithm steps can include, but are not limited to: (a) removal of fragment-size outliers; (b) creation of a binary distribution of fragment-sizes; and (c) testing the binary distribution of fragment-sizes originating from the region of interest against the respective distribution of the reference loci in order to classify ploidy status.

Typically, ploidy status classification is achieved by application of one or more statistical methods. For example, the statistical method can be selected from the group consisting of a t-test, a bivariate nonparametric bootstrap test, a stratified permutation test and a binomial test of proportions and/or combinations thereof. In one embodiment, all four of the aforementioned statistical methods are applied to the sample. Typically, the statistical method results in a score value for the mixed sample and risk of the chromosomal abnormality in the fetal DNA is detected when the score value for the mixed sample is above a reference threshold value. The method of the invention can further comprise estimation of the fetal DNA fraction in the mixed sample.

In another embodiment, the statistical method can be selected from the group consisting of a t-test, a bivariate nonparametric bootstrap test and a stratified permutation test. In one embodiment, all of the aforementioned statistical methods are applied to the sample. Typically, the statistical method results in a score value for the mixed sample and risk of the chromosomal abnormality in the fetal DNA is detected when the score value for the mixed sample is above a reference threshold value. The method of the invention can further comprise estimation of the fetal DNA fraction in the mixed sample.

In another aspect, the invention provides kits for performing the method of the invention. In one embodiment, the kit comprises a container comprising the pool of TACS and instructions for performing the method. In various other embodiments, the kit comprises additional components for carrying out the other steps of the method.

DETAILED DESCRIPTION

Figure 1:
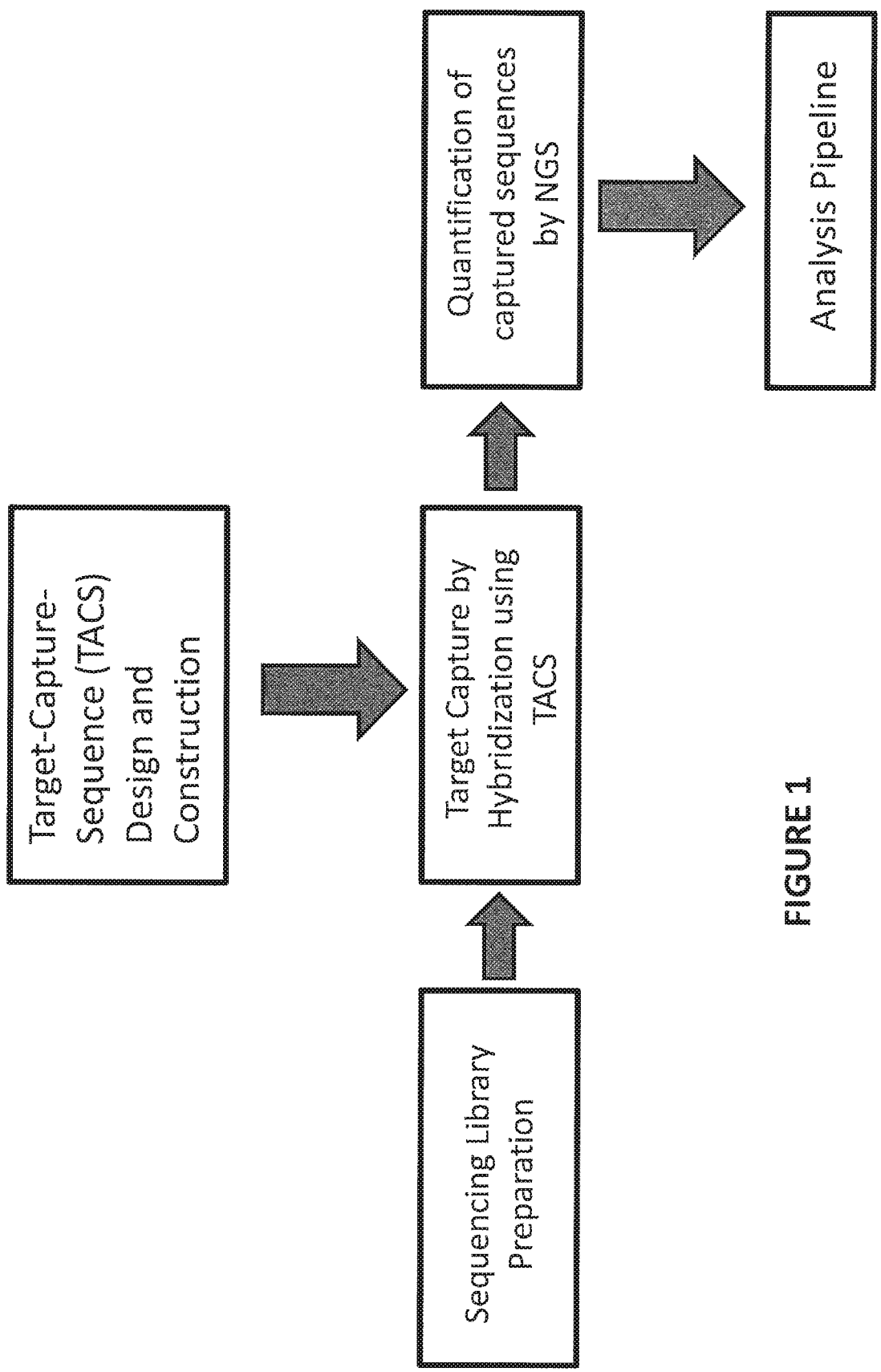
FIG. 1 is a schematic diagram of multiplexed parallel analysis of targeted genomic regions for non-invasive prenatal testing using TArget Capture Sequences (TACS).

The invention pertains to a NIPT method that involves hybridization-based enrichment of selected target regions across the human genome in a multiplexed panel assay, followed by quantification, coupled with a novel bioinformatics and mathematical analysis pipeline. In-solution hybridization enrichment has been used in the past to enrich specific regions of interest prior to sequencing (see e.g., Meyer, M and Kirchner, M. (2010) *Cold Spring Harb. Protoc.* 2010(6):pdbprot5448; Liao, G. J. et al. (2012) *PLoS One* 7:e38154; Maricic, T. et al. (2010) *PLoS One* 5:e14004; Tewhey, R. et al. (2009) *Genome Biol.* 10:R116; Tsangaras, K. et al. (2014) *PLoS One* 9:e109101). However, for the NIPT methods of the invention, the target sequences used to enrich for specific regions of interest relevant for detecting risk of a chromosomal abnormality have been optimized for maximum efficiency, specificity and accuracy. The human genome is full of elements that can confound and perplex any type of genetic analysis, thereby evidencing the benefit of a targeted approach for NIPT. Given this, the complexity of the human genome and the presence of these confounding elements, requires careful design of the target-capture sequences used for enrichment. As described herein, optimal TArget Capture Sequences (TACS) have now been designed that allow for simpler and more robust NIPT while minimizing the risks of false positive and false negative results, that are associated with whole genome NIPT tests due to inevitable sequencing of confounding elements.

The method of the invention for testing for risk of a chromosomal abnormality in a chromosome of interest in fetal DNA in a mixed sample of maternal and fetal DNA, comprises:

(a) preparing a sequencing library from the mixed sample;
(b) hybridizing the sequencing library to a pool of TArget Capture Sequences (TACS), wherein the pool of TACS comprises sequences that bind to one or more chromosomes of interest and wherein:
  (i) each sequence within the pool is between 100-260 base pairs in length, each sequence having a 5' end and a 3' end;
  (ii) each sequence within the pool binds to the chromosome(s) of interest at least 150 base pairs away, on both the 5' end and the 3' end, from regions harboring Copy Number Variations (CNVs), Segmental duplications or repetitive DNA elements; and (iii) the GC content of the TACS is between 19% and 50%;

(c) isolating members of the sequencing library that bind to the TACS to obtain an enriched library;

(d) amplifying and sequencing the enriched library; and (e) performing statistical analysis on the sequencing output of the enriched library sequences to thereby determine a risk of the chromosomal abnormality in the fetal DNA.

Kits for performing the method of the invention are also encompassed.

Various aspects of this disclosure are described in further detail in the following subsections.

TArget Capture Sequence Design

As used herein, the term "TArget Capture Sequences" or "TACS" refers to short DNA sequences that are complementary to the region(s) of interest on a chromosome(s) of interest and which are used as "bait" to capture and enrich the region of interest from a large library of sequences, such as a whole genomic sequencing library prepared from a maternal plasma sample. A pool of TACS is used for enrichment, wherein the sequences within the pool have been optimized with regard to: (i) the length of the sequences; (ii) the distribution of the TACS across the region(s) of interest; and (iii) the GC content of the TACS. The number of sequences within the TACS pool (pool size) has also been optimized.

It has been discovered that TACS having a length of 100-260 base pairs are optimal to maximize enrichment efficiency. In various other embodiments, each sequence within the pool of TACS is between 150-260 base pairs, 100-200 base pairs, 200-260 base pairs or 100-350 bp in length. In preferred embodiments, the length of the TACS within the pool is 250 or 260 base pairs. It will be appreciated by the ordinarily skilled artisan that a slight variation in TACS size typically can be used without altering the results (e.g., the addition or deletion of a few base pairs on either end of the TACS); accordingly, the base pair lengths given herein are to be considered "about" or "approximate", allowing for some slight variation (e.g., 1-5%) in length. Thus, for example, a length of "250 base pairs" is intended to refer to "about 250 base pairs" or "approximately 250 base pairs", such that, for example, 248 or 252 base pairs is also encompassed.

The distribution of the TACS across each region or chromosome of interest has been optimized to avoid high copy repeats, low copy repeats and copy number variants, while at the same time also being able to target informative single nucleotide polymorphisms (SNPs) in order to enable both aneuploidy, or structural copy number change detection, and fetal fraction (ff) estimation. Accordingly, each sequence within the TACS pool is designed such that the 5' end and the 3' end are each at least 150 base pairs away from regions in the genome that are known to harbour one or more of the following genomic elements: Copy Number Variations (CNVs), Segmental duplications and/or repetitive DNA elements (such as transposable elements or tandem repeat areas). In various other embodiments, each sequence within the TACS pool is designed such that the 5' end and the 3' end are each at least 200, 250, 300, 400 or 500 base pairs away from regions in the genome that are known to harbour one or more of the aforementioned elements.

The term "Copy Number Variations" is a term of art that refers to a form of structural variation in the human genome in which there can be alterations in the DNA of the genome in different individuals that can result in a fewer or greater than normal number of a section(s) of the genome in certain individuals. CNVs correspond to relatively large regions of the genome that may be deleted (e.g., a section that normally is A-B-C-D can be A-B-D) or may be duplicated (e.g., a section that normally is A-B-C-D can be A-B-C-C-D). CNVs account for roughly 13% of the human genome, with each variation ranging in size from about 1 kilobase to several megabases in size.

The term "Segmental duplications" (also known as "low-copy repeats") is also a term of art that refers to blocks of DNA that range from about 1 to 400 kilobases in length that occur at more than one site within the genome and typically share a high level (greater than 90%) of sequence identity. Segmental duplications are reviewed in, for example, Eichler. E. E. (2001) *Trends Genet.* 17:661-669.

The term "repetitive DNA elements" (also known as "repeat DNA" or "repeated DNA") is also a term of art that refers to patterns of DNA that occur in multiple copies throughout the genome. The term "repetitive DNA element" encompasses terminal repeats, tandem repeats and interspersed repeats, including transposable elements. Repetitive DNA elements in NGS is discussed further in, for example, Todd, J. et al. (2012) *Nature Reviews Genet.* 13:36-46.

The TACS are designed with specific GC content characteristics in order to minimize data GC bias and to allow a custom and innovative data analysis pipeline. It has been determined that TACS with a GC content of 19-50% achieve optimal enrichment and perform best with cell free fetal DNA. Within the pool of TACS, different sequences can have different % GC content, although to be selected for inclusion with the pool, the % GC content of each sequence is chosen as between 19-50%. In some instances, the pool of TACS may be chosen so as to define a different % GC content range, deemed to be more suitable for the assessment of specific genetic abnormalities. Non-limiting examples of various % GC content ranges, can be between 19% and 75%, 19% and 65%, between 19% and 55%, between 19 and 50%, between 19% and 49%, between 19% and 48%, between 19% and 47%, between 19% and 46%, between 19% and 45%, between 19% and 44%, between 19% and 43%, between 19% and 42%, between 19% and 41% or between 19% and 40%.

As described in further detail below with respect to one embodiment of the data analysis, following amplification and sequencing of the enriched sequences, the test loci and reference loci can then be "matched" or grouped together according to their % GC content (e.g., test loci with a % GC content of 40% is matched with reference loci with a % GC content of 40%). It is appreciated that the % GC content matching procedure may allow slight variation in the allowed matched % GC range. A non-limiting instance, and with reference to the previously described example in text, a test locus with % GC content of 40% could be matched with reference loci of % GC ranging from 39-41%, thereby encompassing the test locus % GC within a suitable range.

To prepare a pool of TACS having the optimized criteria set forth above with respect to size, placement within the human genome and % GC content, both manual and computerized analysis methods known in the art can be applied to the analysis of the human reference genome. In one embodiment, a semi-automatic method is implemented were regions are firstly manually designed based on the human reference genome build 19 (hg19) ensuring that the aforementioned repetitive regions are avoided and subsequently are curated for GC-content using software that computes the % GC-content of each region based on its coordinates on the human reference genome build 19 (hg19). In another embodiment, custom-built software is used to analyse the human reference genome in order to identify suitable TACS regions which fulfil certain criteria, such as but not limited to, % GC content, proximity to repetitive regions and/or proximity to other TACS.

The number of TACS in the pool has been carefully examined and adjusted to achieve the best balance between result robustness and assay cost/throughput. The pool typically contains at least 800 or more TACS, but can include more, such as 1500 or more TACS, 2000 or more TACS or 2500 or more TACS. It has been found that an optimal number of TACS in the pool is 1600. It will be appreciated by the ordinarily skilled artisan that a slight variation in pool size typically can be used without altering the results (e.g., the addition or removal of a small number of TACS); accordingly, the number sizes of the pool given herein are to be considered "about" or "approximate", allowing for some slight variation (e.g., 1-5%) in size. Thus, for example, a pool size of "1600 sequences" is intended to refer to "about 1600 sequences" or "approximately 1600 sequences", such that, for example, 1590 or 1610 sequences is also encompassed.

In view of the foregoing, in another aspect, the invention provides a method for preparing a pool of TACS for use in the method of the invention for detecting risk of a chromosomal and/or other genetic abnormality, wherein the method for preparing the pool of TACS comprises: selecting regions in one or more chromosomes of interest having the criteria set forth above (e.g., at least 150 base pairs away on either end from the aforementioned repetitive sequences and a GC content of between 19% and 50%), preparing primers that amplify sequences that hybridize to the selected regions, and amplifying the sequences, wherein each sequence is 100-260 base pairs in length.

Sample Collection and Preparation

The methods of the invention are performed on a mixed sample that contains both maternal and fetal DNA. Typically the sample is a maternal plasma sample, although other tissue sources that contain both maternal and fetal DNA can be used. Maternal plasma can be obtained from a peripheral whole blood sample from a pregnant woman and the plasma can be obtained by standard methods. As little as 2-4 ml of plasma is sufficient to provide suitable DNA material for analysis according to the method of the invention. Total cell free DNA can then be extracted from the sample using standard techniques, non-limiting examples of which include a Qiasymphony protocol (Qiagen) suitable for free fetal DNA isolation or any other manual or automated extraction method suitable for cell free DNA isolation.

Following isolation, the cell free DNA of the mixed sample is used for sequencing library construction to make the sample compatible with a downstream sequencing technology, such as but not limited to Illumina Next Generation Sequencing. Typically this involves ligation of adapters onto the ends of the cell free DNA fragments, followed by amplification. Sequencing library preparation kits are commercially available. A non-limiting exemplary protocol for sequencing library preparation is described in detail in Example 1.

Enrichment by TACS Hybridization

The region(s) of interest on the chromosome(s) of interest is enriched by hybridizing the pool of TACS to the sequencing library, followed by isolation of those sequences within the sequencing library that bind to the TACS. To facilitate isolation of the desired, enriched sequences, typically the TACS sequences are modified in such a way that sequences that hybridize to the TACS can be separated from sequences that do not hybridize to the TACS. Typically, this is achieved by fixing the TACS to a solid support. This allows for physical separation of those sequences that bind the TACS from those sequences that do not bind the TACS. For example, each sequence within the pool of TACS can be labeled with biotin and the pool can then be bound to beads coated with a biotin-binding substance, such as streptavidin or avidin. In a preferred embodiment, the TACS are labeled with biotin and bound to streptavidin-coated magnetic beads. The ordinarily skilled artisan will appreciate, however, that other affinity binding systems are known in the art and can be used instead of biotin-streptavidin/avidin. For example, an antibody-based system can be used in which the TACS are labeled with an antigen and then bound to antibody-coated beads. Moreover, the TACS can incorporate on one end a sequence tag and can be bound to a solid support via a complementary sequence on the solid support that hybridizes to the sequence tag. Furthermore in addition to magnetic beads, other types of solid supports can be used, such as polymer beads and the like.

Following enrichment of the sequence(s) of interest using the TACS, thereby forming an enriched library, the members of the enriched library are eluted from the solid support and are amplified and sequenced using standard methods known in the art. Standard Illumina Next Generation Sequencing is typically used, although other sequencing technologies can also be employed, which provides very accurate counting in addition to sequence information. To detect genetic abnormalities, such as but not limited to, aneuploidies or structural copy number changes requires very accurate counting and NGS is a type of technology that enables very accurate counting. Accordingly, for the detection of genetic abnormalities, such as but not limited to, aneuploidies or structural copy number changes, other accurate counting methods, such as digital PCR and microarrays can also be used instead of NGS. Non-limiting exemplary protocols for amplification and sequencing of the enriched library are described in detail in Example 3.

Data Analysis

The information obtained from sequencing of the enriched library is analyzed using an innovative biomathematical/biostatistical data analysis pipeline. This analysis pipeline exploits the characteristics of the TACS, and the high-efficiency of the target capture enables efficient detection of aneuploidies or structural copy number changes, as well as other types of genetic abnormalities. Details of an exemplary analysis are described in depth in Example 4. In the analysis, first the sample's sequenced DNA fragments are aligned to the human reference genome. QC metrics are used to inspect the aligned sample's properties and decide whether the sample is suitable to undergo classification. These QC metrics can include, but are not limited to, analysis of the enrichment patterns of the loci of interest, such as for example the overall sequencing depth of the sample, the on-target sequencing output of the sample, TACS performance, GC bias expectation and fetal fraction quantification. For determining the risk of a chromosomal abnormality in the fetal DNA of the sample, an innovative algorithm is applied. The steps of the algorithm include, but are not limited to, removal of inadequately sequenced loci, read-depth and fragment-size information extraction at TACS-specific coordinates, genetic (GC-content) bias alleviation and ploidy status classification.

Ploidy status determination is achieved using one or more statistical methods, non-limiting examples of which include a t-test method, a bootstrap method, a permutation test and/or a binomial test of proportions and/or combinations thereof. It will be appreciated by the ordinarily skilled artisan that the selection and application of tests to be included in ploidy status determination is based on the number of data points available. As such, the suitability of each test is determined by various factors such as, but not limited to, the number of TACS utilized and the respective application for GC bias alleviation, if applicable. Thus, the aforementioned methods are to be taken as examples of the types of statistical analysis that may be employed and are not the only methods suitable for the determination of ploidy status. Typically, the statistical method results in a score value for the mixed sample and risk of the chromosomal abnormality in the fetal DNA is detected when the score value for the mixed sample is above a reference threshold value.

In particular, one aspect of the statistical analysis involves quantifying and alleviating GC-content bias. In addition to the challenge of detecting small signal changes in fetal DNA in the mixed sample (for example, but not limited to, additional or less genetic material from certain fetal chromosomal regions), the sequencing process itself introduces certain biases that can obscure signal detection. One such bias is the preferential sequencing/amplification of genetic regions based on their GC-content. As such, certain detection methods, such as but not limited to, read-depth based methods, need to account for such bias when examining sequencing data. Thus, the bias in the data needs to be quantified and, subsequently, suitable methods are applied to account for it such that genetic context dependencies cannot affect any statistical methods that may be used to quantify fetal genetic abnormality risk.

For example, one method of quantifying the GC-content bias is to use a locally weighted scatterplot smoothing (LOESS) technique on the sequencing data. Each targeted locus may be defined by its sequencing read-depth output and its' GC-content. A line of best fit through these two variables, for a large set of loci, provides an estimate of the expected sequencing read-depth given the GC-content. Once this GC-bias quantification step is completed, the next step is to use this information to account for possible biases in the data. One method is to normalize the read-depth of all loci by their expected read-depth (based on each locus' GC-content). In principle, this unlinks the read-depth data from their genetic context and makes all data comparable between them. As such, data that are retrieved from different GC-content regions, such as for example, but not limited, to different chromosomes, can now be used in subsequent statistical tests for detection of any abnormalities. Thus, using the LOESS procedure, the GC bias is unlinked from the data prior to statistical testing. In one embodiment, the statistical analysis of the enriched library sequences comprises alleviating GC bias using a LOESS procedure.

In an alternative preferred embodiment, the GC-content bias is quantified and alleviated by grouping together loci of similar (matching) GC-content. Thus, conceptually this method for alleviating GC-content bias is comprised of three steps, as follows:

1) identification and calculation of GC-content in the TACS;
2) alleviation/accounting of GC-content bias using various matching/grouping procedures of the TACS; and
3) calculation of risk of any genetic abnormalities that may be present in the fetus utilizing statistical and mathematical methods on datasets produced from step 2.

For the t-test method, the dataset is split into two groups; the test loci and the reference loci. For each group, subsets of groups are created where loci are categorized according to their GC-content as illustrated in a non-limiting example in the sample Table 1 below:

TABLE 1

| GC | Reference loci read-depth | Test loci read-depth |
|---|---|---|
| 40% | $x_1^{40}, x_2^{40}, \ldots, x_{nx40}^{40}$ | $y_1^{40}, y_2^{40}, \ldots, y_{ny40}^{40}$ |
| 41% | $x_1^{41}, x_2^{41}, \ldots, x_{nx41}^{41}$ | $y_1^{41}, y_2^{41}, \ldots, y_{ny41}^{41}$ |
| 42% | $x_1^{42}, x_2^{42}, \ldots, x_{nx42}^{42}$ | $y_1^{42}, y_2^{42}, \ldots, y_{ny42}^{42}$ |
| ... | ... | ... |

It is appreciated by the ordinarily skilled artisan that subgroup creation may involve encompassing a range of appropriate GC-content and/or a subset of loci that are defined by a given GC-content and/or GC-content range. Accordingly, the % GC content given in the non-limiting example of Table 1 are to be considered "about" or "approximate", allowing for some slight variation (e.g., 1-2%). Thus, for example, a % GC content of "40%" is intended to refer to "about 40%" or "approximately 40%", such that, for example, "39%-41%" GC-content loci may also be encompassed if deemed appropriate. Hence, when referring to a particular GC-content it is understood that the reference and test loci subgroups may comprise of any number of loci related to a particular % GC content and/or range.

Subsequently, for each GC-content subgroup, a representative read-depth is calculated. A number of methods may be utilized to choose this such as, but not limited to, the mean, median or mode of each set. Thus, two vectors of representative read-depth are created where one corresponds to the reference loci and the other to the test loci (e.g., Xm, Ym). In one embodiment, the two vectors may be tested against each other to identify significant differences in read-depth. In another embodiment, the difference of the two vectors may be used to assess if there are significant discrepancies between the test and reference loci. The sample is attributed the score of the test.

For statistical analysis using a bootstrap approach, the dataset is split into two groups, the test loci and the reference loci. The GC-content of each locus is then calculated. Then the following procedure is performed:

A random locus is selected from the reference loci; its read-depth and GC-content are recorded. Subsequently, a random locus from the test loci is selected, with the only condition being that its' GC-content is similar to that of the reference locus. Its read-depth is recorded. It is appreciated by the ordinarily skilled artisan that GC-content similarity may encompass a range of suitable GC-content. As such, referral to a specific % GC content may be considered as "approximate" or "proximal" or "within a suitable range" (e.g 1%-2%) encompassing the specific % GC content under investigation. Thus, a reference-test locus pair of similar GC-content is created. The difference of the reference-test pair is recorded, say E1. The loci are then replaced to their respective groups. This process is repeated until a bootstrap sample of the same size as the number of test TACS present is created. A representative read-depth of the bootstrap sample is estimated, say E_mu, and recorded. A number of methods may be utilized to do so, such as but not limited to, the mean, mode or median value of the vector, and/or multiples thereof.

The process described above is repeated as many times as necessary and a distribution of E_mu is created. The sample is then attributed a score that corresponds to a percentile of this distribution.

For statistical analysis using a permutation test, the dataset is sorted firstly into two groups, the test-loci and the reference loci. For each group, subsets of groups are created, where loci are categorized according to their GC-content similarity (see columns 2 and 3 of the non-limiting sample Table 2 below). The number of loci present in each test subgroup is also recorded. The loci of the test group are utilized to calculate an estimate of the test-group's read-depth, say Yobs. A representative number from each GC-content subgroup may be selected to do so. Any number of methods may be used to provide a read-depth estimate, such as but not limited to, the mean, median or mode of the chosen loci.

TABLE 2

| GC | Reference loci read-depth | Test loci read-depth | test loci num | Merging of loci |
|---|---|---|---|---|
| 40% | $x_1^{40}, x_2^{40}, \ldots, x_{nx40}^{40}$ | $y_1^{40}, y_2^{40}, \ldots, y_{ny40}^{40}$ | ny40 | $x_1^{40}, \ldots, x_{nx40}^{40}, y_1^{40}, \ldots, y_{ny40}^{40}$ |
| 41% | $x_1^{41}, x_2^{41}, \ldots, x_{nx41}^{41}$ | $y_1^{41}, y_2^{41}, \ldots, y_{ny41}^{41}$ | ny41 | $x_1^{41}, \ldots, x_{nx41}^{41}, y_1^{41}, \ldots, y_{ny41}^{41}$ |
| 42% | $x_1^{42}, x_2^{42}, \ldots, x_{nx42}^{42}$ | $y_1^{42}, y_2^{42}, \ldots, y_{ny42}^{42}$ | ny42 | $x_1^{42}, \ldots, x_{nx42}^{42}, y_1^{42}, \ldots, y_{ny42}^{42}$ |
| ... | ... | ... | ... | ... |

A distribution to test Yobs is then built utilizing loci irrespective of their test or reference status as follows. The test and reference loci of each GC-content subgroup (see last column of sample Table 2) are combined to allow for calculation of a new read-depth estimate. From each merged subgroup a number of loci are chosen at random, where this number is upper-bounded by the number of test-loci utilized in the original calculation of Yobs (e.g for GC content 40%, and in the context of the non-limiting sample Table 2, this number of loci may be in the range [1,ny40]). The new read-depth estimate is calculated from all the chosen loci. The procedure is iterated as many times as necessary in order to build a distribution of observed means. A sample is then attributed a score that corresponds to the position of Yobs in this distribution using a suitable transformation that accounts for the moments of the built distribution. As with the already described methods, it is appreciated that slight variation in % GC content is allowed (e.g 1%-2%), if deemed appropriate. Hence, reference to a specific GC-content could be taken as "about" or "approximate", so that for example when referring to a 40% GC-content, loci that are "approximately" or "about" 40% (e.g 39%-41%) may be utilized in the method.

For statistical analysis using a binomial test of proportions, fragment-sizes aligned to TACS-specific genomic coordinates are used. It has been shown that fragments of cell free genetic material originating from the placenta are smaller in length when compared to other cell free genetic material (Chan, K. C. (2004) *Clin. Chem.* 50:88-92). Hence, the statistic of interest is whether the proportion of small-size fragments aligned to a TACS-specific test-region deviates significantly from what is expected when comparing it to the respective proportion of other TACS-specific reference-regions, as this would indicate fetal genetic abnormalities.

Thus, fragment-sizes are assigned into two groups. Sizes related to the test loci are assigned to one group and fragment-sizes related to the reference loci are assigned to the other group. Subsequently, in each group, fragment sizes are distributed into two subgroups, whereby small-size fragments are assigned into one subgroup and all remaining fragments are designated to the remaining subgroup. The last step computes the proportion of small-sized fragments in each group and uses these quantities in a binomial test of proportions. The score of the test is attributed to the sample under investigation.

The final result of a sample may be given by combining one or more scores derived from the different statistical methods, non-limiting examples of which are given in Example 4.

Kits of the Invention

In another aspect, the invention provides kits for carrying out the methods of the invention. In one embodiment, the kit comprises a container consisting of the pool of TACS and instructions for performing the method. In one embodiment, the TACS are provided in a form that allows them to be bound to a solid support, such as biotinylated TACS. In another embodiment, the TACS are provided together with a solid support, such as biotinylated TACS provided together with streptavidin-coated magnetic beads. In various other embodiments, the kit can comprise additional components for carrying out other aspects of the method. For example, in addition to the pool of TACS, the kit can comprise one or more of the following (i) one or more components for isolating cell free DNA from a maternal plasma sample (e.g., as described in Example 1); (ii) one or more components for preparing the sequencing library (e.g., primers, adapters, linkers, restriction enzymes, ligation enzymes, polymerase enzymes and the like as described in detail in Example 1); (iii) one or more components for amplifying and/or sequencing the enriched library (e.g., as described in Example 3); and/or (iv) software for performing statistical analysis (e.g., as described in Example 4).

IV. EXAMPLES

The present invention is further illustrated by the following examples, which should not be construed as further limiting. The contents of all references, appendices, Genbank entries, patents and published patent applications cited throughout this application are expressly incorporated herein by reference in their entirety.

Example 1: Sample Collection and Library Preparation

Sample Collection

Plasma samples were obtained anonymously from pregnant women after the 10th week of gestation. Protocols used for collecting samples for our study were approved by the Cyprus National Bioethics Committee, and informed consent was obtained from all participants.

Sample Extraction

Cell Free DNA was extracted from 2-4 ml plasma from each individual using a manual or automated extraction method suitable for cell free DNA isolation such as for example, but not limited to, Qiasymphony protocol suitable for free fetal DNA isolation (Qiagen).

Library Preparation

Extracted DNA from maternal plasma samples was used for sequencing library construction. Standard library preparation methods were used with the following modifications (Meyer, M. and Kircher, M. (2010) *Cold Spring Harb. Protoc.* 2010(6):pdb prot5448). A negative control extraction library was prepared separately to monitor any contamination introduced during the experiment. During this step, 5' and 3' overhangs were filled-in, by adding 12 units of T4 polymerase (NEB) while 5' phosphates were attached using 40 units of T4 polynucleotide kinase (NEB) in a 100 µl reaction and subsequent incubation at 25° C. for 15 minutes and then 12° C. for 15 minutes. Reaction products were purified using the MinElute kit (Qiagen). Subsequently, adaptors P5 and P7 (see adaptor preparation) were ligated at 1:10 dilution to both ends of the DNA using 5 units of T4 DNA ligase (NEB) in a 40 µl reaction for 20 minutes at room temperature, followed by purification using the MinElute kit (Qiagen). Nicks were removed in a fill-in reaction with 16 units of Bst polymerase (NEB) in a 40 µl reaction with subsequent incubation at 65° C. for 25 minutes and then 12° C. for 20 minutes. Products were purified using the MinElute kit (Qiagen). Library amplification was performed using a Fusion polymerase (Herculase II Fusion DNA polymerase (Agilent Technologies) or Pfusion High Fidelity Polymerase (NEB)) in 50 µl reactions and with the following cycling conditions, 95° C. for 3 min; followed by 10 cycles at 95° C. for 30 sec, 60° C. for 30 sec, 72° C. for 30 sec and finally 72° C. for 3 min. The final library products were purified using the MinElute Purification Kit (Qiagen) and measured by spectrophotometry.

Adaptor Preparation

Hybridization mixtures for adapter P5 and P7 were prepared (26) separately and incubated for 10 sec at 95° C. followed by a ramp from 95° C. to 12° C. at a rate of 0.1° C./sec. P5 and P7 reactions were combined to obtain a ready-to-use adapter mix (100 µM of each adapter). Hybridization mixtures were prepared as follows: P5 reaction mixture contained adaptor P5_F (500 µM) at a final concentration of 200 µM, adaptor P5+P7_R (500 µM) at a final concentration of 200 µM with 1× oligo hybridization buffer. In addition, P7 reaction mixture contained adaptor P7_F (500 µM) at a final concentration of 200 µM, adapter P5+P7_R(500 µM) at a final concentration of 200 µM with 1× oligo hybridization buffer (30). Sequences were as follows, wherein *=a phosphorothioate bond (PTO) (Integrated DNA Technologies) (Meyer, M. and Kircher, M. (2010) *Cold Spring Harb. Protoc.* 2010(6):pdb prot5448):

```
adaptor P5_F:
                                        (SEQ ID NO: 1)
A*C*A*C*TCTTTCCCTACACGACGCTCTTCCG*A*T*C*T adaptor P7_F:
                                        (SEQ ID NO: 2)
G*T*G*A*CTGGAGTTCAGACGTGTGCTCTTCCG*A*T*C*T, adaptor_P5 + P7_R:
                                        (SEQ ID NO: 3)
A*G*A*T*CGGAA*G*A*G*C
```

Example 2: TArget Capture Sequences (TACS) Design and Preparation

Figure 2U:
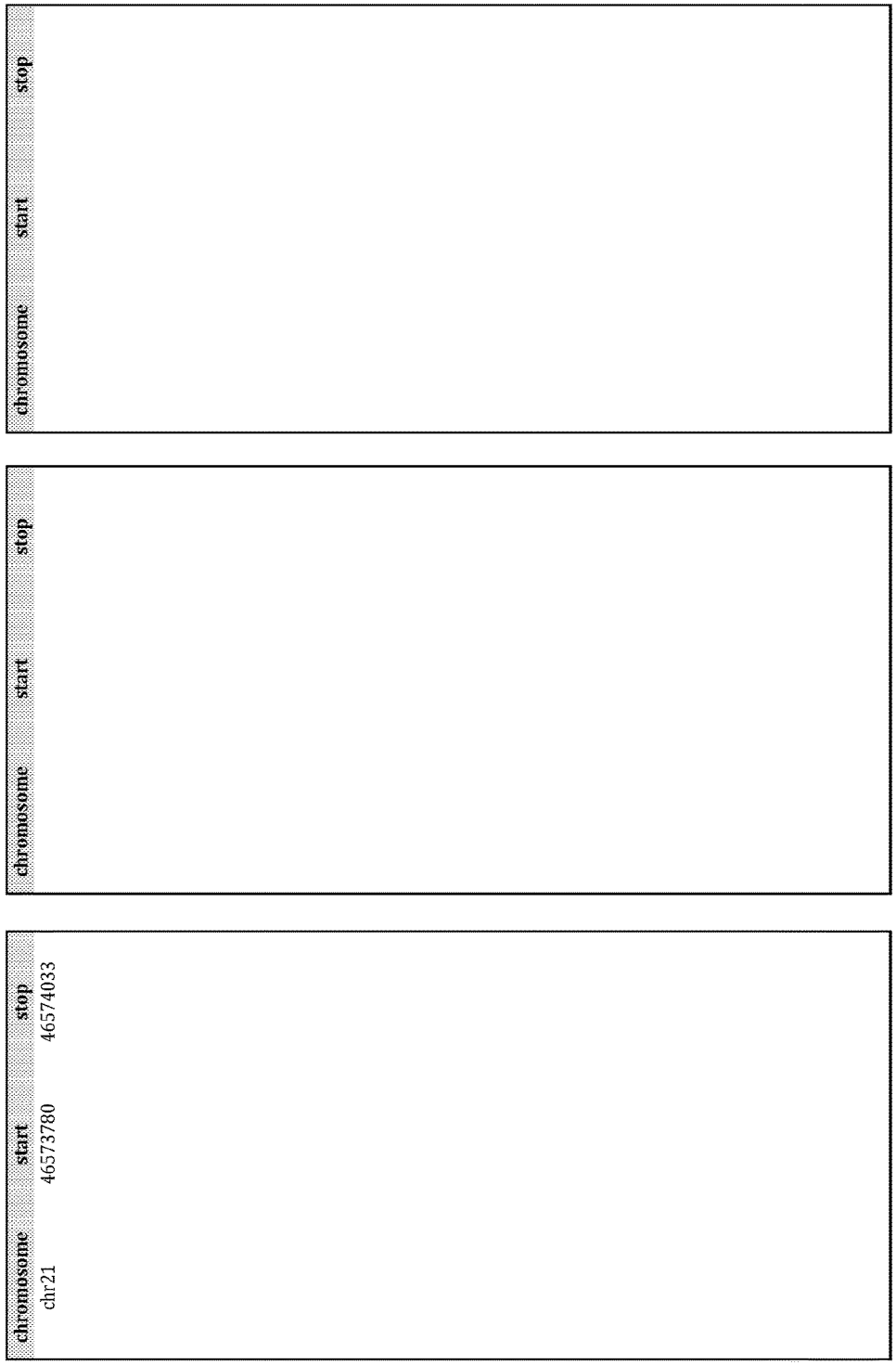
FIG. 2A-2AE is a listing of exemplary chromosomal regions for amplifying TACS that bind to chromosomes 13, 18, 21 or X (FIG. 2A-2U) and to the reference loci on chromosomes 2, 3, 4, 5, 6, 7, 9, 11 or 12 (FIG. 2V-2AE).
Figure 2W:
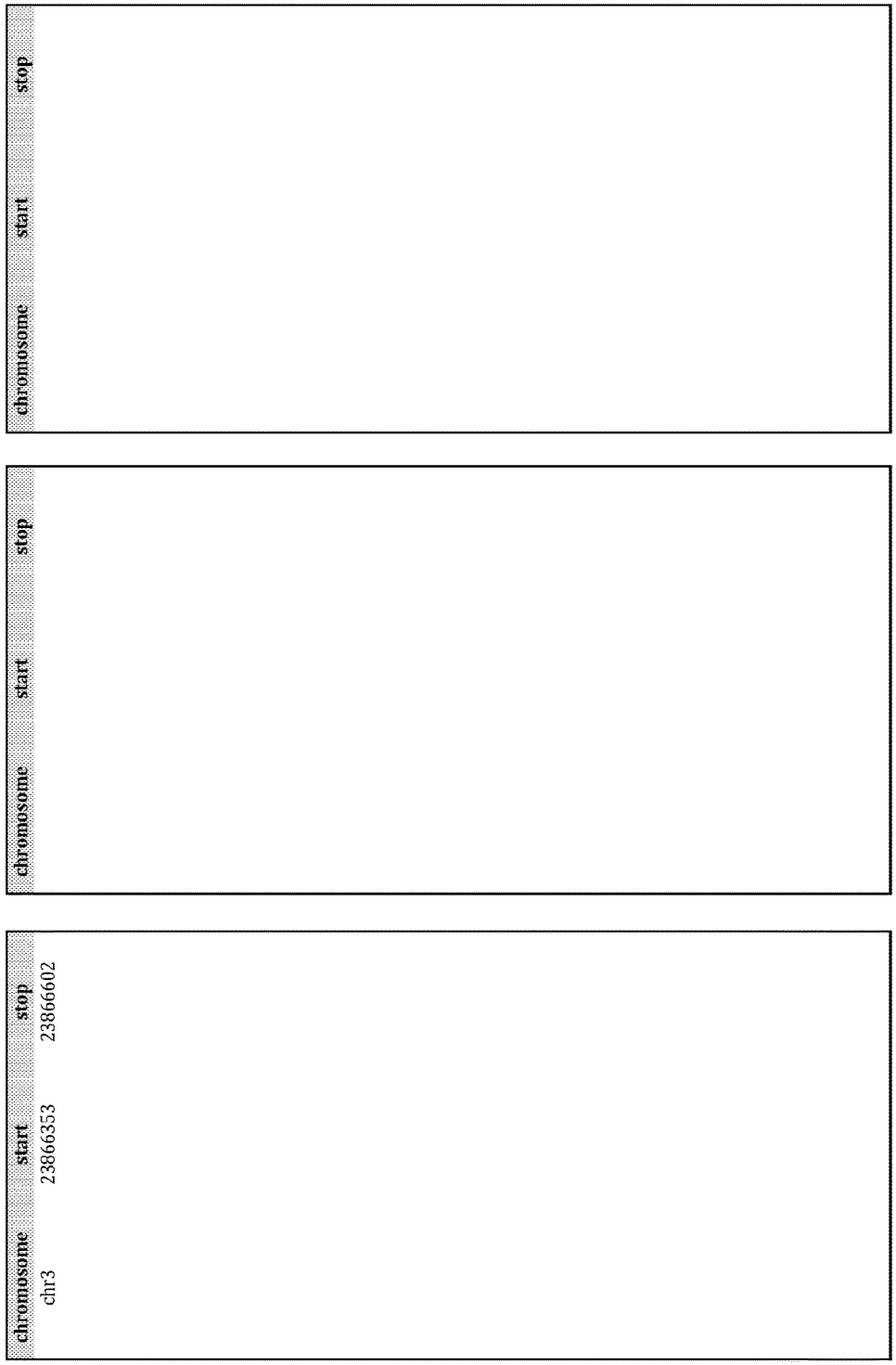
Figure 2A:
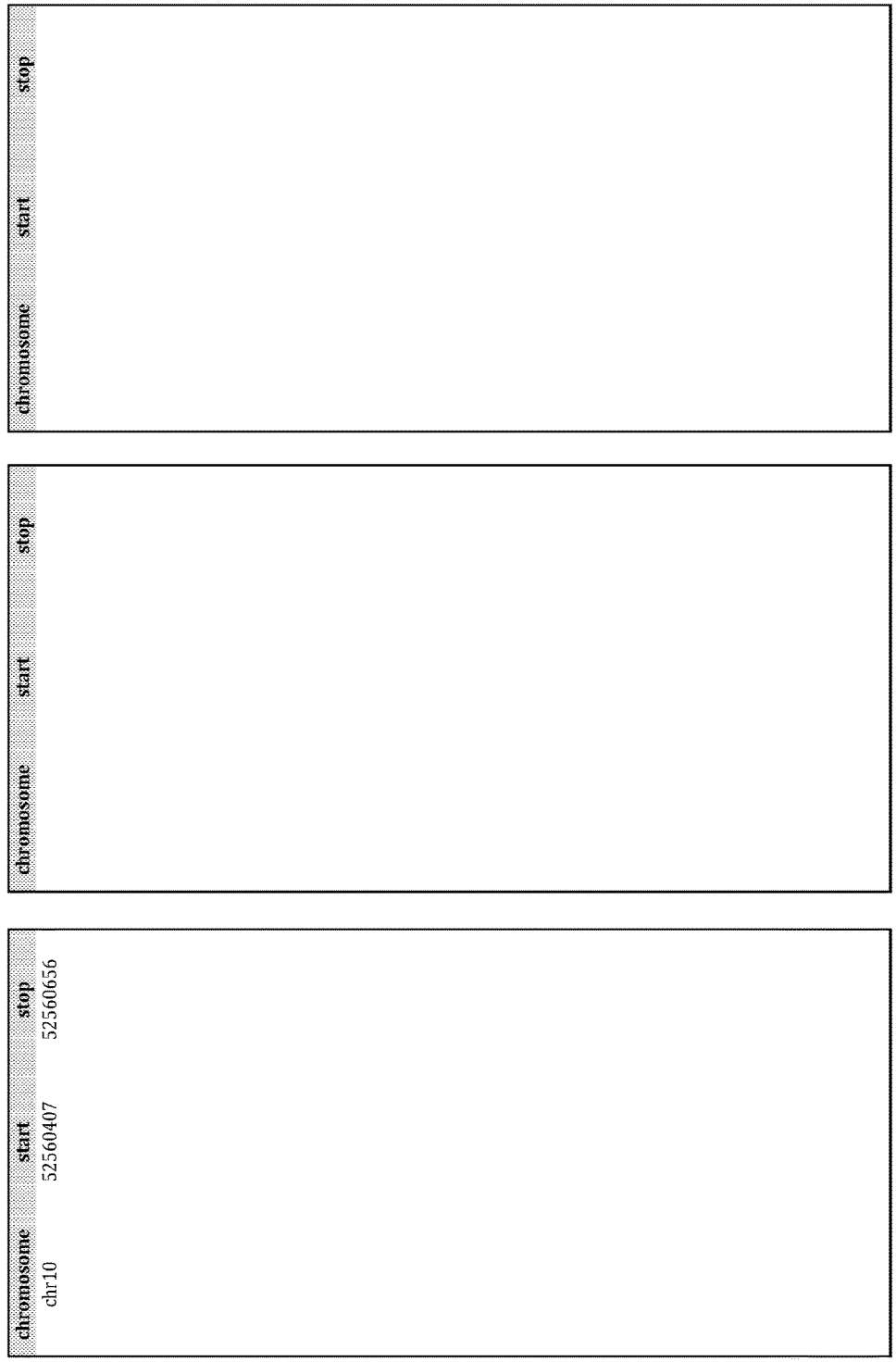
Figure 2A:
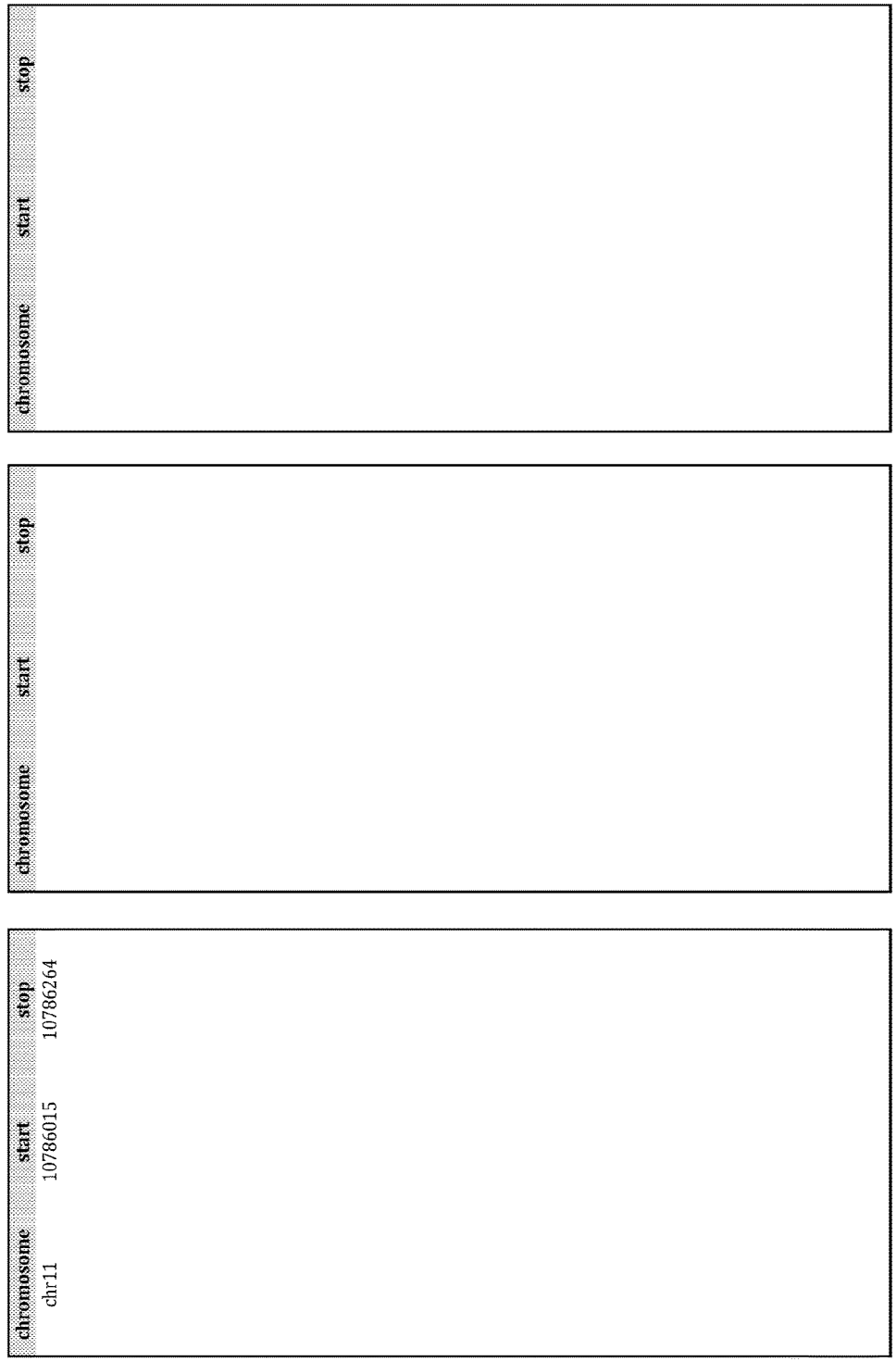
Figure 2A:
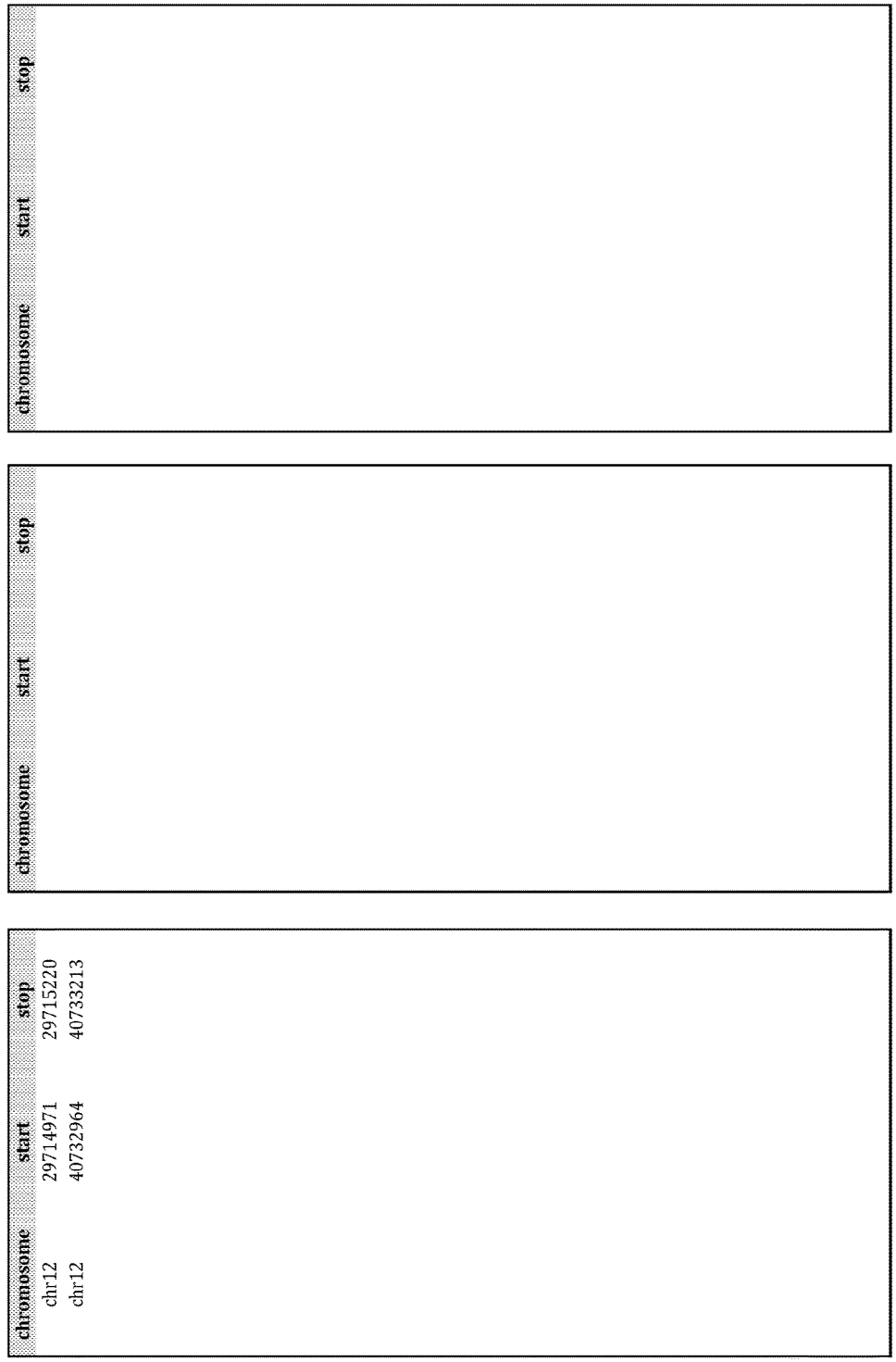

Custom TACS were prepared for the detection of whole or partial chromosomal abnormalities for chromosomes 13, 18, 21, X, Y or any other chromosome, as well as other genetic abnormalities, such as but not limited to, microdeletion/microduplication syndromes, translocations, inversions, insertions, and other point or small size mutations. The genomic target-loci used for TACS design were selected based on their GC content and their distance from repetitive elements (minimum 150 bp away). TACS size can be variable. In one embodiment of the method the TACS range from 100-260 bp in size and are generated through a PCR-based approach as described below. The TACS were prepared by simplex polymerase chain reaction using standard Taq polymerase, primers designed to amplify the target-loci, and normal DNA used as template. The chromosomal regions used to design primers to amplify suitable loci on chromosomes 13, 18, 21 and X, to thereby prepare the pool of TACS are shown in FIG. 2A-2AE.

All custom TACS were generated using the following cycling conditions: 95° C. for 3 min; 40 cycles at 95° C. for 15 sec, 60° C. for 15 sec, 72° C. for 12 sec; and 72° C. for 12 sec, followed by verification via agarose gel electrophoresis and purification using standard PCR clean up kits such as the Qiaquick PCR Purification Kit (Qiagen) or the NucleoSpin 96 PCR clean-up (Mackerey Nagel) or the Agencourt AMPure XP for PCR Purification (Beckman Coulter). Concentration was measured by Nanodrop (ermo Scientific).

Example 3: TACS Hybridization and Amplification

TACS Biotinylation

TACS were prepared for hybridization, as previously described (Maricic, T. et al. (2010) *PLoS One* 5:e14004) with minor modifications, starting with blunt ending with the Quick Blunting Kit (NEB) and incubation at room temperature for 30 minutes. Reaction products were subsequently purified using the MinElute kit (Qiagen) and were ligated with a biotin adaptor using the Quick Ligation Kit (NEB) in a 40 µl reaction at RT for 15 minutes. The reaction products were purified with the MinElute kit (Qiagen) and were denatured into single stranded DNA prior to immobilization on streptavidin coated magnetic beads (Invitrogen).

TACS Hybridization

Amplified libraries were mixed with blocking oligos (Maricic, T. supra) (200 µM), 5 µg of Cot-1 DNA (Invitrogen), 50 µg of Salmon Sperm DNA (Invitrogen), Agilent hybridization buffer 2×, Agilent blocking agent 10×, and were heated at 95° C. for 3 min to denature the DNA strands. Denaturation was followed by 30 minute incubation at 37° C. to block repetitive elements and adaptor sequences. The resulting mixture was then added to the biotinylated TACS. All samples were incubated in a rotating incubator for 12-48 hours at 66° C. After incubation, the beads were washed as described previously and DNA was eluted by heating (Maricic, T. supra). Eluted products were amplified using outer-bound adaptor primers. Enriched amplified products were pooled equimolarly and sequenced on an illumina or any other suitable platform.

Example 4: Bioinformatics Sample Analysis

Human Genome Alignment

For each sample, the bioinformatic pipeline routine described below was applied in order to align the sample's sequenced DNA fragments to the human reference genome. Targeted paired-end read fragments obtained from NGS results were processed to remove adaptor sequences and poor quality reads (Q-score<25) using the cutadapt software (Martin, M. et al. (2011) *EMB.netJournal* 17.1). The quality of the raw and/or processed reads as well as any descriptive statistics which aid in the assessment of quality check of the sample's sequencing output were obtained using the FastQC software (Babraham Institute (2015) *FastQC*) and/or other custom-built software. Processed reads which were at least 25 bases long were aligned to the human reference genome built hg19 (UCSC Genome Bioinformatics) using the Burrows-Wheel Alignment algorithm (Li, H. and Durbin, R. (2009) *Bioinformatics* 25:1754-1760). If relevant, duplicate reads were removed post-alignment. Where applicable, sequencing output pertaining to the same sample but processed on separate sequencing lanes, was merged to a single sequencing output file. The removal of duplicates and merging procedures were performed using the Picard tools software suite (Broad Institute (2015) Picard) and/or the Sambamba tools software suite (Sambamba reference, Tarasov, Artem, et al. "Sambamba: fast processing of NGS alignment formats." *Bioinformatics* 31.12 (2015). 2032-2034).

The above software analysis resulted in a final aligned version of a sequenced sample against the human reference genome and all subsequent steps were based on this aligned version. Information in terms of Short Nucleotide Polymorphisms (SNPs) at loci of interest was obtained using bcftools from the SAMtools software suite (Li, H. et al. (2009) *Bioinformatics* 25:2078-2079). The read-depth per base, at loci of interest, was obtained using the mpileup option of the SAMtools software suite, from here on referred to as the mpileup file. Information pertaining to the size of the aligned fragments was obtained using the view option of the SAMtools software suite, from here on referred to as the fragment-sizes file.

The mpileup file and the fragment-sizes file were processed using custom-build application programming interfaces (APIs) written in the Python and R programming languages (Python Software Foundation (2015) *Python*; The R Foundation (2015) *The R Project for Statistical Computing*). The APIs were used to determine the ploidy state of chromosomes of interest using a series of steps (collectively henceforth referred to as the "algorithm") and to also collect further descriptive statistics to be used as quality check metrics, such as but not limited to fetal fraction quantification (collectively henceforth referred to as the "QC metrics"). The APIs can also be used for the assessment of genetic abnormalities from data generated when applying the described method in cases of multiple gestation pregnancies, as well as other genetic abnormalities such as, but not limited to, microdeletions, microduplications, copy number variations, translocations, inversions, insertions, point mutations and mutational signatures.

OC Metrics

QC metrics were used to inspect an aligned sample's properties and decide whether the sample was suitable to undergo classification. These metrics were, but are not limited to:

(a) The enrichment of a sample. The patterns of enrichment are indicative of whether a sample has had adequate enrichment across loci of interest in a particular sequencing experiment (herein referred to as a "run"). To assess this, various metrics are assessed, non-limiting examples of which are:
  (i) overall sample on-target read depth,
  (ii) sample on-target sequencing output with respect to total mapped reads,
  (iii) individual TACS performance in terms of achieved read-depth,
  (iv) kurtosis and skewness of individual TACS enrichment and,
  (v) kurtosis and skewness moments that arise from all TACS.

The above checks are also taken into consideration with regards to GC-bias enrichment. Samples that fail to meet one or more of the criteria given above are flagged for further inspection, prior to classification.

(b) A sample's fetal fraction. Samples with an estimated fetal fraction that is below a specific threshold are not classified.

The Algorithm

The algorithm is a collection of data processing, mathematical and statistical model routines arranged as a series of steps. The algorithm's steps aim in deciding the relative ploidy state of a chromosome of interest with respect to all other chromosomes of the sequenced sample and is used for the detection of whole or partial chromosomal abnormalities for chromosomes 13, 18, 21, X, Y or any other chromosome, as well as other genetic abnormalities such as, but not limited to, microdeletion/microduplication syndromes and other point or small size mutations. As such the algorithm can be used, but is not limited to, the detection of whole or partial chromosomal abnormalities for chromosomes 13, 18, 21, X,Y or any other chromosome, as well as other genetic abnormalities such as, but not limited to, microdeletions, microduplications, copy number variations, translocations, inversions, insertions, point mutations and other mutational signatures. The algorithm carries out, but is not limited to, two types of assessments, one pertaining to the read-depth information of each sample and the other to the distribution of fragment-sizes, across TACS-specific regions. One or more statistical tests may be associated with each type of assessment, non-limiting examples of which are given in the statistical methods described herein.

In the case of read-depth associated tests, the algorithm compares sequentially the read-depth of loci from each chromosome of interest (herein referred to as the test chromosome) against the read-depth of all other loci (herein referred to as the reference loci) to classify its ploidy state. For each sample, these steps were, but are not limited to:

(a) Removal of inadequately sequenced loci. The read-depth of each locus was retrieved. Loci that have not achieved a minimum number of reads, were considered as inadequately enriched and were removed prior to subsequent steps.

(b) Genetic (GC-content) bias alleviation. The sequencing procedure introduces discrepancies in read-depth across the loci of interest depending on their GC content. To account for such bias, a novel sequence-matching approach that increases both sensitivity and specificity to detect chromosomal aneuploidies was employed. The GC content of each locus on the test chromosome was identified and similar genetic loci were grouped together to form genetically matched groups. The procedure was repeated for the reference loci. Then, genetically matched groups from the test chromosome were conditionally paired with their genetically matched group counterparts on the reference chromosome(s). The groups may have any number of members. The conditionally matched groups were then used to assess the ploidy status of test chromosomes.

Figure 3:
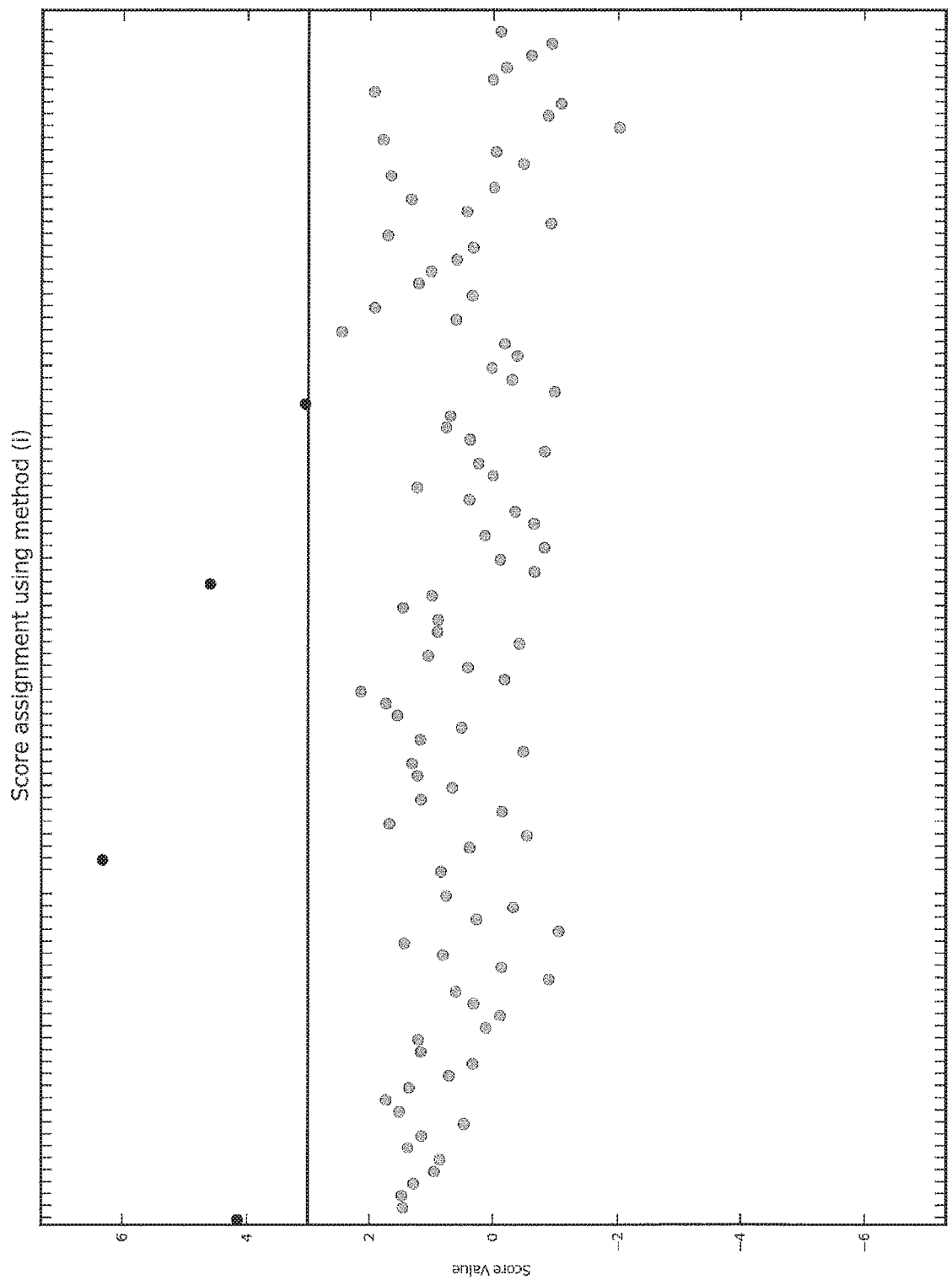
FIG. 3 is a graph of the score value assignment of 98 maternal blood samples subjected to multiplexed parallel analysis of targeted genomic regions using TACS for trisomy 21 risk detection, wherein the differences in median read-depth of the conditionally paired groups are tested for statistical significance using a t-test formula (referred to herein as statistical method 1).

(c) Ploidy status determination. Ploidy status determination was achieved using a single statistical method and/or a weighted score approach on the result from the following, but not limited to, statistical methods:

Statistical Method 1:

The differences in read-depth of the conditionally paired groups were tested for statistical significance using the t-test formula:

$$t = \frac{\bar{x} - \mu}{s/\sqrt{n}}$$

where t is the result of the t-test, $\bar{x}$ is the average of the differences of the conditionally paired groups, $\mu$ is the expected read-depth and is set to a value that represents insignificant read-depth differences between the two groups, s the standard deviation of the differences of the conditionally paired groups and n the length of the vector of the conditionally paired differences. The magnitude of the t-score was then used to identify evidence, if any, against the null hypothesis of same ploidy between reference and test chromosomes. Specifically, t>=c1 (where c1 is a predefined threshold belonging to the set of all positive numbers) shows evidence against the null. Results of the analysis of 98 maternal samples for chromosome 21 using this method are shown in FIG. 3.

Figure 4:
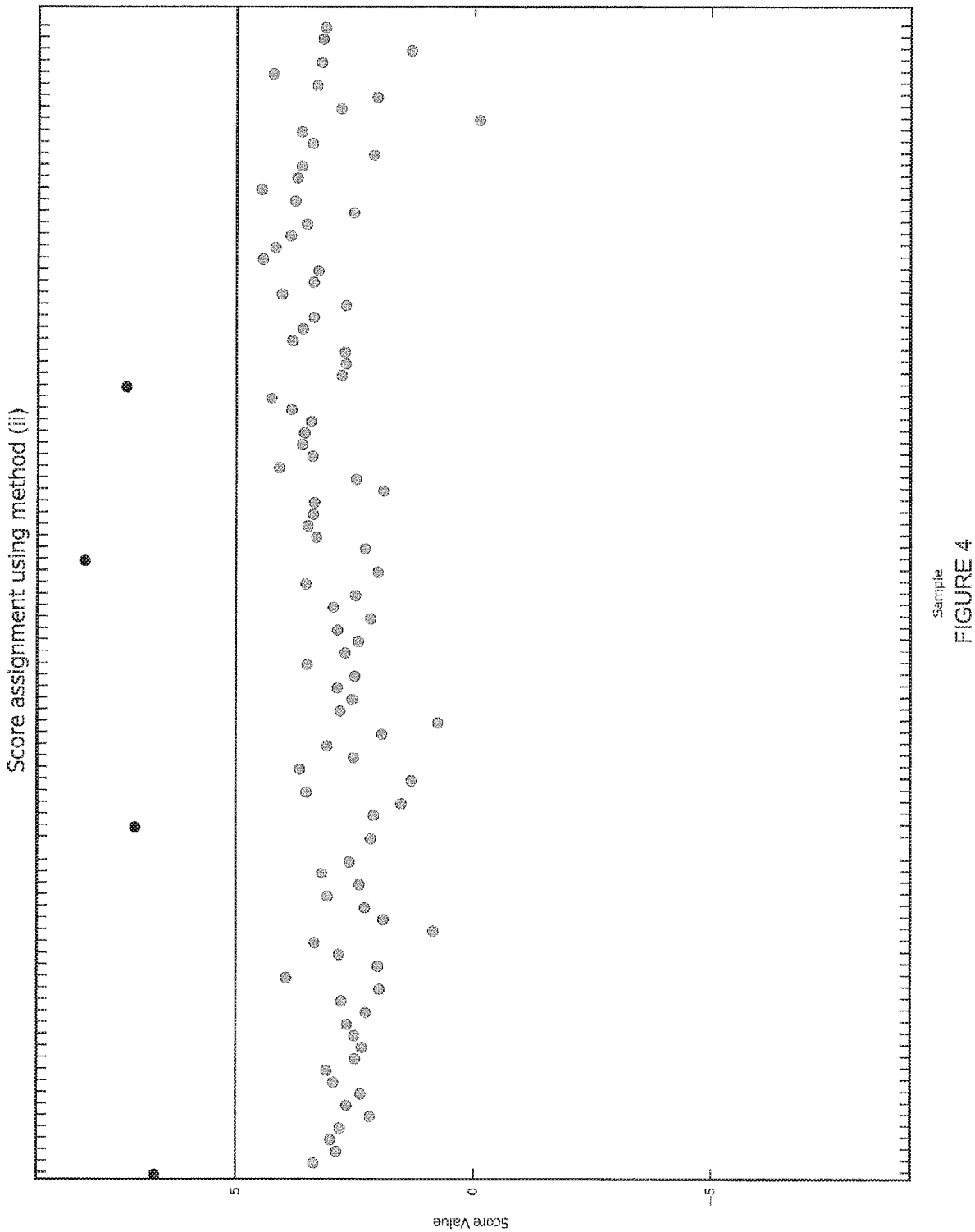
FIG. 4 is a graph of the score value assignment of 98 maternal blood samples subjected to multiplexed parallel analysis of targeted genomic regions using TACS for trisomy 21 risk detection, analyzed using a bivariate nonparametric bootstrap method (referred to herein as statistical method 2).

Statistical Method 2:

Bivariate nonparametric bootstrap. The bootstrap method depends on the relationship between the random variables X (read-depth of reference loci) and Y (read-depth of test loci). Here, we treated the read depth of baits on the reference group (random variable denoted by X) as the independent covariate. The first step of the iterative procedure involved random sampling with replacement (bootstrapping) of the read-depths of loci on the reference chromosomes, i.e. (x1,g1), ..., (xn,gn), where the parameter g is known and denotes the GC-content of the chosen bait. Ten, for each randomly selected reference bait (xi,gi), a corresponding read depth was generated for a genetically matched locus i.e (y1,g1), ..., (yn,gn). Thus, the bivariate data (x1,y1), (x2,y2), ..., (xn,yn) was arrived at, which was conditionally matched on their GC-content (parameter gi). The differences between the read depths of the genetically matched bootstrapped values xi and yi were used to compute the statistic of interest in each iteration. In one embodiment this statistical measure can be, but is not limited to, the mode, mean or median of the recorded differences, and/or multiples thereof. The procedure was repeated as necessary to build up the distribution of the statistic of interest from these differences. The sample was assigned a score that corresponds to a specific percentile of the built distribution (e.g. $5^{th}$ percentile). Under the null hypothesis the ploidy between chromosomes in the reference and test groups is not different. As such, samples whose score for a particular chromosome, was greater than a predefined threshold, say c2, were classified as statistically unlikely to have the same ploidy. Other statistical measures may be employed. Results of the analysis of 98 maternal samples for chromosome 21 using this method are shown in FIG. 4.

Statistical Method 3:

Stratified permutation test. The statistic of interest is the read-depth estimate of the test chromosome, denoted by $\hat{Y}_{obs}$, which is calculated using all loci of the test chromosome's genetically matched groups as follows:

$$\hat{Y}_{obs} = \frac{\sum_{j=1}^{j=T} \sum_{i=1}^{i=Nj} y_{ij}}{\sum_{j=1}^{j=T} Nj}$$

where $y_{ij}$ is the read-depth of locus i part of the genetically matched group j (i.e loci belonging to a specific group based on their GC-content), Nj is the number of test loci part of the genetically matched group j and T the number of genetically matched groups.

Figure 5:
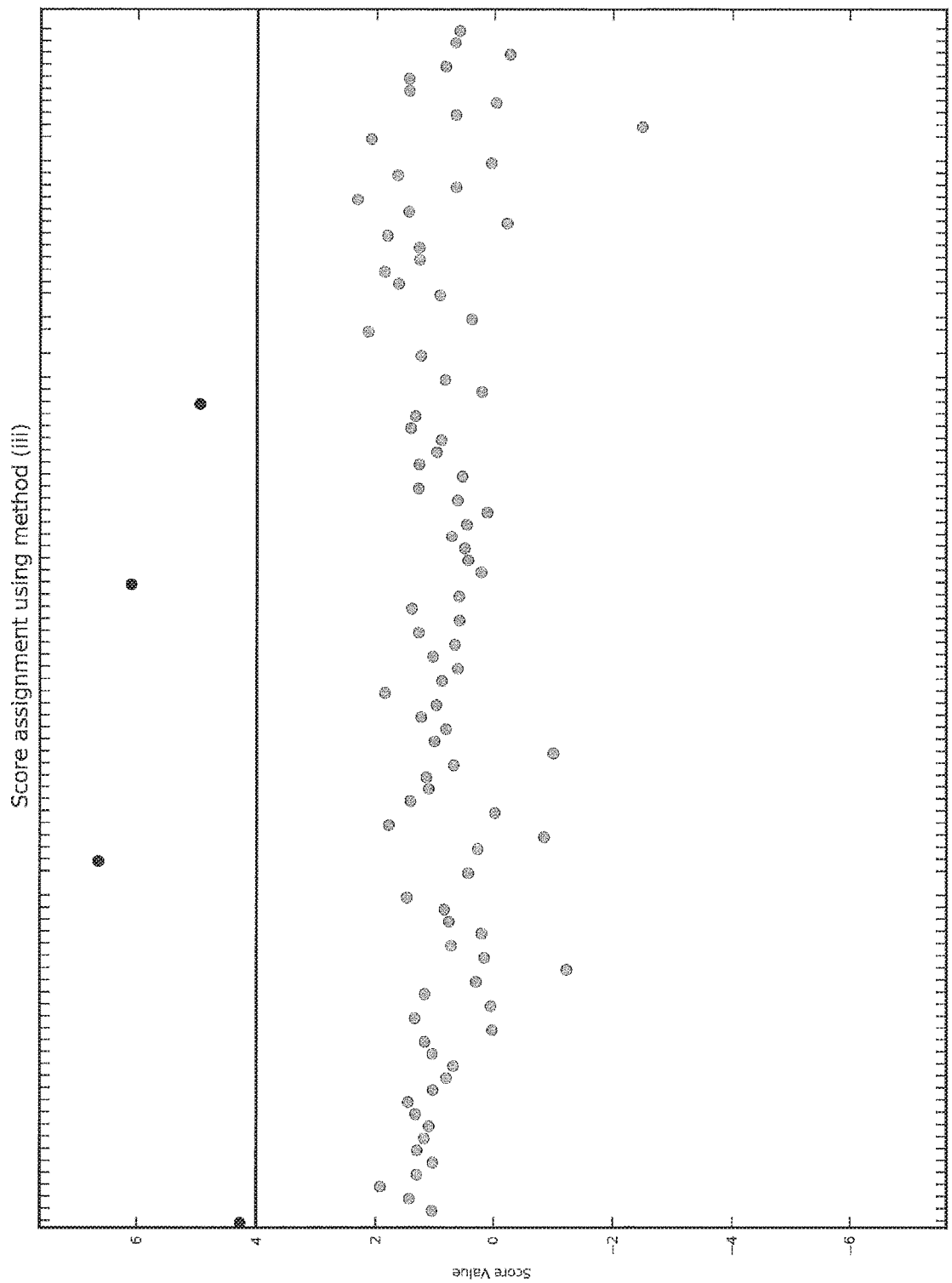
FIG. 5 is a graph of the score value assignment of 98 maternal blood samples subjected to multiplexed parallel analysis of targeted genomic regions using TACS for trisomy 21 risk detection, analyzed using a stratified permutation test (referred to herein as statistical method 3).

Subsequently, a null distribution to test $\hat{Y}_{obs}$ was built. To do so, for each group j, the test and reference loci were combined (exchangeability under the null hypothesis), and each group j was sampled randomly up to Nj times without replacement (stratified permutation). This created a vector of values, say yi, and from this the vector's average value, say $\hat{y}_i$, was calculated. The procedure was repeated as necessary to build the null distribution. Finally, $\hat{Y}_{obs}$—was studentised against the null distribution using the $$\text{formula } Z_{Yobs} = \frac{\hat{Y}_{obs} - \hat{Y}}{\sigma_Y}$$

Where $\hat{Y}$ and $\sigma_Y$ are the first and square root of the second moment of all permuted $\hat{y}_i$ statistic values. Samples whose $Z_{Yobs}$ was greater than a predefined threshold, say c3, were statistically less likely to have the same ploidy in the reference and test groups. Results of the analysis of 98 maternal samples for chromosome 21 using this method are shown in FIG. 5.

In the case of fragment-size associated tests, the algorithm computes the proportion of small-size fragments found in test-loci and compares it with the respective proportion in reference-loci as described in Statistical Method 4 below.

Statistical Method 4:

Fragment Size Proportions. For each sample the number and size of fragments aligned onto the human reference genome at the corresponding TACS coordinates, is extracted. The data is subsequently filtered so as to remove fragment-sizes considered statistical outliers using the median outlier detection method. Specifically, outliers are defined as those fragments whose size is above or below the thresholds, $F_{thr}$, set by equation:

$$F_{thr} = F_{median} \pm (X \times IQR)$$

Where $F_{median}$ is the median fragment-size of all fragments of a sample, X is a variable that can take values from the set of $\mathbb{R}+$, and IQR is the interquartile range of fragment sizes. Thereafter, a binomial test of proportions is carried out to test for supporting evidence against the null hypothesis, H0, where this is defined as:

H0: The proportion of small fragments of the test-region is not different from the proportion of small-fragments of the reference region, In various embodiments of the invention, small fragments are defined as those fragments whose size is less than or equal to a subset of $\mathbb{Z}+$ that is upper-bounded by 160 bp. If we define the set of all TACS as T, then the test region can be any proper subset S which defines the region under investigation, and the reference region is the relative complement of S in T. For example, in one embodiment of the invention, the set S is defined by all TACS-captured sequences of chromosome 21 and thus the reference set is defined by all TACS-captured fragments on the reference chromosomes, and/or other reference loci The alternative hypothesis, H1, is defined as:

H1: The proportion of small fragments of the test-region is not equal to the proportion of test fragments of the reference region.

As such, and taking into account continuity correction, the following score is computed (Brown et. Al, Harrel):

$$W_{test} = (\bar{p} - p_{ref}) / \sqrt{\frac{\bar{p}(1-\bar{p})}{N_{test}}}$$

Where $$\bar{p} = \frac{(\bar{F} + 0.5)}{(N_{test} + 1)}$$

$$\bar{p}_{ref} = \frac{(F_{ref} + 0.5)}{(N_{ref} + 1)}$$

$\bar{F}$ is the number of small-size fragments on the test-region, $F_{ref}$ the number of small size fragments on the reference region, $N_{test}$ the number of all fragments on the test region and $N_{ref}$ the number of all fragments on the reference region.

Figure 6:
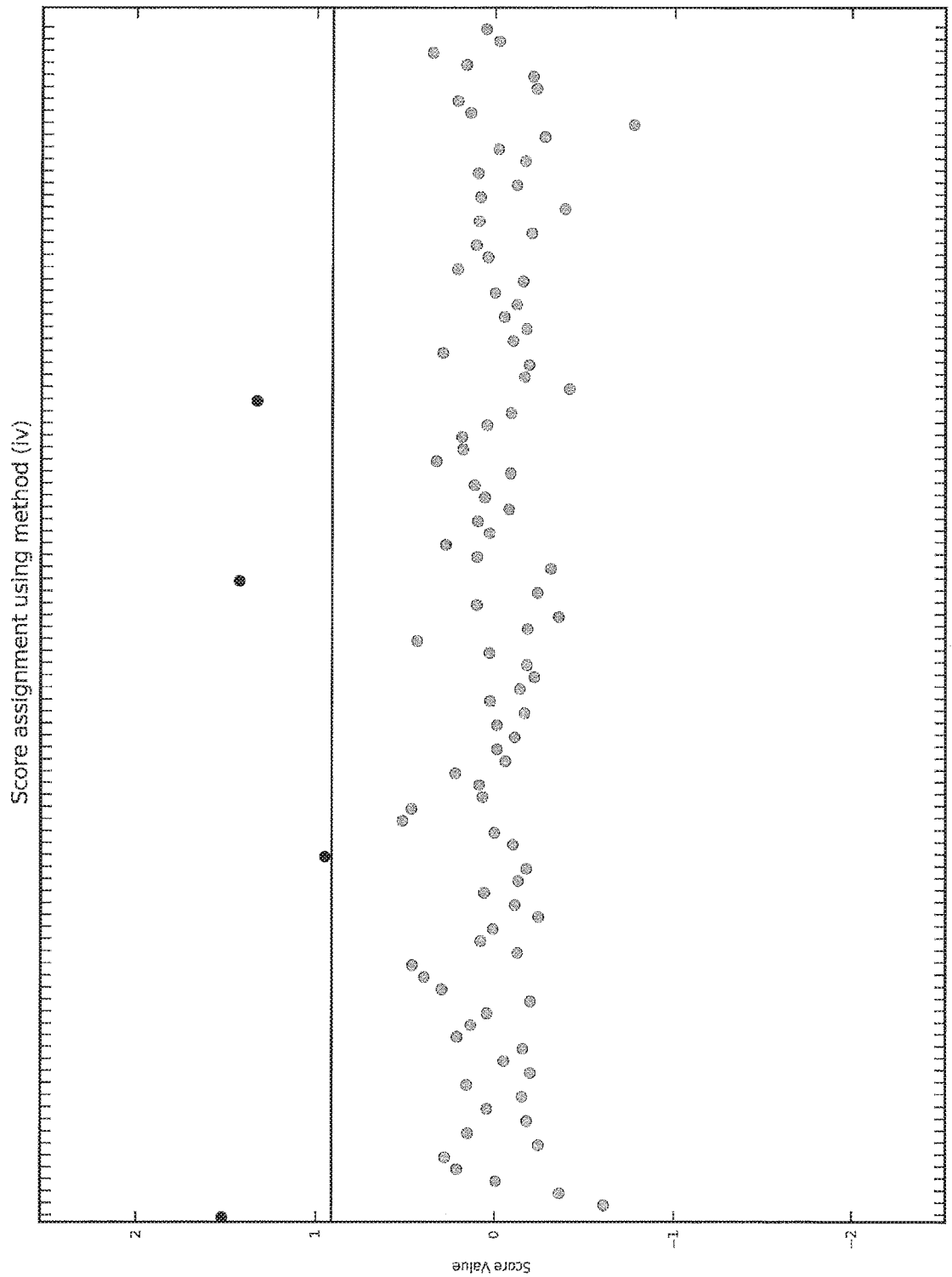
FIG. 6 is a graph of the score value assigned to 98 maternal blood samples subjected to multiplexed parallel analysis of targeted genomic regions for trisomy 21 risk detection, analyzed using a binomial test of proportions on fragment sizes (referred to herein as in statistical method 4)

For each sample, the algorithm tests sequentially the proportion of fragment sizes of regions under investigation (for example, but not limited to, chromosome 21, chromosome 18, chromosome 13) against reference regions; those not under investigation at the time of testing. For each sample a score is assigned for each test. Scores above a set-threshold, say c4, provide evidence against the null hypothesis. Results of the analysis of 98 maternal samples from chromosome 21 using this method are shown in FIG. 6.

Weighted Score Method 1:

In one embodiment of the method, a weighted score was attributed to each sample s, computed as a weighted sum of all statistical methods using the formula:

$$V_s(R,F) = z_1 \max\{R_s, F_s\} + (1-z_1)\min\{R_s, F_s\}$$

Where $R_s$ is the run-specific corrected score arising from a weighted contribution of each read-depth related statistical method for sample s and is defined as:

$$R_s = \frac{(\Sigma_i w_i S_{is} - \overline{R_r})}{\sigma_r}$$

and $\overline{R_r}$ is the run-specific median value calculated from the vector of all unadjusted read-depth related weighted scores that arise from a single sequencing run, and $\sigma_r$ is a multiple of the standard deviation of R scores calculated from a reference set of 100 euploid samples. The terms max $\{R_s, F_s\}$ and min $(\{R_s, F_s\}$ denote the maximum and minimum values of the bracketed set, respectively.

$F_s$ is the run-specific corrected score arising from the fragment-size related statistical method and is defined as:

$$F_s = \frac{(W_{test} - \overline{R_f})}{\sigma_f}$$

where $W_{test}$ is as defined earlier, $\overline{R_f}$ is the run specific median calculated from the vector of all unadjusted fragment-related statistical scores that arise from a single sequencing run, and $\sigma_f$ is a multiple of the standard deviation of F scores calculated from a reference set of 100 euploid samples.

Figure 7:
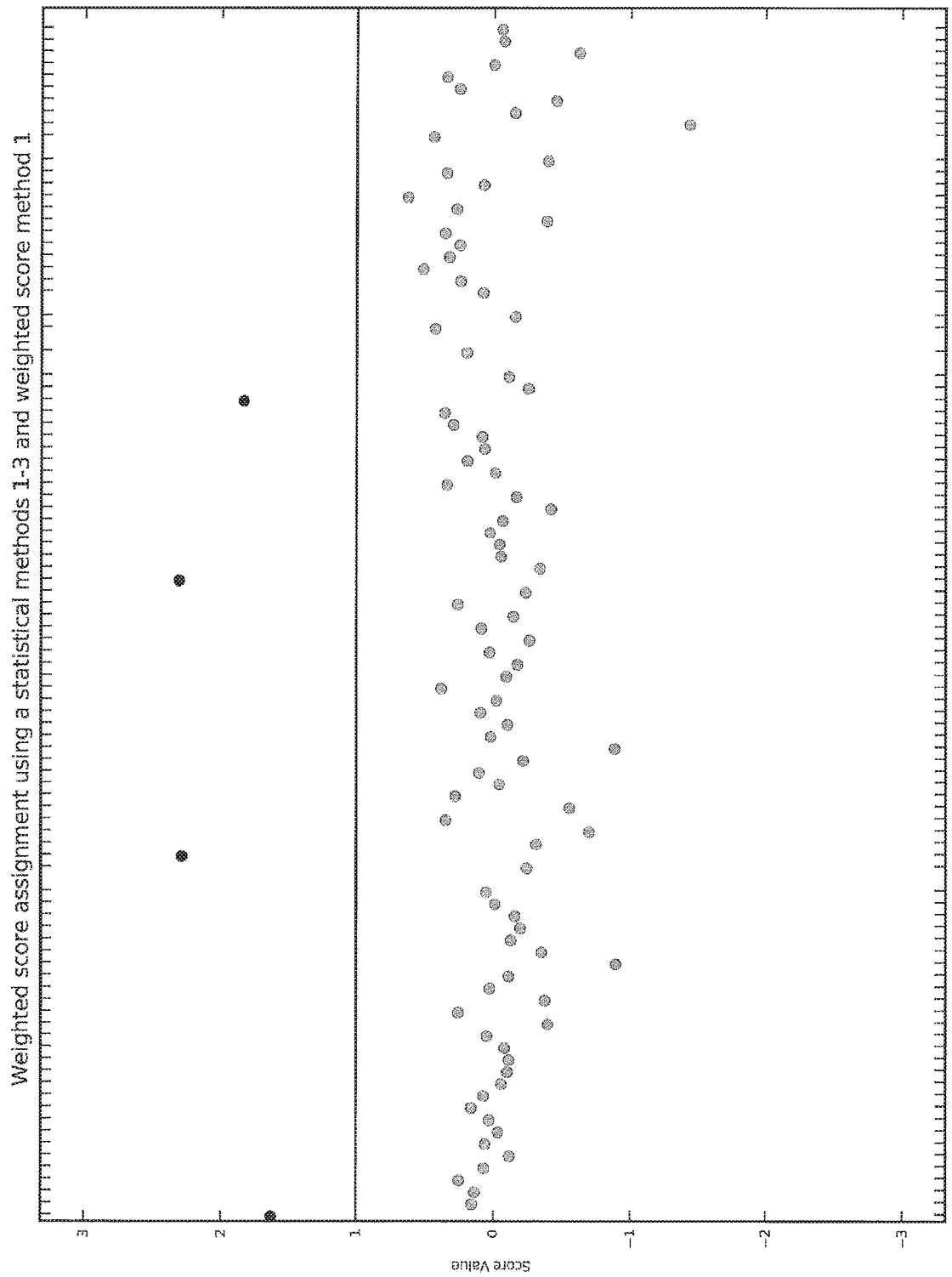
FIG. 7 is a graph of the weighted score values of the 98 maternal blood samples resulting from analysis using statistical methods 1, 2, 3 and the weighted score method 1 as shown in FIGS. 3-5.
Figure 8:
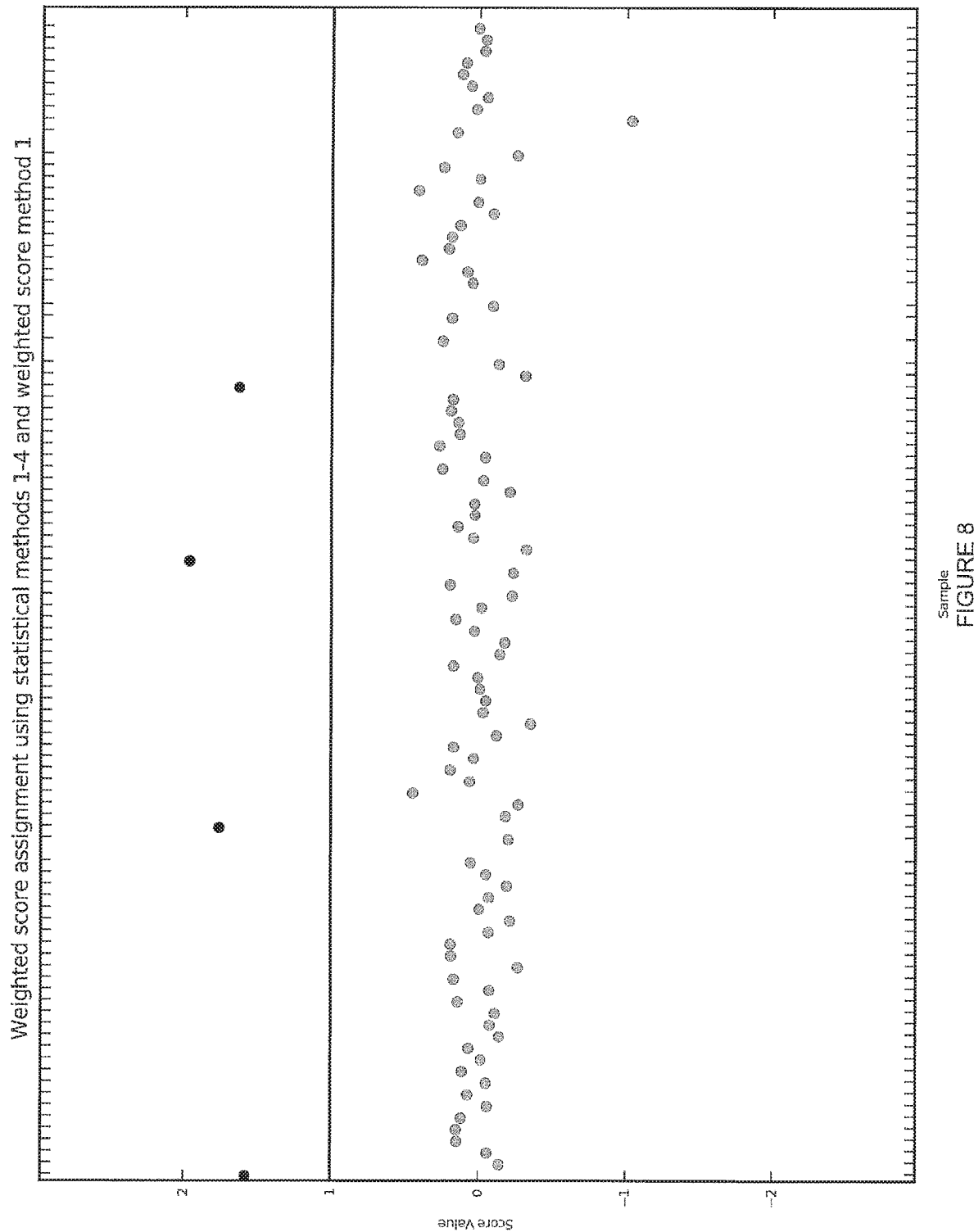
FIG. 8 is a graph of the weighted score values of the 98 maternal blood samples resulting from analysis using statistical methods 1, 2, 3, 4 and the weighted score method 1 as shown in FIGS. 3-6.

A unique classification score of less than a predefined value indicates that there is no evidence from the observed data that a sample has a significant risk of aneuploidy. Results for the 98 maternal samples using the weighted score approach on a subset of the methods is shown in FIG. 7, and from all methods in FIG. 8.

Weighted Score Method 2:

In another embodiment of the method, the weighted score arising from the statistical methods described above was used to assign each sample a unique aneuploidy risk score using the formula:

$$R(t,c) = \sum_{j=0}^{j=N} w_j \frac{t_j}{c_j}$$

where R is the weighted score result, $w_j$ the weight assigned to method j, $t_j$ the observed score resulting from method j, and $c_j$ the threshold of method.

Figure 9:
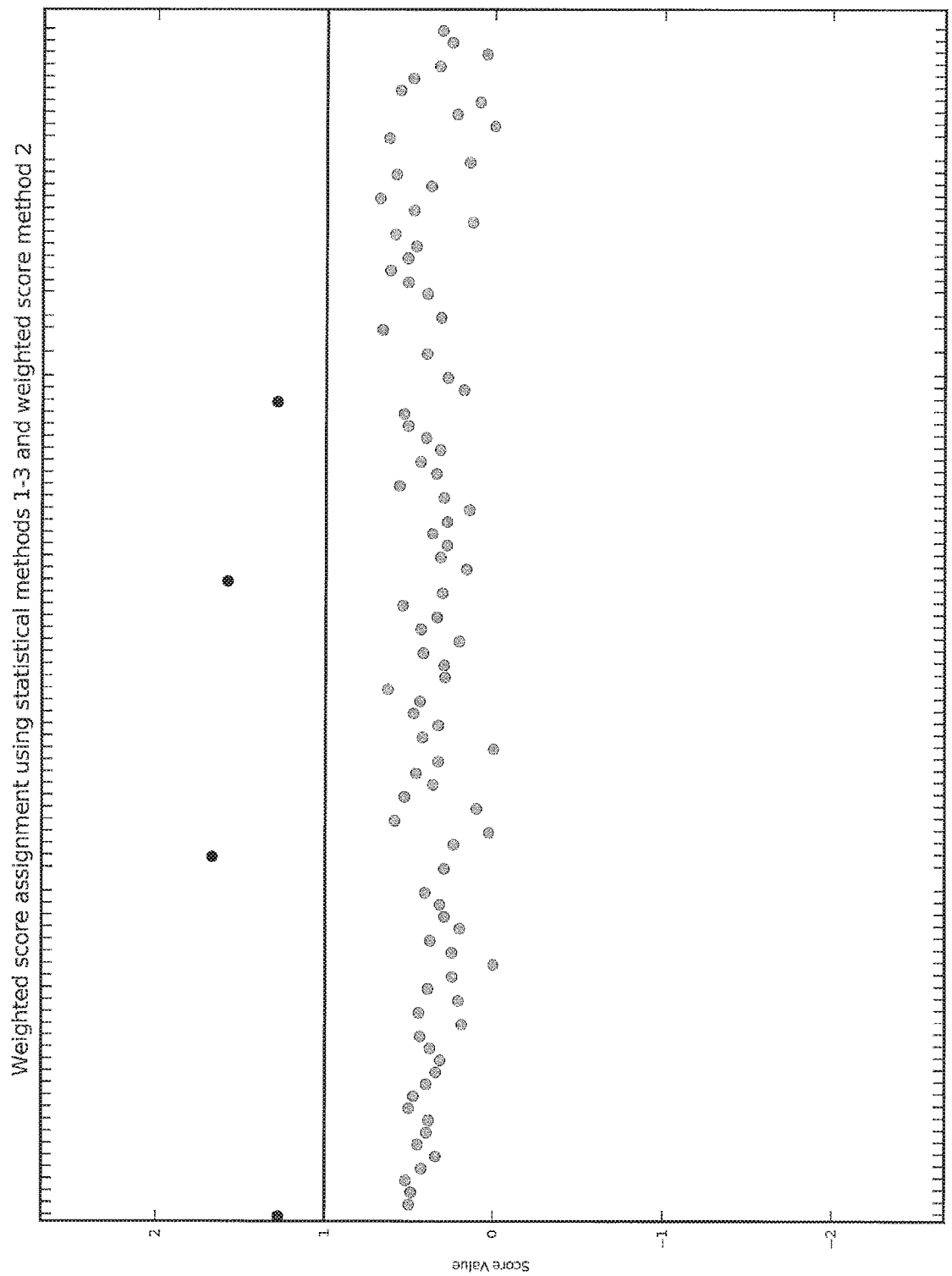
FIG. 9 is a graph of an alternative weighted approach, weighted score method 2, on the score values of the 98 maternal blood samples resulting from analysis using statistical methods 1, 2 and 3 as shown in FIGS. 3-5.

A unique classification score of less than a predefined value indicates that there is no evidence from the observed data that a sample has a significant risk of aneuploidy. Results for the 98 maternal samples using Statistical Methods 1-3 with the weighted score method 2 are shown in FIG. 9.

Since all read depths from baits in the reference group were assumed to be generated from the same population, and in order to have a universal threshold, run-specific adjustments were also employed to alleviate run-specific biases.

Figure 10:
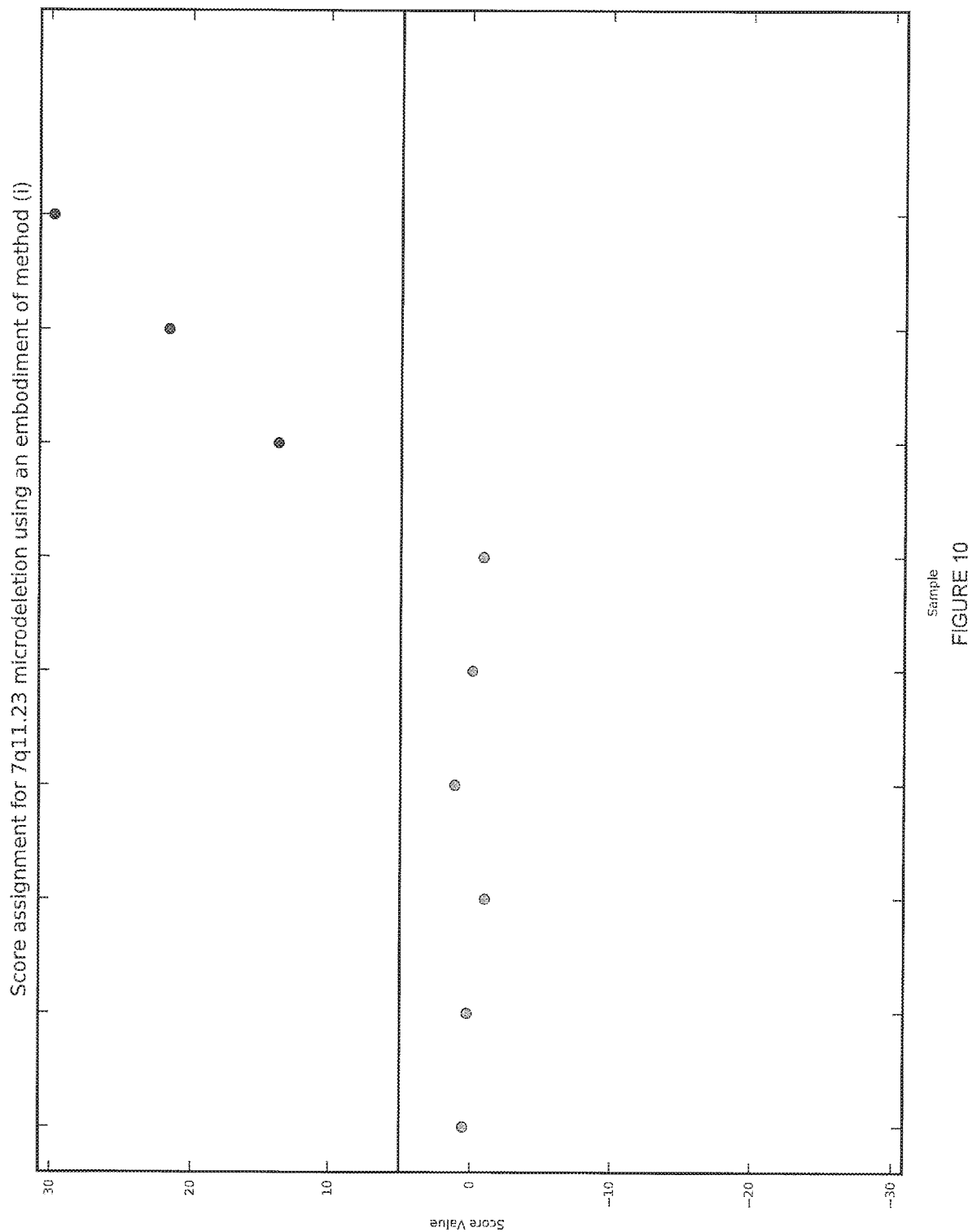
FIG. 10 is a graph of the score value assignment of 9 synthetic samples subjected to multiplexed parallel analysis of targeted genomic regions using TACS for 7q11.23, analyzed using an embodiment of statistical method 1 for the detection of microdeletions.

The aforementioned method(s), are also suitable for the detection of other genetic abnormalities, such as but not limited to, subchromosomal abnormalities. A non-limiting example is the contiguous partial loss of chromosomal material leading to a state of microdeletion, or the contiguous partial gain of chromosomal material leading to a state of microduplication. A known genetic locus subject to both such abnormalities is 7q11.23. In one embodiment of statistical method 1, synthetic plasma samples of 5%, 10% and 20% fetal material were tested for increased risk of microdeletion and/or microduplication states for the genetic locus 7q11.23. Results are illustrated in FIG. 10 for the cases of microdeletion and FIG. 11 for the cases of microduplication.

For point mutations various binomial tests are carried out that take into consideration the fetal fraction estimate of the sample, f, the read-depth of the minor allele, r, and the total read-depth of the sequenced base, n. Two frequent, yet non-limiting examples involve assessment of the risk when the genetic abnormality is a recessive point mutation or a dominant point mutation.

In the non-limiting example of a recessive point mutation the null hypothesis tested is that both the mother and the fetus are heterozygous (minor allele frequency is 0.5) against the alternative in which the fetus is homozygous (minor allele frequency is 0.5−f/2). A small p-value from the corresponding likelihood ratio test would indicate evidence against the null. In the non-limiting example of a dominant point mutation the null hypothesis tested is that the mother and fetus are homozygous at the given position against the alternative in which only the fetus is heterozygous for the given position. A small p-value from the corresponding likelihood ratio test would indicate evidence against the null.

In addition to the above, fetal sex determination methods were also developed, with non-limiting examples given below. In one embodiment of the invention, fetal sex was assigned to a sample using a Poisson test using the formula:

$$Pr(r_y \leq k) = e^{-\lambda} \sum_{i=0}^{i=k} \frac{\lambda^i}{i!}$$

where $$\lambda = \frac{fB\mu}{2}$$

and f is the fetal fraction estimate of the sample, B is the number of target sequences on chromosome Y, μ is the read-depth of the sample and k is the sum of reads obtained from all targets B. The null hypothesis of the Poisson test was that the sample is male. A value of $Pr(r_y)$ less than a threshold cy was considered as enough evidence to reject the null hypothesis, i.e. the sample is not male. If any of the terms for computing $Pr(r_y)$ were unavailable, then the sample's sex was classified as NA (not available).

In another embodiment of the invention, fetal sex was assigned using the average read-depth of target sequences on chromosome Y. If the average read-depth of the target-sequences was over a predefined threshold, where such threshold may be defined using other sample-specific characteristics such as read-depth and fetal-fraction estimate, the fetal sex was classified as male. If the average read-depth was below such threshold then the sample was classified as female.

Fetal Fraction Estimation

Several methods have been developed to estimate fetal fraction that can be applied to singleton and/or to multiple gestation pregnancies. As such, and dependent on the type of pregnancy, the fetal fraction estimate can be obtained from either method or as a weighted estimate from a subset and/or all developed methods. Some non-limiting examples are given below.

In one embodiment, a machine learning technique has been developed based on Bayesian inference to compute the posterior distribution of fetal DNA fraction using allelic counts at heterozygous loci in maternal plasma of singleton pregnancies. Three possible informative combinations of maternal/fetal genotypes were utilized within the model to identify those fetal DNA fraction values that get most of the support from the observed data.

Let f denote the fetal DNA fraction. If the mother is heterozygous at a given genomic locus, the fetal genotype can be either heterozygous or homozygous resulting in expected minor allele frequencies at 0.5 and 0.5-f/2, respectively. If the mother is homozygous and the fetus is heterozygous then the expected minor allele frequency will be f/2. A Markov chain Monte Carlo method (a Metropolis-Hastings algorithm) (The R Foundation (2015) *The R Project for Statistical Computing*) was used with either a non-informative or an informative prior (i.e. incorporate additional information such as gestational age, maternal weight etc.) to obtain a sequence of random samples from the posterior probability distribution of fetal DNA fraction that is based on a finite mixture model.

In another embodiment, the fetal fraction estimate is computed only from the fetus-specific minor allele frequency (MAF) cluster, i.e the cluster formed when the mother is homozygous and the fetus is heterozygous for a given genomic locus. It is assumed that the mean value of the fetal fraction estimate is normally distributed as $N(2\bar{x}; \sigma_{\bar{x}})$, where $\bar{x}$ is the mean of the fetus-specific MAF, and $\sigma_{\bar{x}}$ is the standard deviation of the fetus-specific MAF. The fetal fraction estimate is then obtained from percentiles of the computed distribution, $N(2\bar{x}, \sigma_{\bar{x}})$.

For multiple gestation pregnancies, non-limiting examples of which include monozygotic and dizygotic twin pregnancies, triplet pregnancies and various egg and/or sperm donor cases, the fetal fraction can be estimated using information obtained from heterozygous genetic loci whose MAF value is less than a threshold, say $M_{thresh}$, and derived from potential fetus-specific SNPs. The ordinarily skilled artisan will appreciate that fetus specific SNPs can originate from any fetus, or from any possible combination of the fetuses or from all the fetuses of the gestation. As such, an algorithm that estimates the fetal fraction of the fetus with the smallest contribution to the total fetal content, by taking into account the combinatorial contribution of each fetus to the MAF values that define fetus-specific SNPs, and also allows for inhomogeneous contribution of fetal material to the total fetal content of plasma derived material has been developed. To this effect, a two-step approach is employed by the algorithm.

In one embodiment of the algorithm, the multiple gestation pregnancy under consideration is a dizygotic twin pregnancy. As a first step, the algorithmic implementation of the model utilizes all informative SNPs and allows for inhomogeneous fetal contribution that can be explained with a fold-difference in fetal fraction estimates of a set threshold, say cf. Specifically, if f1 and f2 represent the fetal fractions of fetus one and fetus two, and f1<=f2, then the assumption is that f2<=cf f1, with cf being a positive real number greater than or equal to 1. Under this assumption, the observed data D, defined as counts of the alternate and reference alleles at informative SNP loci, are believed to be generated from a mixture distribution of three Binomials (defined by parameters, f1/2, f2/2 and (f1+f2)/2), with the posterior distribution p(f1,f2|D) being proportional to the observational model which can be written as p(f1|f2,D) p(f2|D). The posterior distribution p(f1,f2|D) is sampled with an MCMC Metropolis-Hastings algorithm using a uniform prior. The empirical quantile approach is performed on the generated data array to infer the fetal fractions. As a second step, the algorithm runs a model-based clustering algorithm (Finite Gaussian mixture modeling fitted via EM algorithm; R-package: mclust) to identify whether there exists a separate outlier SNP cluster which is believed to be centered around f1/2. Existence of such a cluster with a mean invalidating the cf >=f2/f1 assumption, leads to estimation of f1 using only SNPs part of the identified cluster.

REFERENCES

Chris Fraley and Adrian E. Raftery (2002). Model-based Clustering, Discriminant Analysis and Density Estimation. Journal of the American Statistical Association, 97:611-631

Chris Fraley, Adrian E. Raftery, T. Brendan Murphy, and Luca Scrucca (2012). mclust Version 4 for R: Normal Mixture Modeling for Model-Based Clustering, Classification, and Density Estimation. Technical Report No. 597, Department of Statistics, University of Washington Example 5: Results of Maternal Sample Analysis Ninety-eight maternal samples were analyzed for trisomy chromosome 21 (T21) risk according to the methodologies described in Examples 1-4. The score values of T21 risk detection for the 98 samples using the statistical methods 1, 2, 3 and 4, are plotted in the graphs shown in FIGS. 3, 4, 5 and 6, respectively. Each dot represents the score value for an individual sample. The line illustrates the threshold "c" (c=3.00 for method 1 and c=5.00 for method 2, c=4.00 for method 3 and c=0.91 for method 4). Scores that exceeded the threshold line in the positive direction (i.e. score value >c, darker dots) were assigned a high risk of aneuploidy as opposed to scores that did not exceed the threshold (i.e. score value <c, lighter dots). Using all statistical methods, four samples were assigned as high risk for T21 aneuploidy. Moreover, all statistical methods indicated the same samples as being high risk even though the scores followed different distributions in the different methods.

The weighted scores that resulted from combinations of statistical methods 1, 2, 3 and 4 of the algorithm (as described in Example 4) are plotted in the graphs of FIGS. 7-9, wherein again each dot represents the score value for an individual sample and the line represents the threshold. The weighted score values also showed the same four samples as being high risk.

The four samples identified as being of high-risk for T21 by the above analyses were independently verified as being from pregnancies having a fetus with trisomy 21, thereby confirming the accuracy of the method for testing for risk of T21.

Figure 11:
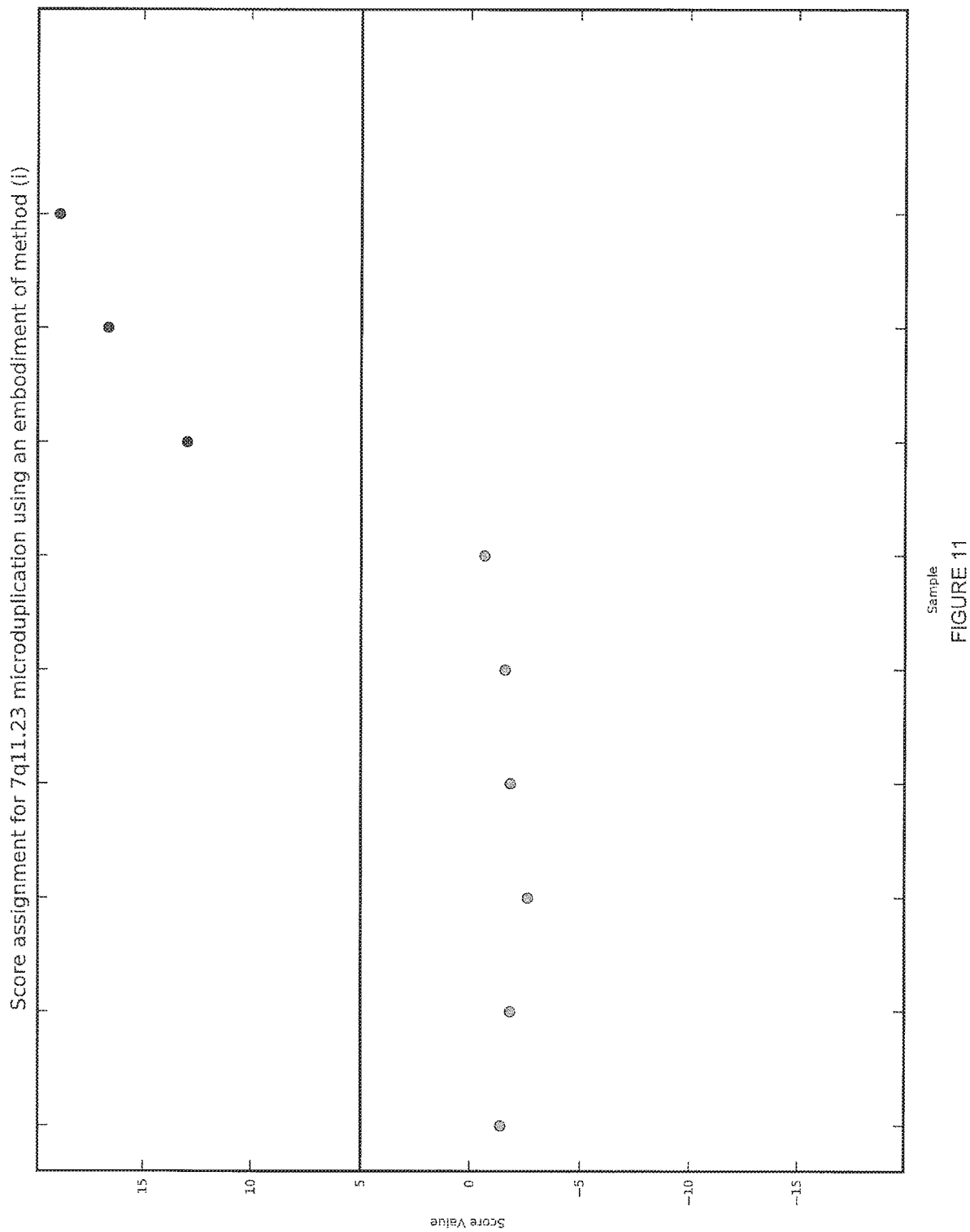
FIG. 11 is a graph of the score value assignment of 9 synthetic samples subjected to multiplexed parallel analysis of targeted genomic regions using TACS for 7q11.23, analyzed using an embodiment of statistical method 1 for the detection of microduplications.

Furthermore, results from the analysis of microdeletion and microduplication synthetic samples are illustrated in FIGS. 10-11.

What is claimed is:

1. A method of processing a sample, comprising:
    a. obtaining said sample comprising a mixture of maternal and fetal DNA from a human subject;
    b. contacting the mixture with a pool of Target Capture Sequences (TACS), wherein the pool comprises TACS that bind to one or more chromosomes or chromosomal regions of interest, wherein each TACS within the pool binds to the chromosome(s) or chromosomal region(s) of interest at least 150 base pairs away, on both the 5' end and the 3' end, from regions harboring Copy Number Variations (CNVs), Segmental duplications or repetitive DNA elements;
    c. isolating members of the mixture that bind to the TACS to obtain an enriched library;
    d. sequencing the enriched library thereby obtaining a read depth for at least one test loci and reference loci;
    e. processing sequentially the read depth of the at least one test loci against the read-depth of the at least one reference loci by:
        i. removing inadequately sequenced loci;
        ii. alleviating GC-content bias.

2. The method for processing a sample according to claim 1, wherein the TACS are biotinylated and are bound to streptavidin-coated magnetic beads or can be free in solution.

3. The method for processing a sample according to claim 1, wherein the GC content bias is alleviated by grouping the at least one test loci and the at least one reference loci of matching GC-content.

4. The method for processing a sample according to claim 1, further comprising the step of quantifying the fetal DNA fraction of the sample.

5. The method for processing a sample according to claim 4, wherein if the quantification of the fetal DNA fraction of the sample is below a predefined threshold, the sample is discarded.

6. The method of processing a sample according to claim 1, wherein the GC content of the TACS is between 19% and 50%.

7. The method for processing a sample according to claim 1, wherein the chromosome(s) or chromosomal region(s) of interest is chromosome 13, 18, 21, X and/or Y.

8. The method for processing a sample according to claim 1, wherein the ploidy status classification is achieved by application of a statistical method selected from the group consisting of a t-test, a bivariate nonparametric bootstrap test, a stratified permutation test and a binomial test of proportions and/or combinations thereof.

9. A method of classifying a ploidy status, comprising:
    a. processing a sample comprising a mixture of maternal and fetal DNA according to the method of claim 1,
    b. classifying the ploidy status of the sample by assigning a score, wherein if the score is above a predefined threshold, the sample is classified as high risk of aneuploidy.

10. A method of determining a fetal sex, comprising:
    a. processing a sample comprising a mixture of maternal and fetal DNA according to the method of claim 1,
    b. assigning the fetal sex of the sample as
        i. male if the average read-depth of the at least one test loci is above a predefined threshold or
        ii. female if the average read-depth of the at least one test loci is below a predefined threshold.

* * * * *

SEQUENCE LISTING

<160> NUMBER OF SEQ ID NOS: 3

<210> SEQ ID NO 1
<211> LENGTH: 33
<212> TYPE: DNA
<213> ORGANISM: Artificial Sequence
<220> FEATURE:
<223> OTHER INFORMATION: Synthetic oligonucleotide: adaptor P5_F
<220> FEATURE:
<221> NAME/KEY: modified_base
<222> LOCATION: (1)..(2)
<223> OTHER INFORMATION: phosphorothioate bond
<220> FEATURE:
<221> NAME/KEY: modified_base
<222> LOCATION: (2)..(3)
<223> OTHER INFORMATION: phosphorothioate bond
<220> FEATURE:
<221> NAME/KEY: modified_base
<222> LOCATION: (3)..(4)
<223> OTHER INFORMATION: phosphorothioate bond
<220> FEATURE:
<221> NAME/KEY: modified_base
<222> LOCATION: (4)..(5)
<223> OTHER INFORMATION: phosphorothioate bond
<220> FEATURE:
<221> NAME/KEY: modified_base
<222> LOCATION: (29)..(30)
<223> OTHER INFORMATION: phosphorothioate bond
<220> FEATURE:
<221> NAME/KEY: modified_base
<222> LOCATION: (30)..(31)
<223> OTHER INFORMATION: phosphorothioate bond
<220> FEATURE:
<221> NAME/KEY: modified_base
<222> LOCATION: (31)..(32)
<223> OTHER INFORMATION: phosphorothioate bond
<220> FEATURE:
<221> NAME/KEY: modified_base
<222> LOCATION: (32)..(33)
<223> OTHER INFORMATION: phosphorothioate bond

<400> SEQUENCE: 1
acactctttc cctacacgac gctcttccga tct                              33

<210> SEQ ID NO 2
<211> LENGTH: 34
<212> TYPE: DNA
<213> ORGANISM: Artificial Sequence
<220> FEATURE:
<223> OTHER INFORMATION: Synthetic oligonucleotide: adaptor P7_F
<220> FEATURE:
<221> NAME/KEY: modified_base
<222> LOCATION: (1)..(2)
<223> OTHER INFORMATION: phosphorothioate bond
<220> FEATURE:
<221> NAME/KEY: modified_base
<222> LOCATION: (2)..(3)
<223> OTHER INFORMATION: phosphorothioate bond
<220> FEATURE:
<221> NAME/KEY: modified_base

```
<222> LOCATION: (3)..(4)
<223> OTHER INFORMATION: phosphorothioate bond
<220> FEATURE:
<221> NAME/KEY: modified_base
<222> LOCATION: (4)..(5)
<223> OTHER INFORMATION: phosphorothioate bond
<220> FEATURE:
<221> NAME/KEY: modified_base
<222> LOCATION: (30)..(31)
<223> OTHER INFORMATION: phosphorothioate bond
<220> FEATURE:
<221> NAME/KEY: modified_base
<222> LOCATION: (31)..(32)
<223> OTHER INFORMATION: phosphorothioate bond
<220> FEATURE:
<221> NAME/KEY: modified_base
<222> LOCATION: (32)..(33)
<223> OTHER INFORMATION: phosphorothioate bond
<220> FEATURE:
<221> NAME/KEY: modified_base
<222> LOCATION: (33)..(34)
<223> OTHER INFORMATION: phosphorothioate bond

<400> SEQUENCE: 2
gtgactggag ttcagacgtg tgctcttccg atct                              34

<210> SEQ ID NO 3
<211> LENGTH: 13
<212> TYPE: DNA
<213> ORGANISM: Artificial Sequence
<220> FEATURE:
<223> OTHER INFORMATION: Synthetic oligonucleotide: adaptor_P5+P7_R
<220> FEATURE:
<221> NAME/KEY: modified_base
<222> LOCATION: (1)..(2)
<223> OTHER INFORMATION: phosphorothioate bond
<220> FEATURE:
<221> NAME/KEY: modified_base
<222> LOCATION: (2)..(3)
<223> OTHER INFORMATION: phosphorothioate bond
<220> FEATURE:
<221> NAME/KEY: modified_base
<222> LOCATION: (3)..(4)
<223> OTHER INFORMATION: phosphorothioate bond
<220> FEATURE:
<221> NAME/KEY: modified_base
<222> LOCATION: (4)..(5)
<223> OTHER INFORMATION: phosphorothioate bond
<220> FEATURE:
<221> NAME/KEY: modified_base
<222> LOCATION: (9)..(10)
<223> OTHER INFORMATION: phosphorothioate bond
<220> FEATURE:
<221> NAME/KEY: modified_base
<222> LOCATION: (10)..(11)
<223> OTHER INFORMATION: phosphorothioate bond
<220> FEATURE:
<221> NAME/KEY: modified_base
<222> LOCATION: (11)..(12)
<223> OTHER INFORMATION: phosphorothioate bond
<220> FEATURE:
<221> NAME/KEY: modified_base
<222> LOCATION: (12)..(13)
<223> OTHER INFORMATION: phosphorothioate bond

<400> SEQUENCE: 3
agatcggaag agc                                                     13
```